US012565531B2

(12) United States Patent
Xu et al.

(10) Patent No.: US 12,565,531 B2
(45) Date of Patent: *Mar. 3, 2026

(54) BISPECIFIC FUSION PROTEIN FOR TUMOR TREATMENT

(71) Applicant: JIANGSU ALPHAMAB BIOPHARMACEUTICALS CO., LTD., Suzhou (CN)

(72) Inventors: Ting Xu, Suzhou (CN); Kangping Guo, Suzhou (CN); Junfang Xu, Suzhou (CN); Pilin Wang, Suzhou (CN); Yuhao Jin, Suzhou (CN)

(73) Assignee: JIANGSU ALPHAMAB BIOPHARMACEUTICALS CO., LTD., Suzhou (CN)

( * ) Notice: Subject to any disclaimer, the term of this patent is extended or adjusted under 35 U.S.C. 154(b) by 850 days.

This patent is subject to a terminal disclaimer.

(21) Appl. No.: 17/782,415

(22) PCT Filed: Dec. 3, 2020

(86) PCT No.: PCT/CN2020/133665
§ 371 (c)(1),
(2) Date: Jun. 3, 2022

(87) PCT Pub. No.: WO2021/110106
PCT Pub. Date: Jun. 10, 2021

(65) Prior Publication Data
US 2023/0015590 A1 Jan. 19, 2023

(30) Foreign Application Priority Data

Dec. 4, 2019 (WO) ................ PCT/CN2019/123066
Nov. 9, 2020 (WO) ................ PCT/CN2020/127556

(51) Int. Cl.
*C07K 16/28* (2006.01)
*A61P 35/00* (2006.01)
*A61K 39/00* (2006.01)

(52) U.S. Cl.
CPC .......... *C07K 16/2818* (2013.01); *A61P 35/00* (2018.01); *C07K 16/2827* (2013.01); *A61K 2039/545* (2013.01); *C07K 2317/31* (2013.01); *C07K 2317/52* (2013.01); *C07K 2317/76* (2013.01)

(58) Field of Classification Search
None
See application file for complete search history.

(56) References Cited

FOREIGN PATENT DOCUMENTS

| CN | 106103482 A | 11/2016 | | |
|---|---|---|---|---|
| CN | 106397592 A | 2/2017 | | |
| CN | 106967172 A | 7/2017 | | |
| CN | 107400166 A | 11/2017 | | |
| CN | 109071639 A | 12/2018 | | |
| EP | 3626745 A1 | 3/2020 | | |
| JP | 2017501155 A | 1/2017 | | |
| WO | 2014209804 A1 | 12/2014 | | |
| WO | WO-2018068695 A1 * | 4/2018 | ......... | A61K 39/3955 |
| WO | 2019042153 A1 | 3/2019 | | |
| WO | 2019090002 A1 | 5/2019 | | |
| WO | 2019233413 A1 | 12/2019 | | |

OTHER PUBLICATIONS

PCT/CN2020/133665 International Search Report dated Mar. 3, 2021.
Coward, J., et al., Preliminary safety, efficacy, and ppharmacokinetics (PK) results of KN046 (bispecific anti-PD-L1/CTLA4) from a first-in-human study in subjects with advanced solid tumors, J of Clinical Oncology, vol. 37, No. 15 Suppl., May 26, 2019.
Peking University, et al., Identifier: NCT04040699, Clinicaltrials.gov., Nov. 13, 2019.
Zhao, H.Y., et al., The preliminary efficacy and safety data of KN046 in patients failed on prior immune checkpoint inhibitors therapy, J of Clinical Oncology, vol. 38, No. 15 Suppl. May 31, 2020.
Clinical Trials.gov; National Library of Medicine, KN026 Combined with KN046 in Subjectes with HER2 Positive Solid Tumor, Shen Lin, Peking University; Apr. 9, 2024.
Journal of Clinical Oncology; Preliminary safety, efficacy, and pharmacokinetics (PK) results of KN046 (bispecific anti-PD-L1/CTLA4) from a first-in-human study in subjects with advanced solid tumors; Meeting abstract, 2019 ASCO Annual Meeting, May 26, 2019.
Zhang et al., Molecular Immunology, vol. 45, NR5, p. 1470-1476, Chemopreventive agents induce programmed death-1-ligand 1 (PD-L1) surface expression in breast cancer cells and promote PD-L1-medicated T cell apoptosis.
European 20894956.0 Extended European Search Report dated Nov. 28, 2023.
Anonymous; Alphamab Oncology Presentation, Sep. 1, 2020.
Lee, H.T., et al., Molecular mechanism of PD-1/PD-L1 blockade via anti-PD-L1 antibodies atezolizumab and durvalumab, Scientific Reports, vol. 7, No. 17, pp. 1-12, The Author(s), Jul. 17, 2017.
English Translation of Office Action issued Feb. 28, 2025 in Chinese Patent Application No. 202080082844.9.

* cited by examiner

*Primary Examiner* — Laura B Goddard
(74) *Attorney, Agent, or Firm* — Sughrue Mion, PLLC

(57) ABSTRACT

The present disclosure provides a use of a dimer in the preparation of a medicament for treating a tumor in a subject in need thereof, and the dimer formed by two polypeptide chains, with each of the two polypeptide chains comprising an antibody Fc subunit, wherein the dimer comprises two or more immunoglobulin single variable domains (ISVDs), at least one of the ISVDs is specific for PD-L1, and at least one of the ISVDs is specific for CTLA4. The present disclosure also provides a method for treating a tumor in a subject in need thereof, wherein the subject is resistant to the therapy of an immune checkpoint inhibitor.

12 Claims, 3 Drawing Sheets
Specification includes a Sequence Listing.

A

B

BISPECIFIC FUSION PROTEIN FOR TUMOR TREATMENT

CROSS REFERENCE TO RELATED APPLICATIONS

This application is a National Stage Application and claims priority under 35 U.S.C. § 371 to Patent Cooperation Treaty application PCT/CN2020/133665, filed Dec. 3, 2020, which claims the benefit of Patent Cooperation Treaty application PCT/CN2020/127556, filed Nov. 9, 2020, and Patent Cooperation Treaty application PCT/CN2019/123066, filed Dec. 4, 2019. Priority is claimed to these applications and the disclosure of these prior applications is considered part of the disclosure of this application and to the extent allowed the entire contents of the aforementioned applications are incorporated herein.

SEQUENCE LISTING

This application incorporates by reference in its entirety the Sequence Listing entitled "2022 Jun. 2 262790-510972_ST25", is 127,658 bytes in size and was created on Jun. 2, 2022, and filed electronically herewith.

BACKGROUND OF THE INVENTION

Blockade of the PD1/PD-L1 interaction could lead to enhanced tumor-specific T-cell immunity, which in turn will lead to clearance of tumor cells by the immune system. Programmed Death Ligand-1 (PD-L1) is expressed on antigen-presenting cells as well as many human tumor cells and have been shown to down-regulate T cell activation and cytokine secretion upon binding to PD-1.

Similarly, abrogating immune regulatory molecules such as cytotoxic T lymphocyte antigen 4 (CTLA4) represents a new and promising strategy to induce tumor regression and prolong patient survival by manipulation of the immune system. Anti-CTLA4 antibodies (such as ipilimumab) have also been developed and marketed for the treatment of tumor.

Recently, reports of concurrent therapy using separate intravenous doses of PD1/PD-L1 antibody and CTLA4 antibody were shown. However, there are a number of drawbacks associated with these concurrent therapies. For example, there is increased inconvenience to the patient, added pain, and added difficulty of manufacturing and characterizing multiple agents. In addition, sub-optimal efficacy and safety issues have been reported. Thus, there is still an unmet medical need for new promising agents for the treatment of tumors, especially agents capable of simultaneously acting on various targets.

SUMMARY OF THE INVENTION

The present disclosure provides a use of a dimer in the preparation of a medicament for treating a tumor in a subject in need thereof, and the dimer comprising two polypeptide chain monomers, with each of the two polypeptide chain monomers comprising an antibody Fc subunit. The dimer comprises two or more immunoglobulin single variable domains (ISVDs), at least one of the ISVDs is specific for PD-L1, and at least one of the ISVDs is specific for CTLA4. The present disclosure also provides a method for treating a tumor in a subject in need thereof, comprising administering to said subject an effective amount of the dimer, wherein said subject is resistant to the therapy of an immune checkpoint inhibitor.

In one aspect, the present disclosure provides a use of a dimer in the preparation of a medicament for treating a tumor in a subject in need thereof, wherein said is dimer formed by two polypeptide chains, with each of said two polypeptide chains comprising an antibody Fc subunit, said dimer comprises two or more immunoglobulin single variable domains (ISVDs), at least one of said ISVDs is specific for PD-L1, and at least one of said ISVDs is specific for CTLA4.

In some embodiments, at least one of said two polypeptide chains comprise both an ISVD specific for PD-L1 and an ISVD specific for CTLA4.

In some embodiments, each of said two polypeptide chains comprises both an ISVD specific for PD-L1 and an ISVD specific for CTLA4.

In some embodiments, for one or both of said two polypeptide chains, said ISVD specific for PD-L1 is fused to said ISVD specific for CTLA4, optionally via a linker.

In some embodiments, for one or both of said two polypeptide chains: said ISVD specific for PD-L1 is fused to said ISVD specific for CTLA4, optionally via a linker; and said ISVD specific for CTLA4 is fused to said antibody Fc subunit, optionally via a linker.

In some embodiments, for one or both of said two polypeptide chains: C terminus of said ISVD specific for PD-L1 is fused to N terminus of said ISVD specific for CTLA4, optionally via a linker; and C terminus of said ISVD specific for CTLA4 is fused to N terminus of said antibody Fc subunit, optionally via a linker.

In some embodiments, for one or both of said two polypeptide chains: said ISVD specific for PD-L1 is fused to said ISVD specific for CTLA4, optionally via a linker; and said ISVD specific for PD-L1 is fused to said antibody Fc subunit, optionally via a linker.

In some embodiments, for one or both of said two polypeptide chains: C terminus of said ISVD specific for CTLA4 is fused to N terminus of said ISVD specific for PD-L1, optionally via a linker; and C terminus of said ISVD specific for PD-L1 is fused to N terminus of said antibody Fc subunit, optionally via a linker.

In some embodiments, said antibody Fc subunit is derived from an IgG Fc subunit.

In some embodiments, said IgG is human IgG1.

In some embodiments, said antibody Fc subunit comprises an amino acid sequence as set forth in any one of SEQ ID NO: 35, 38 and 39.

In some embodiments, said ISVD specific for PD-L1 is capable of binding to N-terminal IgV domain of human PD-L1.

In some embodiments, said ISVD specific for PD-L1 is capable of binding to residues I54, Y56, E58, Q66 and/or R113 of human PD-L1 N-terminal IgV domain, wherein said human PD-L1 N-terminal IgV domain comprises an amino acid sequence as set forth in SEQ ID NO: 64.

In some embodiments, said ISVD specific for PD-L1 is capable of further binding to residues D61, N63, V68, M115, S117, Y123 and/or R125 of human PD-L1 N-terminal IgV domain, wherein said human PD-L1 N-terminal IgV domain comprises an amino acid sequence as set forth in SEQ ID NO: 64.

In some embodiments, said ISVD specific for PD-L1 is capable of binding to a conformational epitope of human PD-L1 N-terminal IgV domain, wherein said conformational epitope comprises residues I54, Y56, E58, Q66 and R113 of said human PD-L1 N-terminal IgV domain, and wherein said human PD-L1 N-terminal IgV domain comprises an amino acid sequence as set forth in SEQ ID NO: 64.

In some embodiments, said ISVD specific for PD-L1 is capable of binding to a conformational epitope of human PD-L1 N-terminal IgV domain, wherein said conformational epitope comprises residues I54, Y56, E58, Q66, R113, D61, N63, V68, M115, S117, Y123 and R125 of said human PD-L1 N-terminal IgV domain, and wherein said human PD-L1 N-terminal IgV domain comprises an amino acid sequence as set forth in SEQ ID NO: 64.

In some embodiments, said ISVD specific for PD-L1 is capable of blocking binding of PD-L1 to PD1.

In some embodiments, said ISVD specific for PD-L1 is capable of blocking binding of PD-L1 to CD80.

In some embodiments, said ISVD specific for PD-L1 cross-competes for binding to PD-L1 with a reference anti-PD-L1 antibody, wherein said reference anti-PD-L1 antibody comprises a heavy chain CDR3 comprising an amino acid sequence as set forth in SEQ ID NO: 1.

In some embodiments, said reference anti-PD-L1 antibody comprises a heavy chain CDR3 comprising an amino acid sequence as set forth in any one of SEQ ID NO: 5 and 9.

In some embodiments, said reference anti-PD-L1 antibody comprises a heavy chain CDR1 comprising an amino acid sequence as set forth in SEQ ID NO: 2.

In some embodiments, said reference anti-PD-L1 antibody comprises a heavy chain CDR1 comprising an amino acid sequence as set forth in any one of SEQ ID NO: 3 and 7.

In some embodiments, said reference anti-PD-L1 antibody comprises a heavy chain CDR2 comprising an amino acid sequence as set forth in any one of SEQ ID NO: 4, 8 and 11.

In some embodiments, said reference anti-PD-L1 antibody is an ISVD specific for PD-L1.

In some embodiments, said reference anti-PD-L1 antibody comprises a heavy chain variable domain comprising an amino acid sequence as set forth in any one of SEQ ID NO: 6, 10, 12, 13, 14 and 15.

In some embodiments, said reference anti-PD-L1 antibody comprises a heavy chain variable domain comprising an amino acid sequence as set forth in SEQ ID NO: 6.

In some embodiments, said ISVD specific for PD-L1 comprises a heavy chain CDR3 comprising an amino acid sequence as set forth in SEQ ID NO: 1.

In some embodiments, said ISVD specific for PD-L1 comprises a heavy chain CDR3 comprising an amino acid sequence as set forth in any one of SEQ ID NO: 5 and 9.

In some embodiments, said ISVD specific for PD-L1 comprises a heavy chain CDR1 comprising an amino acid sequence as set forth in SEQ ID NO: 2.

T In some embodiments, said ISVD specific for PD-L1 comprises a heavy chain CDR1 comprising an amino acid sequence as set forth in any one of SEQ ID NO: 3 and 7.

In some embodiments, said ISVD specific for PD-L1 comprises a heavy chain CDR2 comprising an amino acid sequence as set forth in any one of SEQ ID NO: 4, 8 and 11.

In some embodiments, said ISVD specific for PD-L1 comprises a heavy chain variable domain comprising an amino acid sequence as set forth in any one of SEQ ID NO: 6, 10, 12, 13, 14 and 15.

In some embodiments, said ISVD specific for PD-L1 comprises a heavy chain variable domain comprising an amino acid sequence as set forth in SEQ ID NO: 6.

In some embodiments, said ISVD specific for CTLA4 is capable of specifically binding to human CTLA4.

In some embodiments, said ISVD specific for CTLA4 is capable of blocking binding of CTLA4 to CD80.

In some embodiments, said ISVD specific for CTLA4 is capable of blocking binding of CTLA4 to CD86.

In some embodiments, said ISVD specific for CTLA4 cross-competes for binding to CTLA4 with a reference anti-CTLA4 antibody, wherein said reference anti-CTLA4 antibody comprises a heavy chain CDR3 comprising an amino acid sequence as set forth in SEQ ID NO: 19.

In some embodiments, reference anti-CTLA4 antibody comprises a heavy chain CDR1 comprising an amino acid sequence as set forth in SEQ ID NO: 17.

In some embodiments, said reference anti-CTLA4 antibody comprises a heavy chain CDR2 comprising an amino acid sequence as set forth in SEQ ID NO: 16.

In some embodiments, said reference anti-CTLA4 antibody comprises a heavy chain CDR2 comprising an amino acid sequence as set forth in any one of SEQ ID NO: 18, 21 and 23.

In some embodiments, said reference anti-CTLA4 antibody is an ISVD specific for CTLA4.

In some embodiments, said reference anti-CTLA4 antibody comprises a heavy chain variable domain comprising an amino acid sequence as set forth in any one of SEQ ID NO: 20, 22, and 24-32.

In some embodiments, said reference anti-CTLA4 antibody comprises a heavy chain variable domain comprising an amino acid sequence as set forth in SEQ ID NO: 20.

In some embodiments, said ISVD specific for CTLA4 comprises a heavy chain CDR3 comprising an amino acid sequence as set forth in SEQ ID NO: 19.

In some embodiments, said ISVD specific for CTLA4 comprises a heavy chain CDR1 comprising an amino acid sequence as set forth in SEQ ID NO: 17.

In some embodiments, said ISVD specific for CTLA4 comprises a heavy chain CDR2 comprising an amino acid sequence as set forth in SEQ ID NO: 16.

In some embodiments, said ISVD specific for CTLA4 comprises a heavy chain CDR2 comprising an amino acid sequence as set forth in any one of SEQ ID NO: 18, 21 and 23.

In some embodiments, said ISVD specific for CTLA4 comprises a heavy chain variable domain comprising an amino acid sequence as set forth in any one of SEQ ID NO: 20, 22, and 24-32.

In some embodiments, said ISVD specific for CTLA4 comprises a heavy chain variable domain comprising an amino acid sequence as set forth in SEQ ID NO: 20.

In some embodiments, said dimer is a homodimer.

In some embodiments, said linker comprises an amino acid sequence as set forth in any one of SEQ ID NO: 33-34.

In some embodiments, one or both of said two polypeptide chains comprises an amino acid sequence as set forth in any one of SEQ ID NO: 40-43, 46, 48 and 50.

In some embodiments, one or both of said two polypeptide chains comprises an amino acid sequence as set forth in SEQ ID NO 40.

In some embodiments, said dimer is capable of blocking binding of PD-L1 to PD-1.

In some embodiments, said dimer is capable of blocking binding of PD-L1 to CD80.

In some embodiments, said dimer is capable of blocking binding of CTLA4 to CD80.

In some embodiments, said dimer is capable of blocking binding of CTLA4 to CD86.

In some embodiments, said tumor is selected from a group consisting of NSCLC, melanoma, esophageal squamous cell carcinoma (ESCC), NPC and breast cancer.

In some embodiments, said tumor is selected from a group consisting of esophageal squamous cell carcinoma (ESCC) and nasopharyngeal carcinoma (NPC).

In some embodiments, said subject has been administrated an immune checkpoint inhibitor.

In some embodiments, said subject was not substantially responsive to said immune checkpoint inhibitor.

In some embodiments, said immune checkpoint inhibitor is selected from a group consisting of: PD-L1 inhibitor, PD-1 inhibitor and CTLA4 inhibitor.

In some embodiments, said subject has been administrated chemotherapy, chemoradiation, CTL cell therapy, EGFR tyrosine kinase inhibitors (TKIs), and/or angiogenesis inhibitors.

In some embodiments, said chemotherapy comprises first line chemotherapy and/or second line chemotherapy.

In some embodiments, said second line chemotherapy comprises paclitaxel, docetaxel, capecitabine and/or 5-FU.

In some embodiments, said tumor is selected from a group consisting of locally advanced-stage or metastatic melanoma, non-keratinized locally advanced recurrent or metastatic NPC, metastatic NSCLC, squamous and non-squamous NSCLC, recurrent or metastatic ESCC and Triple-negative breast cancer (TNBC).

In some embodiments, said tumor is selected from a group consisting of advanced NSCLC without EGFR mutation or ALK fusions, NSCLC with EGFR Exon 20 insertion mutation, NPC with positive PD-L1 expression and locally advanced inoperable or metastatic TNBC.

In some embodiments, said dimer is administrated in combination with a chemotherapy agent.

In some embodiments, said chemotherapy agent comprises platinum doublets and/or paclitaxel.

In some embodiments, said chemotherapy agent comprises cisplatin, gemcitabine and/or nab-paclitaxel.

In another aspect, the present disclosure provides a method for treating a tumor in a subject in need thereof, comprising administering to said subject an effective amount of the dimer of the present disclosure.

In some embodiments, said tumor comprises is selected from a group consisting of NSCLC, melanoma, esophageal squamous cell carcinoma (ESCC), NPC and breast cancer.

In some embodiments, said tumor is selected from a group consisting of esophageal squamous cell carcinoma (ESCC) and nasopharyngeal carcinoma (NPC).

In some embodiments, said subject has been administrated an immune checkpoint inhibitor.

In some embodiments, said subject was not substantially responsive to said immune checkpoint inhibitor.

In some embodiments, said immune checkpoint inhibitor is selected from a group consisting of: PD-L1 inhibitor, PD-1 inhibitor and CTLA4 inhibitor.

In some embodiments, said subject has been administrated chemotherapy, chemoradiation, CTL cell therapy, EGFR tyrosine kinase inhibitors (TKIs), and/or angiogenesis inhibitors.

In some embodiments, said chemotherapy comprises first chemotherapy and/or second line chemotherapy.

In some embodiments, said second line chemotherapy comprises paclitaxel, docetaxel, capecitabine and/or 5-FU.

In some embodiments, said tumor is selected from a group consisting of advanced NSCLC without EGFR mutation or ALK fusions, NSCLC with EGFR Exon 20 insertion mutation, NPC with positive PD-L1 expression and locally advanced inoperable or metastatic TNBC.

In some embodiments, said dimer is administrated in combination with a chemotherapy agent.

In some embodiments, said chemotherapy agent comprises platinum doublets and/or paclitaxel.

In some embodiments, said chemotherapy agent comprises cisplatin, gemcitabine and/or platinum doublets.

In some embodiments, said dose of said dimer is 1 mg/kg to 5 mg/kg.

In some embodiments, said dose of said dimer is 1 mg/kg to 3 mg/kg.

In some embodiments, said dose of said dimer is 3 mg/kg to 5 mg/kg.

In some embodiments, said dimer is administrated once every two weeks or once every three weeks.

In some embodiments, said dimer is administrated by intravenous administration.

In another aspect, the present disclosure provides a use of the dimer of present disclosure in combination with a platinum-based agent of present disclosure in the preparation of a medicament for treating a tumor in a subject in need thereof.

In some embodiments, said tumor is selected from a group consisting of a solid tumor and a hematologic tumor.

In some embodiments, said tumor comprises NSCLC and/or breast cancer.

In some embodiments, said subject has been administrated EGFR tyrosine kinase inhibitors (TKIs).

In some embodiments, said tumor is selected from a group consisting of squamous and non-squamous NSCLC and Triple-negative breast cancer (TNBC).

In some embodiments, said tumor is selected from a group consisting of NSCLC with EGFR Exon 20 insertion mutation and locally advanced inoperable or metastatic TNBC.

In some embodiments, said dimer is administrated at a dosing frequency of four times a week, twice a week, once a week, once every two weeks, once every three weeks, once every four weeks, once every five weeks, once every six weeks, once every eight weeks or once every twelve weeks.

In some embodiments, said platinum-based agent is administrated at a dosing frequency of four times a week, twice a week, once a week, once every two weeks, once every three weeks, once every four weeks, once every five weeks, once every six weeks, once every eight weeks or once every twelve weeks.

In some embodiments, said dimer is administrated intravenously, intramuscularly, subcutaneously, topically, orally, transdermally, intraperitoneally, intraorbitally, by implantation, by inhalation, intrathecally, intraventricularly, or intranasally.

In some embodiments, said platinum-based agent is administrated intravenously, intramuscularly, subcutaneously, topically, orally, transdermally, intraperitoneally, intraorbitally, by implantation, by inhalation, intrathecally, intraventricularly, or intranasally.

In some embodiments, said dimer is administrated at dose of 0.01 mg/kg to 100 mg/kg.

In some embodiments, said chemotherapy agent is administrated at dose of 0.01 mg/kg to 100 mg/kg.

In another aspect, the present disclosure provides a kit comprises the dimer of present disclosure in combination with a chemotherapy agent of present disclosure.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are employed, and the accompanying drawings (also "figure" and "FIG." herein), of which:

DETAILED DESCRIPTION

Figure 1:
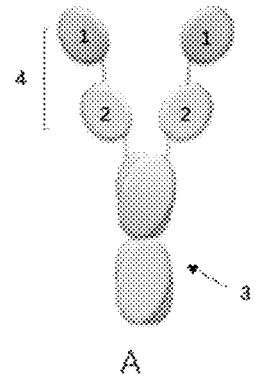
FIG. 1 illustrates examples of the dimers of the present disclosure.
Figure 1:
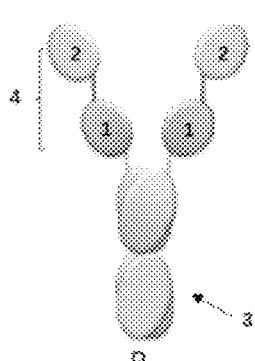

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "homology," "homologous" or "sequence identity," as used herein, generally refers to sequence similarity or interchangeability between two or more polynucleotide sequences or between two or more polypeptide sequences. When using a program (e.g. Emboss Needle or BestFit) to determine sequence identity, similarity or homology between two different amino acid sequences, the default settings may be used, or an appropriate scoring matrix, such as blosum45 or blosum80, may be selected to optimize identity, similarity or homology scores. In some embodiments, polynucleotides that are homologous are those which hybridize under stringent conditions and have at least 60%, at least 65%, at least 70%, at least 80%, at least 90%, at least 95%, at least 97%, at least 98%, at least 99%, and even 100% sequence identity with a reference sequence. Polypeptides that are homologous may have a sequence identity of at least 80%, or at least 90%, or at least 95%, or at least 97%, or at least 98%, or at least 99% with each other when sequences of comparable length are optimally aligned.

The term "percent (%) sequence identity," as used in the context of polypeptide sequences identified herein, generally refers to the percentage of amino acid residues or nucleotides in a query sequence that are identical with the amino acid residues or nucleotides of a second, reference polypeptide sequence or a portion thereof, after aligning the sequences and introducing gaps, if necessary, to achieve the maximum percent sequence identity, and not considering any conservative substitutions as part of the sequence identity. Alignment for purposes of determining percent amino acid/nucleotide sequence identity can be achieved in various ways that are within the skill in the art, for instance, using publicly available computer software such as BLAST, BLAST-2, ALIGN, NEEDLE or Megalign (DNASTAR) software. Those skilled in the art can determine appropriate parameters for measuring alignment, including any algorithms needed to achieve maximal alignment over the full length of the sequences being compared. Percent identity may be measured over the length of an entire defined polypeptide/polynucleotide sequence, or may be measured over a shorter length, for example, over the length of a fragment taken from a larger, defined polypeptide/polynucleotide sequence. It is understood that any fragment length supported by the sequences shown herein, in the tables, figures or Sequence Listing, may be used to describe a length over which percentage identity may be measured.

The term "bispecific antibody," as used herein, generally refers to an antibody having the capacity to bind to two distinct epitopes either on a single antigen or two different antigens.

The term "PD-L1," as used herein, generally refers to the Programmed Death Ligand 1 protein, its functional variant and/or its functional fragments. PD-L1 is also known as cluster of differentiation 274 (CD274) or B7 homolog 1 (B7-H1), and is a protein encoded by the CD274 gene (in human). PD-L1 binds to its receptor, programmed cell death protein 1 (PD-1), which is expressed in activated T cells, B cells, and macrophages (Ishida et al., 1992 EMBO J, 11:3887-3395; Okazaki et al., Autoimmune dilated cardiomyopathy in PD-1 receptor-deficient mice. *Science,* 2001; 291: 319-22). The complexation of PD-L1 and PD-1 exerts immunosuppressive effects by inhibiting T cell proliferation and cytokine production of TL-2 and IFN-7 (Freeman et al., Engagement of PD-1 immunoinhibitory receptor by a novel B7 family member leads to negative regulation of lymphocyte activation, *J. Exp. Med.* 2000, 192:1027-1034; Carter et al., PD-1: PD-L inhibitory pathway affects both CD4(+) and CD8(+) T cells and is overcome by IL-2. *Eur. J. Immunol.* 2002, 32:634-643). For example, the term "PD-L1" may comprise a polypeptide or a fragment thereof having at least about 85% amino acid sequence identity to NCBI Accession No. Q9NZQ7 and that specifically binds PD1. The term PD-L1 includes the entire PD-L1 ligand, soluble PD-L1 ligand, and fusion proteins comprising a functionally active portion of PD-L1 ligand covalently linked to a second moiety, e.g., a protein domain. Also included within the definition of PD-L1 are variants which vary in amino acid sequence from naturally occurring PD-L1 but which retain the ability to specifically bind to the receptor PD1. Further included within the definition of PD-L1 are variants which enhance the biological activity of PD1. PD-L1 sequences are known in the art and are provided, for example, at GenBank Accession Numbers 29126. The term "PD-L1" as used herein includes human PD-L1 (hPD-L1), variants, isoforms, and species homologs of hPD-L1, and analogs having at least one common epitope with hPD-L1. For example, the term "PD-L1" also encompasses PD-L1 from other species, such as other mammals, for example, rat, mouse, rabbit, non-human primate, pig, or bovine. The complete hPD-L1 sequence can be found under GenBank Accession No. 29126.

The term "N-terminal IgV domain of human PD-L1," as used herein, generally refers to an extracellular domain of human PD-L1 located in its N-terminus. The term "N-terminal IgV domain of human PD-L1" may also refer to epitopes within said domain. The N-terminal IgV domain of the human PD-L1 protein (including the signal peptide) may comprise an amino acid sequence as set forth in SEQ ID NO: 64.

The term "CTLA4," as used herein, generally refers to the Cytotoxic T-Lymphocyte-Associated protein 4, its functional variant and/or its functional fragments. CTLA4 is an immunoinhibitory receptor belonging to the CD28 family. CTLA4 is expressed exclusively on T cells (CD $4^+$ and CD $8^+$ cells) in vivo, and binds to two ligands, CD80 and CD86 (also called B7-1 and B7-2, respectively). For example, the term "CTLA4" may comprise a polypeptide or a fragment thereof having at least about 85% amino acid sequence identity to NCBI Accession No. AAL07473.1 and that specifically binds to CD80 and/or CD86. The term "CTLA4" includes the entire CTLA4 receptor, its extracellular domain, and fusion proteins comprising a functionally active portion of CTLA4 covalently linked to a second moiety, e.g., a protein domain. Also included within the definition of CTLA4 are variants which vary in amino acid sequence from naturally occurring CTLA4 but which retain the ability to specifically bind to the ligand CD80 and/or CD86. CTLA4 sequences are known in the art and are provided, for example, at GenBank Accession No. 1493. The term "CTLA4" as used herein includes human CTLA4 (hCTLA4), variants, isoforms, and species homologs of hCTLA4, and analogs having at least one common epitope with hCTLA4. For example, the term "CTLA4" also encompasses CTLA4 from other species, such as other mammals, for example, rat, mouse, rabbit, non-human primate, pig, or bovine. The complete hCTLA4 sequence can be found under GenBank Accession No. 1493.

The term "antibody Fc subunit," as used herein, generally refers to a component of an antibody Fc domain. For example, an antibody Fc domain may be formed by two or more members, and each member may be considered as one Fc subunit. The term "Fc domain," as used herein, generally refers to an Fc part or Fc fragment of an antibody heavy chain. For example, it may refer to the carboxyl terminal portion of an immunoglobulin heavy chain constant region, or an analog or portion thereof capable of binding an Fc receptor. As is known, each immunoglobulin heavy chain constant region comprises four or five domains. The domains are named sequentially as follows: CH1-hinge-CH2-CH3(-CH4). CH4 is present in IgM, which has no hinge region. The Fc domain or Fc subunit useful in the present disclosure may comprise a CH3 domain. For example, the Fc domain or Fc subunit may comprise a CH2 domain and a CH3 domain. In some embodiments, the Fc domain or Fc subunit may also comprise an immunoglobulin hinge region. For example, the Fc domain or Fc subunit may comprise or consist of, from N-terminus to C-terminus, a CH2 domain and a CH3 domain. In another example, the Fc domain or Fc subunit may comprise or consist of, from N-terminus to C-terminus, an immunoglobulin hinge region, a CH2 domain and a CH3 domain. Amino acid residue positions within the Fc domain or Fc subunit may be determined according to Kabat, E. A. et al., (1991) Sequences of Proteins of Immunological Interest, 5th ed., NIH Publication No. 91-3242.

The term "Fc domain", as used herein, generally refers to a C-terminal region of an immunoglobulin heavy chain, including native-sequence Fc regions and variant Fc regions. Although the boundaries of the Fc region of an immuno-globulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include human IgG1, IgG2 (IgG2A, IgG2B), IgG3 and IgG4.

Unless indicated otherwise herein, the numbering of the residues in an immunoglobulin chain is that of the EU index as in Kabat et al., Sequences of Proteins of Immunological Interest, $5^{th}$ Ed. Public Health Service, National Institutes of Health, Bethesda, Md. (1991). The "EU index as in Kabat" refers to the residue numbering of the human IgG1 EU antibody.

The term "dimer," as used herein, generally refers to a macromolecular complex formed by two, usually non-covalently bound, monomer units. Each monomer unit may be a macromolecule, such as a polypeptide chain or a polynucleotide. The term "homodimer," as used herein, generally refers to a dimer composed of or formed by two substantially identical monomers, such as two substantially identical polypeptide chains. In some cases, the two monomers of a homodimer may be different at one or more regions or positions, however, such difference does not cause significant alteration in the function or structure of the monomer. For example, one of ordinary skills in the art would consider the difference between the two monomers to be of little or no biological and/or statistical significance within the context of the biological characteristic considered in the present disclosure. The structural/compositional difference between said two monomers may be, for example, less than about 50%, less than about 40%, less than about 30%, less than about 20%, less than about 10%, less than about 5%, or less.

The term "fused" or "fusion," as used herein, generally refers the covalent linkage between two polypeptides. The polypeptides are typically joined via a peptide bond, either directly to each other or via an amino acid linker. Optionally, the peptides can be joined via non-peptide covalent linkages known to those of skill in the art.

The term "fusion protein" as used herein, generally refers to a polypeptide that comprises, or alternatively consists of, an amino acid sequence of a polypeptide fused directly or indirectly (e.g., via a linker) to an amino acid sequence of a heterologous polypeptide (i.e., a polypeptide unrelated to the former polypeptide or the domain thereof).

The term "immunoglobulin single variable domain (ISVD)," as used herein, generally refers to antigen-binding domains or fragments such as VHH domains or VH or VL domains, respectively. The terms antigen-binding molecules or antigen-binding protein are used interchangeably and include also the term Nanobodies. The immunoglobulin single variable domains further are light chain variable domain sequences (e.g., a VL-sequence), or heavy chain variable domain sequences (e.g., a VH-sequence); more specifically, they can be heavy chain variable domain sequences that are derived from a conventional four-chain antibody or heavy chain variable domain sequences that are derived from a heavy chain antibody. Accordingly, the immunoglobulin single variable domains can be domain antibodies, or immunoglobulin sequences that are suitable for use as domain antibodies, single domain antibodies, or immunoglobulin sequences that are suitable for use as single domain antibodies, "dAbs," or immunoglobulin sequences that are suitable for use as dAbs, or Nanobodies, including but not limited to VHH sequences. The immunoglobulin single variable domain includes fully human, humanized, otherwise sequence optimized or chimeric immunoglobulin sequences. The immunoglobulin single variable domain and structure of an immunoglobulin single variable domain can be considered-without however being limited thereto—to be comprised of four framework regions or "FRs," which are referred to in the art and herein as "Framework region 1" or "FR1"; as "Framework region 2" or "FR2"; as "Framework region 3" or "FR3"; and as "Framework region 4" or "FR4," respectively; which framework regions are interrupted by three complementary determining regions or "CDRs," which are referred to in the art as "Complementarity Determining Region 1" or "CDR1"; as "Complementarity Determining Region 2" or "CDR2"; and as "Complementarity Determining Region 3" or "CDR3," respectively.

The term "humanized," as used herein, generally refers to an antibody or a fragment thereof, in which some, most or all of the amino acids outside the CDR domains of a non-human antibody are replaced with corresponding amino acids derived from human immunoglobulins. For example, in a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to its specific antigen/epitope. A humanized antibody may retain an antigenic specificity similar to that of the original antibody.

The term "epitope" or "antigenic determinant," as used herein, generally refers to a site on an antigen to which an antibody bind. Epitopes can be formed both from contiguous amino acids (linear epitope) or noncontiguous amino acids juxtaposed by tertiary folding of a protein (conformational epitopes). Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The term "conformational epitope," as used herein, generally refers to noncontiguous amino acid residues of the antigen (such as the PD-L1 antigen) that are juxtaposed by tertiary folding of a protein. These noncontiguous amino acid residues may come together on the surface when the polypeptide chain folds to form the native protein. The conformation epitope contains, but is not limited to, the functional epitope.

The term "functional epitope," as used herein, generally refers to amino acid residues of an antigen that contribute energetically to the binding of an antibody, i.e. forming an "energetic epitope". Mutation of any one of the energetically contributing residues of the antigen to alanine will disrupt the binding of the antibody such that the relative $K_D$ ratio ($K_D$ mutant/$K_D$ wildtype) of the antibody may be e.g., greater than 2 folds, such as greater than 3 folds, greater than 4 folds, greater than 6 folds, greater than 10 folds, greater than 20 folds, greater than 30 folds, greater than 40 folds, greater than 50 folds, greater than 60 folds, greater than 70 folds, greater than 80 folds, greater than 90 folds, greater than 100 folds, greater than 150 folds, greater than 200 folds, or more.

The term "extracellular domain," as used herein, generally refers to part of a protein (e.g., a membrane protein, such as a receptor) protruding from the outer membrane of a cell organelle and/or a cell. If the polypeptide chain crosses the bilayer several times, the extracellular domain comprises loops entwined through the membrane. An extracellular domain may recognize and respond to a specific ligand.

The term "linker," as used herein, generally refers to a synthetic amino acid sequence that connects or links two polypeptide sequences, e.g., that links two polypeptide domains. A linker may connect two amino acid sequences via peptide bonds. In some embodiments, a linker of the present disclosure connects a biologically active moiety to a second moiety in a linear sequence. For example, a peptide linker may be non-immunogenic and flexible, such as those comprising serine and glycine sequences or repeats of Ala-Ala-Ala. Depending on the particular construct of the dimer, a peptide linker may comprise, e.g., 3-30 (such as at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30) amino acid residues.

The term "N-terminal" may be used interchangeably with "N-terminus," and as used herein, they generally refer to the amino terminus/end of a polypeptide chain.

The term "C-terminal" may be used interchangeably with "C-terminus," and as used herein, they generally refer to the carboxyl terminus/end of a polypeptide chain.

The term "tumor," as used herein, generally refers to tumor growth or metastasis, by any clinically measurable degree. The tumor can be a solid tumor, a hematologic tumor, or a lymphoma. For example, the tumor may be selected from lung cancer (such as non-small-cell lung cancer), breast cancer (such as Triple-Negative Breast Cancer), kidney cancer (such as renal cell carcinoma), melanoma, cervical cancer, uterus cancer, pancreatic cancer, peritoneal carcinoma, ovarian cancer and colon cancer. The tumor may be advanced or metastatic tumor. The tumor may be selected from a group consisting of NSCLC, melanoma, esophageal squamous cell carcinoma (ESCC), NPC and breast cancer (for example, Triple-negative breast cancer (TNBC)).

The term "subject," as used herein, generally refers to a human or non-human animal, including, but not limited to, a cat, dog, horse, pig, cow, sheep, goat, rabbit, mouse, rat, or monkey. In some embodiments, the subject is a human. In some embodiments, the subject is resistant to the therapy of an immune checkpoint inhibitor.

The term "about," as used herein, generally refers to a variation that is within a range of normal tolerance in the art, and generally means within ±10%, such as within 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The terms "co-administration", "co-administered" or "co-administering", as used herein, generally refers that one agent (e.g. a dimer) is administered with another agent (e.g. an immune check point inhibitor). The administration of one agent can be carried out either as one single formulation or as two separate formulations (e.g., one for the dimer and one for the immune check point inhibitor). The co-administration can be simultaneous or sequential in either order.

The term "treating" as used herein, generally refers to having a therapeutic effect and at least partially alleviating or abrogating an abnormal condition in the organism. The term "treating" refers to ameliorating a symptom of a medicament condition in a group of patients to whom the medicament is administered relative to a control group that does not receive the medicament. The effect of the treatment can be monitored by measuring a change or an absence of a change in cell phenotype, a change or an absence of a change in cell proliferation, a change or an absence of a change in the tumor size, a change or an absence of a change in tumor size, a change or an absence of a change in a progressive disease, a change or an absence of a change in a stable disease, a change or an absence of a change in a disease control rate, a change or an absence of a change in a partial response. The term "treating" or "treatment" does not necessarily mean total cure. Any alleviation of any undesired symptom of the disease to any extent or the slowing down of the progress of the disease can be considered treatment. Furthermore, treatment may include acts which may worsen the patient's overall feeling of well being or appearance.

The term "specifically binds to" or "is specific for", as used herein, generally refers to measurable and reproducible inter actions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant ($K_D$) of $<1\times10^{-6}$ M, $<1\times10^{-7}$ M, $<1\times10^{-8}$ M, $<1\times10^{-9}$ M, or $<1\times10^{-10}$ M. In certain embodiments, an antibody specifically binds to an epitope on a protein that is conserved among the protein from different species. In another embodiment, specific binding can include, but does not require exclusive binding.

The term "antibody," as used herein, generally refers to an immunoglobulin or a fragment or a derivative thereof, and encompasses any polypeptide comprising an antigen-binding site, regardless whether it is produced in vitro or in vivo. The term includes, but is not limited to, polyclonal, monoclonal, monospecific, polyspecific, non-specific, humanized, single-chain, chimeric, synthetic, recombinant, hybrid, mutated, and grafted antibodies. Unless otherwise modified by the term "intact," as in "intact antibodies," for the purposes of this disclosure, the term "antibody" also includes antibody fragments such as Fab, F(ab')₂, Fv, scFv, Fd, dAb, and other antibody fragments that retain antigen-binding function, i.e., the ability to bind, for example, CTLA-4, or PD-L1 specifically. Typically, such fragments would comprise an antigen-binding domain.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for and F isotypes. Each L chain has at the N-terminus, a variable domain (VL) followed by a constant domain at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see e.g., Basic and Clinical Immunology, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2A, IgG2B, IgG3, IgG4, IgA1 and IgK1.

The term "polypeptide chain," as used herein, generally refers to a macromolecule comprising two or more covalently connected peptides. The peptides within a polypeptide chain may be connected with each other via a peptide bond. Each polypeptide chain may comprise one N-terminus or amino terminus and one C-terminus or carboxy terminus.

The term "CD80," as used herein, generally refers to a ligand for CD28/CTLA4, also known as B7.1, its functional variant and/or its functional fragments. CD80 is generally expressed on the surface of professional antigen presenting cells (APC). For example, the term "CD80" may comprise a polypeptide or a fragment thereof having at least about 85% amino acid sequence identity to NCBI Accession No. P33681 and that specifically binds CTLA4. Also included within the definition of CD80 are variants which vary in amino acid sequence from naturally occurring CD80 but which retain the ability to specifically bind to CTLA4. Further included within the definition of CD80 are variants which enhance the biological activity of CTLA4. CD80 sequences are known in the art and are provided, for example, at GenBank Accession Numbers P33681. The term "CD80" as used herein includes human CD80 (hCD80), variants, isoforms, and species homologs of hCD80, and analogs having at least one common epitope with hCD80. For example, the term "CD80" also encompasses CD80 from other species, such as other mammals, for example, rat, mouse, rabbit, non-human primate, pig, or bovine. The complete hCD80 sequence can be found under GenBank Accession No. P33681.

The term "CD86," as used herein, generally refers to a ligand for CD28/CTLA4, also known as B7.2, its functional variant and/or its functional fragments. CD86 is generally expressed on the surface of professional antigen presenting cells (APC). For example, the term "CD86" may comprise a polypeptide or a fragment thereof having at least about 85% amino acid sequence identity to NCBI Accession No. P42081 and that specifically binds CTLA4. Also included within the definition of CD86 are variants which vary in amino acid sequence from naturally occurring CD86 but which retain the ability to specifically bind to CTLA4. Further included within the definition of CD86 are variants which enhance the biological activity of CTLA4. CD86 sequences are known in the art and are provided, for example, at GenBank Accession Numbers U04343. The term "CD86" as used herein includes human CD86 (hCD86), variants, isoforms, and species homologs of hCD86, and analogs having at least one common epitope with hCD86. For example, the term "CD86" also encompasses CD86 from other species, such as other mammals, for example, rat, mouse, rabbit, non-human primate, pig, or bovine. The complete hCD86 sequence can be found under GenBank Accession No. U04343.

The term "PD1," as used herein, generally refers to programmed death-1 receptor, also known as CD279, its functional variant and/or its functional fragments. PD1 is generally expressed on T cells, B cells, natural killer T cells, activated monocytes and dendritic cells (DCs). PD1 may bind to its ligands PD-L1 and PD-L2. For example, the term "PD1" may comprise a polypeptide or a fragment thereof having at least about 85% amino acid sequence identity to NCBI Accession No P42081 and that specifically binds PD-L1. Also included within the definition of PD1 are variants which vary in amino acid sequence from naturally occurring PD1 but which retain the ability to specifically bind to PD-L1. Further included within the definition of PD1 are variants which enhance the biological activity of PD-L1. PD1 sequences are known in the art and are provided, for example, at GenBank Accession Number Q15116.3. The term "PD1" as used herein includes human PD1 (hPD1), variants, isoforms, and species homologs of hPD1, and analogs having at least one common epitope with hPD1. For example, the term "PD1" also encompasses PD1 from other species, such as other mammals, for example, rat, mouse, rabbit, non-human primate, pig, or bovine. The complete hPD1 sequence can be found under GenBank Accession No. Q15116.3.

The term "blocking", as used herein, generally refers to an inhibition or reduction of the binding activity between a molecule and its specific binding partner, such as between a ligand and its specific receptor.

The term "blocking antibody" and "antagonist antibody" are used interchangeably herein and generally refers to an antibody that inhibits or reduces a biological activity of the antigen it binds to. In some embodiments, blocking antibodies or antagonist antibodies substantially or completely inhibit the biological activity of the antigen. The PD-L1 specific ISVD or the CTLA4 specific ISVD of the present disclosure may be blocking or antagonistic ISVDs. For example, the PD-L1 specific ISVD of the present disclosure may block the interaction between PD-L1 and its receptor PD-1, and thus the signaling through PD-1 so as to restore a functional response by T-cells from a dysfunctional state to antigen stimulation. The CTLA4 specific ISVD of the present disclosure may block the interaction between CTLA4 and CD80/CD86, and thus the signaling through CTLA4 so as to restore a functional response by T-cells from a dysfunctional state to antigen stimulation.

The term "cross-competes for binding", "cross-competition", "cross-block", "cross-blocked" and "cross-blocking" are used interchangeably herein and generally refers to the ability of an antibody or fragment thereof to interfere with the binding directly or indirectly through allosteric modulation of another antibody of the invention (e.g., the PD-L1 specific ISVD or the CTLA4 specific ISVD of the present disclosure) to the target/antigen (e.g., PD-L1 or CTLA4, respectively). The extent to which an antibody or fragment thereof is able to interfere with the binding of another to the target, and therefore whether it can be said to cross-block or cross-compete according to the invention, can be determined using competition binding assays. One particularly suitable quantitative cross-competition assay uses a FACS-based or an AlphaScreen-based approach to measure competition between the labelled (e.g. His tagged, biotinylated or radio-active labelled) an antibody or fragment thereof and the other an antibody or fragment thereof in terms of their binding to the target. In general, a cross-competing antibody or fragment thereof is for example one which will bind to the target in the cross-competition assay such that, during the assay and in the presence of a second antibody or fragment thereof, the recorded displacement of the immunoglobulin single variable domain or polypeptide according to the invention is up to 100% (e.g. in FACS based competition assay) of the maximum theoretical displacement (e.g. displacement by cold (e.g. unlabeled) antibody or fragment thereof that needs to be cross-blocked) by the to be tested potentially cross-blocking antibody or fragment thereof that is present in a given amount. Preferably, cross-competing antibodies or fragments thereof have a recorded displacement that is between 10% and 100%, such as between 50% to 100%.

The term "substantially reduced," or "substantially different," as used herein, generally refers to a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., $K_D$ values). The difference between said two values is, for example, greater than about 10%, greater than about 20%, greater than about 30%, greater than about 40%, and/or greater than about 50% as a function of the value for the reference/comparator molecule.

The term "substantially similar" or "substantially the same," as used herein, generally refers to a sufficiently high degree of similarity between two numeric values (for example, one associated with a molecule of the present disclosure and the other associated with a reference/comparator molecule), such that one of skill in the art would consider the difference between the two values to be of little or no biological and/or statistical significance within the context of the biological characteristic measured by said values {e.g., $K_D$ values). The difference between said two values is, for example, less than about 50%, less than about 40%, less than about 30%, less than about 20%, and/or less than about 10% as a function of the reference/comparator value.

The term "variable region" or "variable domain" of an antibody, as used herein, generally refers to the amino-terminal domains of the heavy or light chain of an antibody. The variable domains of the heavy chain and light chain may be referred to as "VH" and "VL", respectively. These domains are generally the most variable parts of the antibody (relative to other antibodies of the same class) and contain the antigen binding sites.

The term "variable", as used herein, generally refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (CDRs or HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies (see Kabat et al, Sequences of Immunological Interest, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "CDR," "HVR," or "HV," as used herein, generally refers to the regions of an antibody variable domain which are hypervariable in sequence and/or form structurally defined loops. Generally, antibodies comprise six CDRs; three in the VH (HCDR1, HCDR2, HCDR3), and three in the VL (LCDR1, LCDR2, LCDR3). The ISVD of the present disclosure may only comprise 3 CDRs (e.g., in the VH, HCDR1, HCDR2 and HCDR3). In native antibodies, HCDR3 and LCDR3 display the most diversity of the six CDRs, and HCDR3 in particular is believed to play a unique role in conferring fine specificity to antibodies. See, e.g., Xu et al, Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al, Nature Struct. Biol. 3:733-736 (1996).

A number of CDR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk, J. Mol. Biol. 196:901-917 (1987)). The AbM CDRs represent a compromise between the Kabat HVRs and Chothia structural loops, and are used by Oxford Molecular's AbM antibody modeling software.

The "contact" CDRs are based on an analysis of the available complex crystal structures. The residues from each of these CDRs are noted in Table 1:

89-96 (LCDR3) in the VL and 26-35 (HCDR1), 50-65 or 49-65 (HCDR2) and 93-102, 94-102, or 95-102 (HCDR3) in the VH. The variable domain residues are numbered according to Kabat et al., supra, for each of these definitions.

The expression "variable-domain residue-numbering as in Kabat" or "amino-acid-position numbering as in Kabat," and variations thereof, generally refers to the numbering system used for heavy-chain variable domains or light-chain variable domains of the compilation of dimer/polypeptide chain in Kabat et al., supra. The Kabat numbering of residues may be determined for a given polypeptide by alignment at regions of homology of the sequence of the polypeptide with a "standard" Kabat numbered sequence.

"Framework" or "FR" residues are those variable-domain residues other than the CDR residues as herein defined. A "human consensus framework" or "acceptor human framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, 5th Ed. Public Health Service, National Institutes of Health, Bethesda, Md. (1991). Examples include for the VL, the subgroup may be subgroup kappa I, kappa II, kappa III or kappa IV as in Kabat et al, supra. Additionally, for the VH, the subgroup may be subgroup I, subgroup II, or subgroup III as in Kabat et al., supra. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain preexisting amino acid sequence changes. In some embodiments, the number of pre-existing amino acid changes are 10 or less, 9 or less, 8 or less, 7 or less, 6 or less, 5 or less, 4 or less, 3 or less, or 2 or less.

The term "not substantially responsive" generally used to describe with one or more conventional therapies (e.g. tumor treatment), such as chemotherapy, radiation therapy, surgery, hormonal therapy and/or biological therapy/immunotherapy, particularly a standard therapeutic regimen for the treatment of patients with the particular tumor, said method of treatment is not sufficient to cure the patient in the clinic, for example, the patients may still be susceptible to the treatment, so that these patients need additional effective therapy. This term is also used to describe a circumstance having respond to a treatment with side effect, relapse or resistance and the like. In some embodiments, "not substantially

TABLE 1

| Loop | Kabat | AbM | Chothia | Contact |
|---|---|---|---|---|
| LCDR1 | L24-L34 | L24-L34 | L26-L32 | L30-L36 |
| LCDR2 | L50-L56 | L50-L56 | L50-L52 | L46-L55 |
| LCDR3 | L89-L97 | L89-L97 | L91-L96 | L89-L96 |
| HCDR1(Kabat Numbering) | H31-H35B | H26-H35B | H26-H32 | H30-H35B |
| HCDR1(Chothia Numbering) | H31-H35 | H26-H35 | H26-H32 | H30-H35 |
| HCDR2 | H50-H65 | H50-H58 | H53-H55 | H47-H58 |
| HCDR3 | H95-H102 | H95-H102 | H96-H101 | H93-H101 |

CDRs may comprise "extended CDRs" as follows: 24-36 or 24-34 (LCDR1), 46-56 or 50-56 (LCDR2) and 89-97 or responsive" is meant that a patient is either refractory to, intolerant to, or have refused, standard therapy for treatment of a tumor, including patients may demonstrate objective evidence of disease progression despite treatment with an immune checkpoint inhibitor.

In the present disclosure, an amino acid sequence or nucleotide sequence as set forth in a specific SEQ ID NO. also encompasses homologs or variants thereof having substantially the same function/property thereto. For example, a sequence having at least 90%, at least 91%, at least 92%, at least 93%, at least 94%, at least 95%, at least 96%, at least 97%, at least 98%, at least 99%, or higher sequence identity thereto; and/or a variant having one or more (e.g., a few, such as 1-10, 1-9, 1-8, 1-7, 1-6, 1-5, 1-4, 1-3, 1-2) amino acid or nucleotide addition, deletion or substitution.

Dimers

In one aspect, the present disclosure provides use of a dimer in the preparation of a medicament for treating a tumor in a subject in need thereof, and said dimer formed by two polypeptide chains, with each of said two polypeptide chains comprising an antibody Fc subunit, wherein said dimer comprises two or more immunoglobulin single variable domains (ISVDs), at least one of said ISVDs is specific for PD-L1, and at least one of said ISVDs is specific for CTLA4.

In another aspect, the present disclosure provides a method for treating a tumor in a subject in need thereof, comprising administering to said subject an effective amount of the dimer.

In some embodiments, the dimer may be formed by two polypeptide chains, with each of the two polypeptide chains comprising an antibody Fc subunit. For example, the dimer may consist of two polypeptide chains with each polypeptide chain comprising an antibody Fc subunit, and the antibody Fc subunit of one polypeptide chain may associate with the antibody Fc subunit of the other polypeptide chain to form the dimer. In an example, the two polypeptide chains of the dimer do not fuse (e.g., via a peptide linker or by a peptide bond) with each other to become one single polypeptide chain.

The dimer may comprise two or more immunoglobulin single variable domains (ISVDs). For example, one polypeptide chain of the dimer may comprise two or more ISVDs, and the other polypeptide chain of the dimer does not comprise any ISVD. In another example, each of the two polypeptide chains may comprise one or more ISVDs. In yet another example, each of the two polypeptide chains may comprise two or more ISVDs.

At least one of the ISVDs may be specific for PD-L1, and at least one of the ISVDs may be specific for CTLA4. For example, one polypeptide chain of the dimer may comprise one or more ISVDs specific for PD-L1 and one or more ISVDs specific for CTLA4, and the other polypeptide chain of the dimer does not comprise any ISVD. In another example, one polypeptide chain of the dimer may comprise one or more ISVDs specific for PD-L1, and the other polypeptide chain of the dimer may comprise one or more ISVDs specific for CTLA4. In another example, one polypeptide chain of the dimer may comprise one or more ISVDs specific for PD-L1 and one or more ISVDs specific for CTLA4, and the other polypeptide chain of the dimer may comprise one or more ISVDs specific for PD-L1 and/or one or more ISVDs specific for CTLA4.

The one or more ISVDs specific for PD-L1 may be identical or different. The one or more ISVDs specific for CTLA4 may be identical or different.

In some cases, the ISVD specific for PD-L1 does not comprise any antibody light chain CDR. In some cases, the ISVD specific for PD-L1 does not comprise any antibody light chain variable region. In some cases, the ISVD specific for PD-L1 does not comprise any antibody light chain or any fragment thereof. In some cases, the ISVD specific for PD-L1 comprises at least heavy chain CDR3. In some cases, the ISVD specific for PD-L1 comprises heavy chain CDR1. In some cases, the ISVD specific for PD-L1 comprises heavy chain CDR2. In some cases, the ISVD specific for PD-L1 comprises a heavy chain variable region. In some cases, the ISVD specific for PD-L1 is an anti-PD-L1 VHH. The ISVD specific for PD-L1 may be humanized.

In some cases, the ISVD specific for CTLA4 does not comprise any antibody light chain CDR. In some cases, the ISVD specific for CTLA4 does not comprise any antibody light chain variable region. In some cases, the ISVD specific for CTLA4 does not comprise any antibody light chain or any fragment thereof. In some cases, the ISVD specific for CTLA4 comprises at least heavy chain CDR3. In some cases, the ISVD specific for CTLA4 comprises heavy chain CDR1. In some cases, the ISVD specific for CTLA4 comprises heavy chain CDR2. In some cases, the ISVD specific for CTLA4 comprises a heavy chain variable region. In some cases, the ISVD specific for CTLA4 is an anti-CTLA4 VHH. The ISVD specific for CTLA4 may be humanized.

In some cases, at least one of the two polypeptide chains may comprise both an ISVD specific for PD-L1 and an ISVD specific for CTLA4. For example, one of the two polypeptide chains may comprise one or more ISVDs specific for PD-L1 and one or more ISVDs specific for CTLA4. In another example, each of the two polypeptide chains may comprise one or more ISVDs specific for PD-L1 and one or more ISVDs specific for CTLA4.

For one or both of the two polypeptide chains, the ISVD specific for PD-L1 may be fused to the ISVD specific for CTLA4, optionally via a linker. For example, in one or both of the two polypeptide chains, there may be one or more ISVDs specific for PD-L1, and one or more ISVDs specific for CTLA4. When two or more ISVDs specific for PD-L1 are present in a single polypeptide chain, they may be fused to each other (e.g., directly or via a peptide linker), and one or more of them may further be fused to one or more ISVDs specific for CTLA4. When two or more ISVDs specific for CTLA4 are present in a single polypeptide chain, they may be fused to each other (e.g., directly or via a peptide linker), and one or more of them may further be fused to one or more ISVDs specific for PD-L1. One or more linkers (e.g., peptide linker) may be present between any two ISVDs, for example, between two ISVDs specific for PD-L1, between two ISVDs specific for CTLA4, or between one ISVD specific from PD-L1 and one ISVD specific for CTLA4.

For one or both of the two polypeptide chains, the ISVD specific for PD-L1 may be fused to the ISVD specific for CTLA4, optionally via a linker; and the ISVD specific for CTLA4 may in turn be fused to the antibody Fc subunit, optionally via a linker. For example, in a single polypeptide chain, the ISVD specific for PD-L1 may be fused to the ISVD specific for CTLA4 directly (e.g., in frame) or via a linker, and the ISVD specific for CTLA4 may be fused to the antibody Fc subunit directly (e.g., in frame) or via a linker. When there are more than one ISVDs specific for PD-L1 and/or more than one ISVDs specific for CTLA4 in a single polypeptide chain, the ISVDs specific for PD-L1 and the ISVDs specific for CTLA4 may be fused directly or via a linker to each other according to any order, and at least one ISVD specific for CTLA4 may be fused to the antibody Fc subunit directly (e.g., in frame) or via a linker. For example, for one or both of the two polypeptide chains, C terminus of the ISVD specific for PD-L1 may be fused to N terminus of the ISVD specific for CTLA4, optionally via a linker; and C terminus of the ISVD specific for CTLA4 may be fused to N terminus of the antibody Fc subunit, optionally via a linker. For example, in a single polypeptide chain, C terminus of one of the ISVDs specific for PD-L1 may be fused to N terminus of one of the ISVDs specific for CTLA4, either directly (e.g., in frame) or via a linker, and C terminus of one of the ISVDs specific for CTLA4 may be fused to N terminus of the antibody Fc subunit, either directly (e.g., in frame) or via a linker. In an example, when there are more than one ISVDs specific for PD-L1 and/or more than one ISVDs specific for CTLA4 in a single polypeptide chain, the ISVDs specific for PD-L1 and the ISVDs specific for CTLA4 may be fused directly or via a linker to each other according to any order, however, C terminus of at least one ISVD specific for PD-L1 may be fused to N terminus of at least one ISVD specific for CTLA4, either directly (e.g., in frame) or via a linker, and C terminus of at least one ISVD specific for CTLA4 may be fused to N terminus of the antibody Fc subunit, either directly (e.g., in frame) or via a linker.

For one or both of the two polypeptide chains, the ISVD specific for CTLA4 may be fused to the ISVD specific for PD-L1, optionally via a linker; and the ISVD specific for PD-L1 may in turn be fused to the antibody Fc subunit, optionally via a linker. For example, in a single polypeptide chain, the ISVD specific for CTLA4 may be fused to the ISVD specific for PD-L1 directly (e.g., in frame) or via a linker, and the ISVD specific for PD-L1 may be fused to the antibody Fc subunit directly (e.g., in frame) or via a linker. When there are more than one ISVDs specific for PD-L1 and/or more than one ISVDs specific for CTLA4 in a single polypeptide chain, the ISVDs specific for PD-L1 and the ISVDs specific for CTLA4 may be fused directly or via a linker to each other according to any order, and at least one ISVD specific for PD-L1 may be fused to the antibody Fc subunit directly (e.g., in frame) or via a linker. For example, for one or both of the two polypeptide chains, C terminus of the ISVD specific for CTLA4 may be fused to N terminus of the ISVD specific for PD-L1, optionally via a linker; and C terminus of the ISVD specific for PD-L1 may be fused to N terminus of the antibody Fc subunit, optionally via a linker. For example, in a single polypeptide chain, C terminus of one of the ISVDs specific for CTLA4 may be fused to N terminus of one of the ISVDs specific for PD-L1, either directly (e.g., in frame) or via a linker, and C terminus of one of the ISVDs specific for PD-L1 may be fused to N terminus of the antibody Fc subunit, either directly (e.g., in frame) or via a linker. In an example, when there are more than one ISVDs specific for PD-L1 and/or more than one ISVDs specific for CTLA4 in a single polypeptide chain, the ISVDs specific for PD-L1 and the ISVDs specific for CTLA4 may be fused directly or via a linker to each other according to any order, however, C terminus of at least one ISVD specific for CTLA4 may be fused to N terminus of at least one ISVD specific for PD-L1, either directly (e.g., in frame) or via a linker, and C terminus of at least one ISVD specific for PD-L1 may be fused to N terminus of the antibody Fc subunit, either directly (e.g., in frame) or via a linker.

The linker (e.g., a peptide linker) employed in the present application (e.g., as comprised by the dimer of the present application) may be a synthetic amino acid sequence that connects or links two polypeptide sequences, e.g., via peptide bonds. For example, the peptide linker may comprise 1-10 amino acids (e.g., 1, 2, 3, 4, 5, 6, 7, 8, 9, 10 or more amino acids), 1-15 amino acids (e.g., 1-10, 11, 12, 13, 14 or 15 amino acids), 1-20 amino acids (e.g., 1-15, 16, 17, 18, 19, or 20 amino acids), 1-30 amino acids or more (e.g., 1-20, 21, 22, 23, 24, 25, 26, 27, 28, 29, 30 or more amino acids). For example, the peptide linker may comprise an amino acid sequence as set forth in any of SEQ ID NO: 33-34. For example, the peptide linker may comprise an amino acid sequence as set forth in SEQ ID NO: 33.

The antibody Fc subunit may be derived from an IgG Fc subunit. For example, the IgG may be selected from the group consisting of IgG1, IgG2, IgG3 and IgG4. In some embodiments, the IgG is a human IgG1, and the IgG Fc subunit is a human IgG1 Fc subunit. In some embodiments, the Fc subunit comprises an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 35, 38 and 39. For example, the Fc subunit may comprise an amino acid sequence having one or more (e.g., 1-2, 1-3, 1-4, 1-5, 1-6, 1-7, 1-8, 1-9, 1-10, or more) amino acid deletion, insertion and/or substitution in the amino acid sequence as set forth in any one of SEQ ID NO: 35, 38 and 39. For example, the Fc subunit may comprise an amino acid sequence having one or more (e.g., 1-2, 1-3, 1-4, 1-5, 1-6, 1-7, 1-8, 1-9, 1-10, or more) amino acid deletion, insertion and/or substitution in the amino acid sequence as set forth in any one of SEQ ID NO: 38 and 39.

In some embodiments, the Fc subunit may be a variant of the IgG Fc subunit (e.g., a variant of the human IgG1 Fc subunit). For example, the variant may comprise one or more amino acid mutations that enhance or reduce the ADCC or CDC activities. As another example, the variant may comprise one or more amino acid mutations that affect FcRn binding activity and/or the half-life of the molecule comprising the variant. As yet another example, the variant may comprise one or more amino acid mutations that affect an interaction (e.g., association) between two or more Fc subunits (or Fc monomers) and/or increase or decrease an efficiency of Fc heterodimer formation, for example, the variant may comprise one or more of the amino acid substitutions as described in CN102558355A, CN103388013A, CN105820251A, or CN106883297A, each of which is incorporated by reference herein.

The ISVD specific for PD-L1 may be capable of specifically binding to human PD-L1. For example, the ISVD specific for PD-L1 may be capable of specifically binding to an epitope in an extracellular domain of the human PD-L1. Such epitopes are known in the art, for example, as shown by Gang Hao et al., *J. Mol. Recognit.* 2015; 28: 269-276, Zhang et al., Oncotarget. 2017 Oct; 08 (52): 90215-90224, and Zhang et al., Cell Discov. 2017 Mar. 7; 3:17004.

For example, the ISVD specific for PD-L1 may be capable of binding to N-terminal IgV domain of human PD-L1. The N-terminal IgV domain of human PD-L1 (including the signal peptide) may comprise an amino acid sequence as set forth in SEQ ID NO: 64. In the present disclosure, the ISVD specific for PD-L1 may be capable of binding to residues I54, Y56, E58, Q66 and/or R113 of human PD-L1 N-terminal IgV domain. In a specific embodiment, the ISVD specific for PD-L1 is capable of binding to residues I54, Y56, E58, Q66 and R113 of human PD-L1 N-terminal IgV domain (e.g., amino acid residue I54, Y56, E58, Q66 and/or R113 of SEQ ID NO: 64). The ISVD specific for PD-L1 may be capable of further binding to residues D61, N63, V68, M115, S117, Y123 and/or R125 of human PD-L1 N-terminal IgV domain (e.g., amino acid residue D61, N63, V68, M115, S117, Y123 and/or R125 of SEQ ID NO: 64). In some cases, the ISVD specific for PD-L1 may be capable of binding to residues I54, Y56, E58, Q66, R113, D61, N63, V68, M115, S117, Y123 and/or R125 of human PD-L1 N-terminal IgV domain (e.g., amino acid residue I54, Y56, E58, Q66, R113, D61, N63, V68, M115, S117, Y123 and/or R125 of SEQ ID NO: 64). In some cases, the ISVD specific for PD-L1 is capable of binding to a conformational epitope of human PD-L1 N-terminal IgV domain, the conformational epitope may comprise residues I54, Y56, E58, Q66 and/or R113 of the human PD-L1 N-terminal IgV domain (e.g., amino acid residue I54, Y56, E58, Q66 and/or R113 of SEQ ID NO: 64). In some cases, the ISVD specific for PD-L1 is capable of binding to a conformational epitope of human PD-L1 N-terminal IgV domain, the conformational epitope may comprise residue I54, Y56, E58, Q66, R113, D61, N63, V68, M115, S117, Y123 and/or R125 of the human PD-L1 N-terminal IgV domain (e.g., amino acid residue I54, Y56, E58, Q66, R113, D61, N63, V68, M115, S117, Y123 and/or R125 of SEQ ID NO: 64).

The ISVDs specific for PD-L1 of the present disclosure (e.g., PD-L1 ISVD-9 and the humanized variants thereof) bind to the N-terminal IgV domain of human PD-L1. Taking PD-L1 ISVD-9 as an example, the residue Phe101 of PD-L1 ISVD-9 (SEQ ID NO: 6) interacts with Tyr56 of human PD-L1 N-terminal IgV domain, and when the Tyr56 of human PD-L1 N-terminal IgV domain was substituted by Ala, the binding affinity between PD-L1 ISVD-9 and PD-L1 was reduced by over 200 folds. When the Ile54 of human PD-L1 N-terminal IgV domain was substituted by Ala, the binding affinity between PD-L1 ISVD-9 and PD-L1 was reduced by about 40 folds. The residue Asp99 of PD-L1 ISVD-9 (SEQ ID NO: 6) interacts with Arg113 of human PD-L1 N-terminal IgV domain, and when the Arg113 of human PD-L1 N-terminal IgV domain was substituted by Ala, the binding affinity between PD-L1 ISVD-9 and PD-L1 was reduced by about 90 folds. The residue Ser100 of PD-L1 ISVD-9 (SEQ ID NO: 6) interacts with Glu58 of human PD-L1 N-terminal IgV domain, and when the Glu58 of human PD-L1 N-terminal IgV domain was substituted by Ala, the binding affinity between PD-L1 ISVD-9 and PD-L1 was reduced by about 25 folds. The residue Thr105 of PD-L1 ISVD-9 (SEQ ID NO: 6) interacts with Gln66 of human PD-L1 N-terminal IgV domain, and when the Gln66 of human PD-L1 N-terminal IgV domain was substituted by Ala, the binding affinity between PD-L1 ISVD-9 and PD-L1 was reduced by about 82 folds. In addition, residues D61, N63, V68, M115, S117, Y123 and R125 of human PD-L1 N-terminal IgV domain may be involved in the interaction between PD-L1 ISVD-9 and human PD-L1, substituting these residues with Ala resulted in a reduction of binding affinity by about 2-10 folds. These results are summarized in Table 2 below.

TABLE 2

Effects of Substitutions in human
PD-L1 for binding of PD-L1 ISVD-9

| Human PD-L1 mutation | $K_D$ (M) | $K_{D, mutant}/K_{D, WT}$ |
|---|---|---|
| WT | 5.92E−09 | 1 |
| I54A | 2.42E−07 | 40.9 |
| Y56A | 1.24E−06 | 209.5 |
| E58A | 1.49E−07 | 25.2 |
| D61A | 1.99E−08 | 3.4 |
| N63A | 2.30E−08 | 3.9 |

TABLE 2-continued

Effects of Substitutions in human
PD-L1 for binding of PD-L1 ISVD-9

| Human PD-L1 mutation | $K_D$ (M) | $K_{D, mutant}/K_{D, WT}$ |
|---|---|---|
| Q66A | 4.88E−07 | 82.4 |
| V68A | 2.76E−08 | 4.7 |
| R113A | 5.34E−07 | 90.2 |
| M115A | 5.51E−08 | 9.3 |
| S117A | 1.26E−08 | 2.1 |
| Y123A | 4.24E−08 | 7.2 |
| R125A | 2.97E−08 | 5.0 |

The ISVD specific for PD-L1 may be capable of blocking binding of PD-L1 to PD1. In some cases, the ISVD specific for PD-L1 may be capable of blocking binding of PD-L1 to CD80.

The ISVD specific for PD-L1 may cross-compete for binding to PD-L1 with a reference anti-PD-L1 antibody. The reference anti-PD-L1 antibody may comprise a heavy chain CDR3. The heavy chain CDR3 may comprise an amino acid sequence as set forth in DSFX$_1$X$_2$PTCX$_3$X$_4$X$_5$X$_6$SSGAFQY (SEQ ID NO: 1), wherein X$_1$ may be E or G; X$_2$ may be D or Y; X$_3$ may be T or P; X$_4$ may be L or G; X$_5$ may be V or P; and X$_6$ may be T or A. In some cases, the reference anti-PD-L1 antibody may comprise a heavy chain CDR3 comprising an amino acid sequence as set forth in any one of SEQ ID NO: 5 and 9. The reference anti-PD-L1 antibody may also comprise a heavy chain CDR1. The heavy chain CDR1 may comprise an amino acid sequence as set forth in GX$_1$X$_2$X$_3$X$_4$X$_5$RCMA (SEQ ID NO: 2), wherein X$_1$ may be K or N; X$_2$ may be M or I; X$_3$ may be S or I; X$_4$ may be S or R; and X$_5$ may be R or V. For example, the reference anti-PD-L1 antibody may comprise a heavy chain CDR1 comprising an amino acid sequence as set forth in any one of SEQ ID NO: 3 and 7. In some cases, the reference anti-PD-L1 antibody may comprise a heavy chain CDR2. The heavy chain CDR2 may comprise an amino acid sequence as set forth in any one of SEQ ID NO: 4, 8 and 11. In some cases, the reference anti-PD-L1 antibody is an ISVD specific for PD-L1, such as an anti-PD-L1 VHH. The reference anti-PD-L1 antibody may comprise a heavy chain variable domain. The reference anti-PD-L1 antibody may comprise a heavy chain variable domain comprising an amino acid sequence as set forth in any one of SEQ ID NO: 6, 10, 12, 13, 14 and 15. For example, the heavy chain variable domain may comprise an amino acid sequence as set forth in SEQ ID NO: 6.

In the present disclosure, the ISVD specific for PD-L1 (e.g., as comprised in the dimer of the present disclosure) may comprise a heavy chain CDR3. The heavy chain CDR3 may comprise an amino acid sequence as set forth in DSFX$_1$X$_2$PTCX$_3$X$_4$X$_5$X$_6$SSGAFQY (SEQ ID NO: 1), wherein X$_1$ may be E or G; X$_2$ may be D or Y; X$_3$ may be T or P; X$_4$ may be L or G; X$_5$ may be V or P; and X$_6$ may be T or A. For example, the ISVD specific for PD-L1 may comprise a heavy chain CDR3 comprising an amino acid sequence as set forth in any one of SEQ ID NO: 5 and 9.

For example, the ISVD specific for PD-L1 may comprise a heavy chain CDR3 comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 5 and 9. In some cases, the heavy chain CDR3 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NOs: 5 and 9.

In the present disclosure, the ISVD specific for PD-L1 (e.g., as comprised in the dimer of the present disclosure) may also comprise a heavy chain CDR1. The heavy chain CDR1 may comprise an amino acid sequence as set forth in $GX_1X_2X_3X_4X_5RCMA$ (SEQ ID NO: 2), wherein $X_1$ may be K or N; $X_2$ may be M or I; $X_3$ may be S or I; $X_4$ may be S or R; and $X_5$ may be R or V. For example, the ISVD specific for PD-L1 may comprise a heavy chain CDR1 comprising an amino acid sequence as set forth in any one of SEQ ID NO: 3 and 7.

For example, the ISVD specific for PD-L1 may comprise a heavy chain CDR1 comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 3 and 7. In some cases, the heavy chain CDR1 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NOs: 3 and 7.

In the present disclosure, the ISVD specific for PD-L1 (e.g., as comprised in the dimer of the present disclosure) may further comprise a heavy chain CDR2. The heavy chain CDR2 may comprise any suitable amino acid sequence. In some case, the ISVD specific for PD-L1 may comprise a heavy chain CDR2 comprising an amino acid sequence as set forth in any one of SEQ ID NO: 4, 8 and 11.

For example, the ISVD specific for PD-L1 may comprise a heavy chain CDR2 comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 4, 8 and 11. In some cases, the heavy chain CDR2 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NOs: 4, 8 and 11.

For example, the ISVD specific for PD-L1 may comprise the CDR3 comprising an amino acid sequence as set forth in SEQ ID NO. 5, the CDR2 comprising an amino acid sequence as set forth in SEQ ID NO. 4, and the CDR1 comprising an amino acid sequence as set forth in SEQ ID NO. 3.

In the present disclosure, the ISVD specific for PD-L1 (as comprised in the dimer of the present disclosure) may comprise a heavy chain variable domain. The ISVD specific for PD-L1 may comprise a heavy chain variable domain comprising an amino acid sequence as set forth in any one of SEQ ID NO: 6, 10, 12, 13, 14 and 15. For example, the heavy chain variable domain may comprise an amino acid sequence as set forth in SEQ ID NO: 6.

For example, the ISVD specific for PD-L1 may comprise a heavy chain variable domain comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 6, 10, 12, 13, 14 and 15. In some cases, the ISVD specific for PD-L1 may comprise a heavy chain variable domain comprising an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NO: 6, 10, 12, 13, 14 and 15.

In the present disclosure, the ISVD specific for PD-L1 may comprise an amino acid sequence as set forth in any one of SEQ ID NO: 6, 10, 12, 13, 14 and 15. For example, the ISVD specific for PD-L1 (as comprised in the dimer of the present disclosure) may comprise an amino acid sequence as set forth in SEQ ID NO: 6. For example, the ISVD specific for PD-L1 may comprise an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 6, 10, 12, 13, 14 and 15. In some cases, the ISVD specific for PD-L1 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NO: 6, 10, 12, 13, 14 and 15.

In some cases, the ISVD specific for PD-L1 comprises or consists of a heavy chain variable domain (VH or VHH).

For example, the ISVD specific for PD-L1 may be selected from PD-L1 ISVD-9, PD-L1 ISVD-6, PD-L1 ISVD-m3, PD-L1 ISVD-4, PD-L1 ISVD-11 and PD-L1 ISVD-13. For another example, the ISVD specific for PD-L1 may be selected from PD-L1 ISVD-9.

The ISVD specific for CTLA4 may be capable of specifically binding to human CTLA4. For example, the ISVD specific for CTLA4 may be capable of specifically binding to an epitope in an extracellular domain of the human CTLA4, such an epitope may include those described in CN107400166A, and those described by Udupi A. Ramagopal, et. al., *PNAS* 2017 May, 114 (21)

The ISVD specific for CTLA4 may be capable of blocking binding of CTLA4 to CD80. In some cases, the ISVD specific for CTLA4 may be capable of blocking binding of CTLA4 to CD86. In some cases, the ISVD specific for CTLA4 may be humanized.

The ISVD specific for CTLA4 may cross-compete for binding to CTLA4 with a reference anti-CTLA4 antibody.

The reference anti-CTLA4 antibody may comprise a heavy chain CDR3. The heavy chain CDR3 may comprise an amino acid sequence as set forth in SEQ ID NO: 19. The reference anti-CTLA4 antibody may also comprise a heavy chain CDR1. The heavy chain CDR1 may comprise an amino acid sequence as set forth in SEQ ID NO: 17. In some cases, the reference anti-CTLA4 antibody may comprise a heavy chain CDR2. The heavy chain CDR2 may comprise an amino acid sequence as set forth in $AIX_1X_2GGGSTYYADSVKG$ (SEQ ID NO: 16), wherein $X_1$ may be Y or S; and $X_2$ may be I or L. For example, the heavy chain CDR2 may comprise an amino acid sequence as set forth in any one of SEQ ID NO: 18, 21 and 23. In some cases, the reference anti-CTLA4 antibody is an ISVD specific for CTLA4, such as an anti-CTLA4 VHH. The reference anti-CTLA4 antibody may comprise a heavy chain variable domain. The reference anti-CTLA4 antibody may comprise a heavy chain variable domain comprising an amino acid sequence as set forth in any one of SEQ ID NO: 20, 22, and 24-32. For example, the heavy chain variable domain may comprise an amino acid sequence as set forth in SEQ ID NO: 20.

In the present disclosure, the ISVD specific for CTLA4 (e.g., as comprised in the dimer of the present disclosure) may comprise a heavy chain CDR3. The heavy chain CDR3 may comprise an amino acid sequence as set forth in SEQ ID NO: 19.

In some cases, the ISVD specific for CTLA4 may comprise a heavy chain CDR3 comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in SEQ ID NO: 19. In some cases, the heavy chain CDR3 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in SEQ ID NO: 19.

In the present disclosure, the ISVD specific for CTLA4 (e.g., as comprised in the dimer of the present disclosure) may also comprise a heavy chain CDR1. The heavy chain CDR1 may comprise an amino acid sequence as set forth in SEQ ID NO: 17.

In some cases, the ISVD specific for CTLA4 may comprise a heavy chain CDR1 comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in SEQ ID NO: 17. In some cases, the heavy chain CDR1 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in SEQ ID NOs: 17.

In the present disclosure, the ISVD specific for CTLA4 (e.g., as comprised in the dimer of the present disclosure) may further comprise a heavy chain CDR2. The heavy chain CDR2 may comprise an amino acid sequence as set forth in AIX$_1$X$_2$GGGSTYYADSVKG (SEQ ID NO: 16), wherein X$_1$ may be Y or S; and X$_2$ maybe I or L. In some case, the ISVD specific for CTLA4 may comprise a heavy chain CDR2 comprising an amino acid sequence as set forth in any one of SEQ ID NO: 18, 21 and 23.

For example, the ISVD specific for CTLA4 may comprise a heavy chain CDR2 comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 18, 21 and 23. In some cases, the heavy chain CDR2 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NOs: 18, 21 and 23.

For example, the ISVD specific for CTLA4 may comprise the CDR3 comprising an amino acid sequence as set forth in SEQ ID NO. 19, the CDR2 comprising an amino acid sequence as set forth in SEQ ID NO. 18, and the CDR1 comprising an amino acid sequence as set forth in SEQ ID NO. 17.

In the present disclosure, the ISVD specific for CTLA4 (as comprised in the dimer of the present disclosure) may comprise a heavy chain variable domain. The ISVD specific for CTLA4 may comprise a heavy chain variable domain comprising an amino acid sequence as set forth in any one of SEQ ID NO: 20, 22, and 24-32. For example, the heavy chain variable domain may comprise an amino acid sequence as set forth in SEQ ID NO: 20.

For example, the ISVD specific for CTLA4 may comprise a heavy chain variable domain comprising an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 20, 22, and 24-32. In some cases, the ISVD specific for CTLA4 may comprise a heavy chain variable domain comprising an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NO: 20, 22, and 24-32.

In the present disclosure, the ISVD specific for CTLA4 may comprise an amino acid sequence as set forth in any one of SEQ ID NO: 20, 22, and 24-32. For example, the ISVD specific for CTLA4 (as comprised in the dimer of the present disclosure) may comprise an amino acid sequence as set forth in SEQ ID NO: 20.

For example, the ISVD specific for CTLA4 may comprise an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 20, 22, and 24-32. In some cases, the ISVD specific for CTLA4 may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NO: 20, 22, and 24-32.

In some cases, the ISVD specific for CTLA4 comprises or consists of a heavy chain variable domain (VH or VHH).

For example, the ISVD specific for CTLA4 may be selected from CTLA4 ISVD-34, CTLA4 ISVD-C1, CTLA4 ISVD-13, CTLA4 ISVD-26, CTLA4 ISVD-27, CTLA4 ISVD-28, CTLA4 ISVD-29, CTLA4 ISVD-30, CTLA4 ISVD-31, CTLA4 ISVD-32, and CTLA4 ISVD-33.

For example, the dimer of the present application may comprise or consist of two polypeptide chains. The amino acid sequence of the two polypeptide chains may be identical or different. In some cases, the dimer of the present disclosure may be homodimer.

In the present disclosure, one or both of the two polypeptide chains of the dimer may comprise an amino acid sequence as set forth in SEQ ID NO: 40.

In specific examples, one or both of the two polypeptide chains of the dimer may comprise an amino acid sequence having at least 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) identity to an amino acid sequence as set forth in any one of SEQ ID NO: 40-43, 46, 48 and 50. In some cases, one or both of the two polypeptide chains of the dimer may comprise an amino acid sequence having one or more (e.g., 1-2, 1-3, 1-4, 1-5, 1-6, 1-7, 1-8, 1-9, 1-10, or more) amino acid deletion, insertion and/or substitution in the sequence as set forth in any one of SEQ ID NO: 40-43, 46, 48 and 50.

In an example, an ISVD specific for PD-L1 may be fused (directly or indirectly, e.g., via a linker, such as a peptide linker) to an N-terminal amino acid of an ISVD specific for CTLA4 to form a bi-specific binding moiety. Then, one such bi-specific binding moiety may be fused (directly or indirectly, e.g., via a linker, such as a peptide linker) to an N-terminal amino acid of one Fc subunit of the present disclosure to provide one polypeptide chain of the dimer. Then, another such bi-specific binding moiety may be fused (directly or indirectly, e.g., via a linker, such as a peptide linker) to an N-terminal amino acid of another Fc subunit of the present disclosure to provide the other polypeptide chain of the dimer. The two Fc subunits of the two polypeptide chains may associate with each other (e.g., via non-covalent interactions and/or disulfide bond or other covalent bond, in some cases, such covalent bond is not a peptide bond) to form the dimer. The two bi-specific binding moieties may be identical or different. The two Fc subunits may be identical or different.

In some embodiments, the dimer is a proteinaceous homodimer comprising two identical polypeptide chains, with each polypeptide chain comprising one of the bi-specific binding moiety fused to one of the Fc subunits, and the two Fc subunits associate with each other to form the proteinaceous homodimer. The two Fc subunits may associate with each other via non-covalent interactions and/or disulfide bond or other covalent bond, in some cases, such covalent bond is not a peptide bond.

FIGS. 1A-1B provide examples of the dimer of the present disclosure, wherein 1 indicates the ISVD specific for PD-L1, 2 indicates the ISVD specific for CTLA4, 3 indicates the Fc domain comprising the Fc subunits, and 4 indicates the bi-specific binding moiety.

The dimer of the present disclosure may be capable of competing with CD80 and/or CD86 for binding to CTLA4. For example, the competition may be examined in an in vitro experiment using CTLA4 expressing cell lines, such as a CTLA4 expressing HEK293 cell line. As another example, the competition may be examined in an ELISA essay, such as a competition ELISA assay.

The dimer of the present disclosure may be capable of competing with PD1 and/or CD80 for binding to PD-L1. For example, the competition may be examined in an in vitro experiment using PD-L1 expressing cell lines, such as a PD-L1 expressing A375 cell line. As another example, the competition may be examined in an ELISA essay, such as a competition ELISA assay.

The dimer of the present disclosure may be capable of blocking binding of PD-L1 to PD-1. In some cases, the dimer of the present disclosure may be capable of blocking binding of PD-L1 to CD80. In some cases, the dimer of the present disclosure may be capable of blocking binding of CTLA4 to CD80. In some cases, the dimer of the present disclosure may be capable of blocking binding of CTLA4 to CD86.

The dimer of the present disclosure may bind to CTLA4 with a $K_D$ of a value no more than about $1 \times 10^{-6}$ M, for example, no more than about $1 \times 10^{-7}$ M, no more than about $1 \times 10^{-8}$ M, no more than about $0.5 \times 10^{-8}$ M, no more than about $1 \times 10^{-9}$ M, no more than about $1 \times 10^{-10}$ M or lower.

The dimer of the present disclosure may bind to PD-L1 with a $K_D$ of a value no more than about $1 \times 10^{-6}$ M, for example, no more than about $1 \times 10^{-7}$ M, no more than about $1 \times 10^{-8}$ M, no more than about $0.5 \times 10^{-8}$ M, no more than about $1 \times 10^{-9}$ M, no more than about $1 \times 10^{-10}$ M or lower.

The dimer of the present disclosure may be capable of stimulating the secretion of an immunoregulator (e.g., IL-2) by immune cells (e.g., PBMC cells).

For example, the dimer of the present disclosure may be selected from aPDL1.9-aCTLA4.34-Fc, aPDL1.9-L-aCTLA4.34-Fc, aCTLA4.34-aPDL1.9-Fc, aCTLA4.34-L-aPDL1.9-Fc, aPDL1.6-aCTLA4.34-Fc, aPDL1.m3-aCTLA4.34-Fc and aPDL1.9-aCTLA4.13-Fc.

For example, the dimer of the present disclosure may comprise the ISVD specific for CTLA4 and the ISVD specific for PDL1. The ISVD specific for PD-L1 may comprise the CDR3 comprising an amino acid sequence as set forth in SEQ ID NO. 5, the CDR2 comprising an amino acid sequence as set forth in SEQ ID NO. 4, the CDR1 comprising an amino acid sequence as set forth in SEQ ID NO. 3. And the ISVD specific for CTLA4 may comprise the CDR3 comprising an amino acid sequence as set forth in SEQ ID NO. 19, the CDR2 comprising an amino acid sequence as set forth in SEQ ID NO. 18, and the CDR1 comprising an amino acid sequence as set forth in SEQ ID NO. 17. And the dimer of the present disclosure may comprise the ISVD specific for PD-L1 comprising an amino acid sequence as set forth in SEQ ID NO. 6, and the ISVD specific for CLTA4 comprising an amino acid sequence as set forth in SEQ ID NO. 20. For example, the dimer of the present disclosure may comprise an amino acid sequence of SEQ ID NO. 40.

And the dimer of the present disclosure may be named as KN046.

Use and Method

In the present disclosure, provided a use of a dimer in the preparation of a medicament for treating a tumor in a subject in need thereof. The present disclosure further provides a method for treating a tumor in a subject in need thereof, comprising administering to said subject an effective amount of the dimer.

In some embodiments, the subject may have been treated for a tumor with one or more available therapies currently but not substantially responsive to it. The term "not substantially responsive" may be a condition in which patients undergoing or treated with one or more currently available therapies (e.g., tumor therapies, such as chemotherapy, radiation therapy, chemoradiation therapy, CTL cell therapy, EGFR tyrosine kinase inhibitors (TKIs) therapy, angiogenesis inhibitors therapy, surgery, hormonal therapy and/or biological therapy/immunotherapy, immune checkpoint inhibitor therapy, particularly a standard therapeutic regimen for the particular tumor) is not clinically adequate to treat the patients or the patients are no longer receiving any beneficial effect from the therapy such that these patients need additional effective therapy.

In some embodiments, the therapies may comprise those treatments for NSCLC, melanoma, esophageal squamous cell carcinoma (ESCC), NPC or breast cancer (for example, Triple-negative breast cancer (TNBC)).

In present disclosure, said tumor may be selected from a group consisting of NSCLC, melanoma, esophageal squamous cell carcinoma (ESCC), NPC or breast cancer.

For example, said tumor may be selected from a group consisting of esophageal squamous cell carcinoma (ESCC) and nasopharyngeal carcinoma (NPC).

For example, said tumor may be selected from selected from a group consisting of locally advanced-stage or metastatic melanoma, non-keratinized locally advanced recurrent or metastatic NPC, metastatic NSCLC, squamous and non-squamous NSCLC, recurrent or metastatic ESCC and Triple-negative breast cancer (TNBC).

For example, said tumor may be selected from selected from a group consisting of advanced NSCLC without EGFR mutation or ALK fusions, NSCLC with EGFR Exon 20 insertion mutation, NPC with positive PD-L1 expression and locally advanced inoperable or metastatic TNBC.

In some embodiments, the subject may have been administered with an immune checkpoint inhibitor. For example, the dimer may be administered after administration of the immune checkpoint inhibitor for about 1 min, 2 mins, 5 mins, 10 mins, 20 mins, 30 mins, 45 mins, 1 hour, 2 hours, 3 hours, 4 hours, 5 hours, 6 hours, 12 hours, 18 hours, 1 day, 2 days, 3 days, 1 week, 2 weeks, 3 weeks, 1 month, 2 months, 3 months 6 months, 1 years, 2 years 3 years or longer.

In some embodiments, the subject may be not substantially responsive to said immune checkpoint inhibitor. In some embodiments, the immune checkpoint inhibitor may be selected from a group consisting of: PD-L1 inhibitor, PD-1 inhibitor and CTLA4 inhibitor.

A subject who is not substantially responsive to an immune checkpoint inhibitor, may have previously responded to an immune checkpoint inhibitor, but may have become less responsive to the immune checkpoint inhibitor, or the subject may have never responded to the immune checkpoint inhibitor. Inadequate response to an immune checkpoint inhibitor means that aspects of the condition that would be expected to improve following a standard dose of the immune checkpoint inhibitor do not improve, and/or improvement only occurs if greater than a standard dose is administered. In some embodiments, a subject who is not substantially responsive to an immune checkpoint inhibitor may have experienced, or is experiencing, an inadequate response to the immune checkpoint inhibitor after receiving a standard dose for at least two weeks, at least three weeks, at least four weeks, at least six weeks, or at least twelve weeks. A "standard" dose is determined by a medical professional, and may depend on the subject's age, weight, healthy history, severity of disease, the frequency of dosing, etc.

In present disclosure, said subject may have been administrated chemotherapy, chemoradiation, CTL cell therapy, EGFR tyrosine kinase inhibitors (TKIs), and/or angiogenesis inhibitors.

In present disclosure, said chemotherapy may refer to any treatment against said tumor by chemical agents. Said chemical agent may kill tumor cells, shrink a tumor and/or relieve signs and symptoms of cancer. For example, said chemotherapy may comprise a first line chemotherapy and/or a second line chemotherapy. In present disclosure, said first line chemotherapy may refer to a chemotherapy regimen or regimens that are generally accepted by the medical establishment for initial treatment of a given type and stage of cancer. For example, said first line chemotherapy may comprise a platinum-based chemotherapy. In some embodiments, said first line platinum-based chemotherapy may comprise chemotherapy with a platinum (P) compound (cisplatin or carboplatin).

In present disclosure, said second line chemotherapy may refer to those tried when the first ones do not work adequately. For example, said second line chemotherapy may comprise paclitaxel, docetaxel, capecitabine and/or 5-FU.

In present disclosure, said chemoradiation (CRT, CRTx, CT-RT) may refer to treatment that combines chemotherapy with radiation therapy.

In present disclosure, said CTL cell therapy may refer to cytotoxic T lymphocyte therapy.

In present disclosure, said EGFR tyrosine kinase inhibitors may refer to a substance that blocks the activity of a protein called epidermal growth factor receptor (EGFR). Said EGFR tyrosine kinase inhibitors may comprise monoclonal antibodies directed against the surface of the receptor and/or tyrosine kinase inhibitors directed against the intracellular domain of the receptor.

In present disclosure, said angiogenesis inhibitors may refer to a substance that inhibits the growth of new blood vessels (angiogenesis).

In some embodiments, the medicament or the dimer may be administered intravenously, intramuscularly, subcutaneously, topically, orally, transdermally, intraperitoneally, intraprbitally, by implantation, by inhalation, intrathecally, intraventricularly, or intranasally. An effective amount of the medicament may be administered for prevention or treatment of disease. The appropriate dosage of the medicament may be determined based on the type of disease to be treated, the type of the medicament, the severity and course of the disease, the clinical condition of the individual, the subject's clinical history and response to the treatment, and the discretion of the attending physician. For example, an appropriate dosage may be about 0.1 mg or 1 mg/kg/day to about 500 mg/kg/day (such as about 0.1 mg/kg-about 0.3 mg/kg, about 0.1 mg/kg-about 1 mg/kg, about 0.1 mg/kg-about 3 mg/kg, about 0.1 mg/kg-about 5 mg/kg, about 0.1 mg/kg-about 10 mg/kg, such as about 1 mg/kg to about 5 mg/kg, such as about 3 mg/kg to about 5 mg/kg, such as about 1 mg/kg to about 3 mg/kg, such as about 1 mg/kg-about 500 mg/kg or such as about 1 mg/kg-about 150 mg/kg); sometimes, the dosage can be even higher.

In some embodiments, the medicament or the dimer may be administered once every two weeks or once every three weeks.

The medicament may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In some embodiments, the medicament may be administrated intravenously.

In a specific embodiment, it may be desirable to administer the medicament of the present disclosure locally to the area in need of treatment; this may be achieved by, for example, and not by way of limitation, local infusion, topical application, by injection, by means of a catheter, by means of a suppository, or by means of an implant, said implant being of a porous, non-porous, or gelatinous material, including membranes. Preferably, when administering a medicament of the present disclosure, care must be taken to use materials to which the protein does not absorb.

The medicament and/or the immune checkpoint inhibitor may be administered by the same route of administration or by different routes of administration.

The medicament is capable of treating a tumor in a subject in need of. The tumor may be a solid tumor, a hematologic tumor, or a lymphoma. The tumor may be advanced or metastatic tumor. In some embodiments, the tumor may be selected from a group consisting of NSCLC, melanoma, esophageal squamous cell carcinoma (ESCC), NPC or breast cancer (for example, Triple-negative breast cancer (TNBC)).

In some cases, the tumor may be non-responsive to treatment with an immune checkpoint inhibitor (e.g., a PD-1 antagonist and/or a PD-L1 antagonist). For example, treatment with a PD-1 antagonist and/or a PD-L1 antagonist does not result in substantial or observable delay or inhibition of tumor progression or tumor growth. In some cases, prior to administering the dimer/composition/immunoconjugate of the present disclosure, the tumor has not been treated with a PD-1 antagonist and/or a PD-L1 antagonist. The PD-1 antagonist may be a PD-1 blocking antibody. The PD-L1 antagonist may be a PD-L1 blocking antibody.

The tumor or tumor cell may be within the body of a subject, e.g., a tumor or tumor cell within a human or in a non-human animal (e.g., a mammal). In some cases, the tumor/tumor may be unresectable. In some cases, the tumor/tumor may be metastatic (such as metastatic solid tumor).

In some cases, the tumor/tumor may be refractory and/or intolerant to standard therapies. For example, the tumor may be a refractory tumor, which refers to tumor that may be resistant at the beginning of treatment, or becomes resistant during treatment.

In present disclosure, said metastatic refers to a status that a tumor has been spread from an initial or primary site to a different or secondary site within the body of a subject.

In present disclosure, said recurrent refers to a status that a tumor was found after treatment, and/or after a period of time when the tumor could not be detected. The recurrent tumor may be in the same place it first started or in the somewhere else within the body of a subject.

In present disclosure, said mutation refers to an alteration in the nucleotide sequence of the genome. For example, said mutation may comprise a deletion, an insertion and/or a substitution of a nucleotide and/or a component of a gene (for example, an exon).

In present disclosure, said dimer is administered in combination with a chemotherapy agent.

In present disclosure said chemotherapy agent may be any agent capable of chemotherapy. For example, said chemotherapy agent may comprise platinum doublets and/or paclitaxel. For example, said chemotherapy agent may comprise cisplatin, gemcitabine and/or nab-paclitaxel.

For example, said tumor may comprise recurrent or metastatic ESCC, with which the subject thereof has not been treated by CRT within 6 months, and then received palliative CRT consisting of cisplatin, paclitaxel and radiation.

For example, said tumor may comprise advanced NSCLC without EGFR mutation or ALK fusions, which was progressed on 1st line platinum-based chemotherapy but not treated with any PD-(L)1 immune checkpoint inhibitor.

For example, said tumor may comprise NSCLC having EGFR exon 20-insertion mutation, with which the subject thereof was ineffective with the treatment of EGFR tyrosine kinase inhibitors (TKIs).

For example, said tumor may comprise NPC, with which the subject thereof was ineffective with the treatment of said first line chemotherapy, said second line chemotherapy and/or anti-PD-1 agent.

Combination

In another aspect, the present disclosure provides a use of the dimer of present disclosure in combination with a chemotherapy agent of present disclosure in the preparation of a medicament for treating a tumor in a subject in need thereof.

In another aspect, the present disclosure provides the dimer of present disclosure in combination with a chemotherapy agent of present disclosure, for use in treating a tumor in a subject in need thereof.

In another aspect, the present disclosure provides a method of treating a tumor in a subject in need thereof, comprises administrating the dimer of present disclosure in combination with a chemotherapy agent of present disclosure.

In present disclosure, said tumor may be selected from a group consisting of a solid tumor and a hematologic tumor. For example, said tumor may be selected from a group consisting of NSCLC and breast cancer.

For example, said tumor may be selected from a group consisting of squamous and non-squamous NSCLC and Triple-negative breast cancer (TNBC). For example, said tumor may be selected from a group consisting of NSCLC with EGFR Exon 20 insertion mutation and locally advanced inoperable or metastatic TNBC.

In present disclosure, said subject may have been administrated EGFR tyrosine kinase inhibitors (TKIs).

In present disclosure, said dimer may be administrated at a dosing frequency of four times a week, twice a week, once a week, once every two weeks, once every three weeks, once every four weeks, once every five weeks, once every six weeks, once every eight weeks or once every twelve weeks. For example, said dimer may be administrated at a dosing frequency of once every two weeks.

In present disclosure, said chemotherapy agent may be administrated at a dosing frequency of four times a week, twice a week, once a week, once every two weeks, once every three weeks, once every four weeks, once every five weeks, once every six weeks, once every eight weeks or once every twelve weeks.

In present disclosure, said dimer may be administrated intravenously, intramuscularly, subcutaneously, topically, orally, transdermally, intraperitoneally, intraorbitally, by implantation, by inhalation, intrathecally, intraventricularly, or intranasally.

In present disclosure, said chemotherapy agent may be administrated intravenously, intramuscularly, subcutaneously, topically, orally, transdermally, intraperitoneally, intraorbitally, by implantation, by inhalation, intrathecally, intraventricularly, or intranasally.

In present disclosure, said dimer may be administrated at dose of 0.01 mg/kg to 100 mg/kg. For example, said dimer may be administrated at dose of about 1 mg/kg to about 5 mg/kg, about 3 mg/kg to about 5 mg/kg, or about 1 mg/kg to about 3 mg/kg.

In present disclosure, said chemotherapy agent may be administrated at dose of 0.01 mg/kg to 100 mg/kg. For example, said platinum-based agent may be administrated at dose of about 1 mg/kg to about 5 mg/kg, about 3 mg/kg to about 5 mg/kg, or about 1 mg/kg to about 3 mg/kg.

In some embodiments, said dimer may be administrated in combination with platinum doublets. For example, said tumor may comprise NSCLC having EGFR exon 20-insertion mutation, with which the subject thereof was ineffective with the treatment of EGFR tyrosine kinase inhibitors (TKIs).

In some embodiments, said dimer may be administrated in combination with a paclitaxel, for example, a nab-paclitaxel. For example, said tumor may comprise Metastatic Triple-negative Breast Cancer (mTNBC), with which the subject thereof is treatment-naïve. For example, said tumor may comprise locally advanced inoperable or metastatic TNBC.

In another aspect, the present disclosure provides a kit comprises the dimer of present disclosure in combination with a chemotherapy agent of present disclosure.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1 Phase I Study in Patients with Tumors

This is a phase Ia/Ib, open-label, multicenter, dose-escalation and expansion study to evaluate the safety, tolerability, pharmacokinetics and anti-tumor activity of the dimer in subjects with advanced solid tumors and lymphoma. 16 participants were estimated enrollments.

Inclusion Criteria:

1. Signed informed consent; willing and able to complete all required procedures of study.

2. Solid tumor confirmed by histology or cytology. The subjects are patients with advanced-staged or metastatic solid tumor (unresectable) experienced progression since last anti-tumor treatment; standard therapy is not available or rejected; or the subject is a patient with refractory solid tumors that cannot tolerate standard treatment or has contraindications to standard treatment, including chemo-therapy, targeted therapy, etc.;

3. For specific tumor types in the study dose/cohort expansion phase:

a. melanoma: locally advanced-stage or metastatic melanoma (unresectable) confirmed by histology; first-line chemotherapy or first-line targeted therapy (e.g., chemotherapy, TSA-CTL cell therapy, immune checkpoint inhibitor therapy) had failed;

b. nasopharyngeal carcinoma: non-keratinized locally advanced recurrent or metastatic nasopharyngeal carcinoma confirmed by histology; first-line or first-line above platinum-containing chemotherapy (e.g. platinum-containing chemoradiotherapy or platinum-containing chemoradiotherapy plus adjuvant chemotherapy) had failed;

c. NSCLC: first-line therapy (chemotherapy, angiogenesis inhibitors and immune checkpoint inhibitor treatment) had failed.

Phase Ia: Intravenous (IV) infusions, 1, 3 and 5 milligrams per kilogram (mg/kg) every 2 weeks. Phase Ib: Intravenous (IV) infusions, 1, 3 or 3, 5 milligrams per kilogram (mg/kg) every 2 weeks, the dose of phase Ib based on the result of phase Ia. Or 300, 500 milligrams per kilogram (mg/kg) every 3 weeks.

In phase Ia, the primary outcome measure is number of participants with dose limiting toxicity (DLT). In phase Ib, the primary outcome measures are objective response rate (ORR) and duration of response (DoR) according to RECIST 1.1 or Lugano 2014 criteria. The secondary outcome measures are treatment emergent adverse event (TEAE), adverse reaction, PK parameters (include but not limit to AUC0-t, Cmax, CL, T½, Ctrough), etc.

The treatment period continues until disease progression or occurrence of unacceptable toxicity. During follow-up, subjects are monitored for disease activity and safety.

Figure 2:
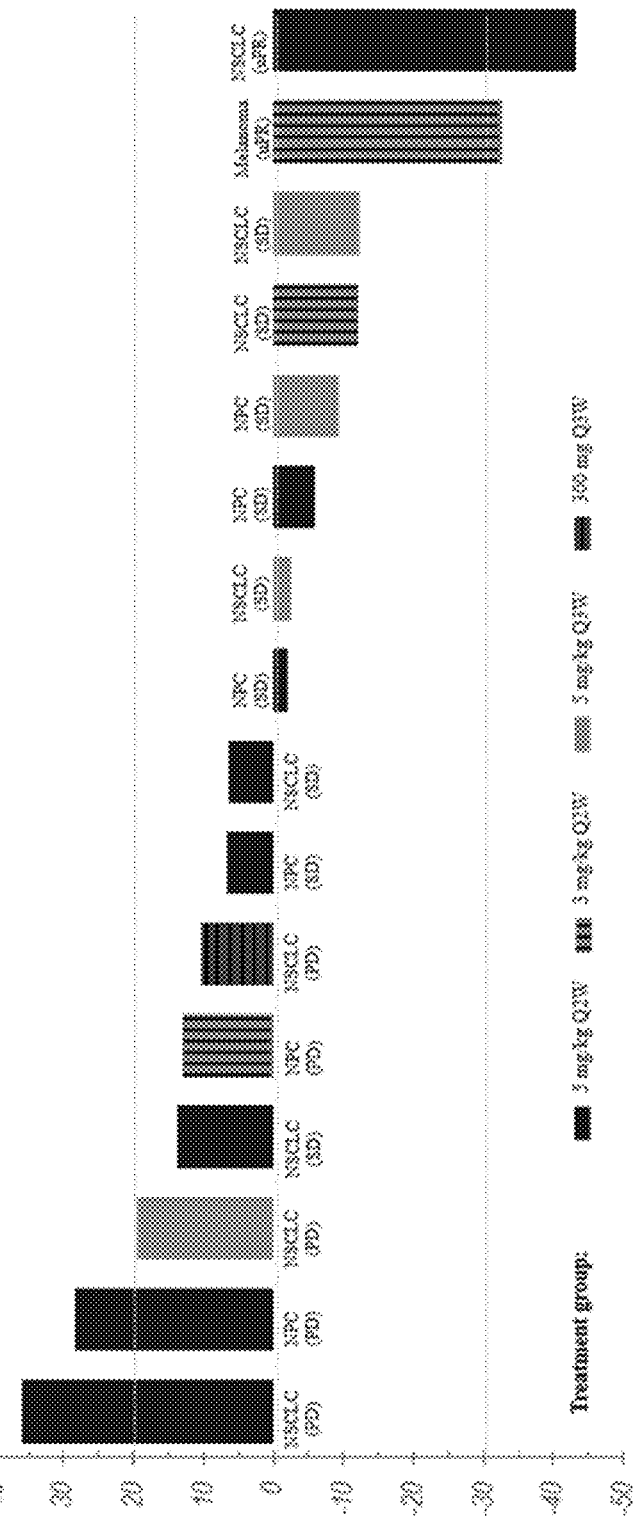
FIG. 2 illustrates the summary of efficacy in phase I study of solid tumor patients.

FIG. 2 illustrated the results of patients who had failed with immune checkpoint inhibitor treatments. The ORR is 12.5%, and the DCR 63%. In cohort of 5 mg/kg Q2W (N=8), the ORR is 12.5%, and the DCR is 75%. Progressive disease (PD) didn't occur in the 14 patients among 16 patients with NSCLC, NPC or melanoma.

Single agent has an acceptable safety profile.

Example 2 the Preliminary Efficacy and Safety of KN046 Plus Concurrent Chemoradiation Therapy in Esophageal Squamous Cell Carcinoma BACKGROUND Definitive or palliative chemoradiation therapy has been employed in the management of esophageal squamous cell carcinoma (ESCC). Immune checkpoint inhibitor has improved outcomes in metastatic stage IV pts. Here we report the addition of KN046, a PD-L1/CTLA-4 bispecific antibody, to concurrent chemoradiation (CRT) therapy to determine the safety and efficacy of this approach (ChiCTR2000031544).

OBJECTIVES & METHODS Eligible patients (Pts) with recurrent or metastatic ESCC, not been treated by CRT within 6 months, were recruited and received palliative CRT consisting of cisplatin (75 mg/m2 IV Q3W for 4-6 cycles), paclitaxel (135-175 mg/m2 IV Q3W for 4-6 cycles) and radiation (30-40 Gy at the investigator's discretion according to institutional standard). KN046 at ascending doses of 1, 3 and 5 mg/kg was added within 7-14 days after the completion of radiation therapy (RT) and concurrently with chemotherapy, followed by KN046 Q2W maintenance. Dose limiting toxicities (DLTs) were assessed for the first treatment cycle of KN046. Anti-tumor activity was assessed according to RECIST 1.1 every 6 weeks within the first year, and every 12 weeks thereafter.

RESULTS As of Jun. 30, 2020, 18 subjects were enrolled and received KN046 treatment (1 mg/kg, n=3; 3 mg/kg, n=11; 5 mg/kg, n=4). The median KN046 exposure was 11.5 weeks. No DLT was reported. 3 (16.7%) subjects experienced Grade 3, KN046 related adverse events (1 Grade 3 pneumonitis recovered by steroid and antibiotic Tx, 1 Grade 3 colitis recovered after antibiotic Tx alone and 1 Grade 3 colitis recovered after steroid and antibiotic Tx). At 3 mg/kg, objective response was observed in 5 out of 9 efficacy evaluable pts (55.6%) and disease control rate 100%; 8/9 (88.9%) pts experienced further tumor reduction after initiation of KN046 treatment.

CONCLUSION The addition of KN046 to CRT was well tolerated and showed promising efficacy signal in recurrent or metastatic ESCC. This pilot study enables further investigation of a new treatment modality of KN046 with CRT in this poorly prognosed disease.

Example 3 A Phase II Study of KN046 in Patients (Pts) with Metastatic Non-Small Cell Lung Cancer (NSCLC)

Background: KN046 is a novel bispecific antibody that blocks PD-L1 interaction with PD-1 and CTLA-4 interaction with CD80/CD86. This multiple-cohort, single-arm phase II study evaluates preliminary safety and efficacy of KN046 in subjects with metastatic non-small cell lung cancer (NSCLC).

Methods: Eligible patients (pts) were advanced NSCLC without EGFR mutation or ALK fusions, progressed on 1st line platinum-based chemotherapy but not treated with any PD-(L)1 immune checkpoint inhibitor. All pts were given KN046 3 mg/kg (Cohort A) or 5 mg/kg (Cohort B) Q2W IV up to disease progression, intolerable toxicity, etc. Efficacy evaluation was performed by investigators per RECIST 1.1 every 8 weeks and safety and tolerability assessed per NCI-CTCAE v5.0.

Results: As of the Jul. 27, 2020, 30 pts enrolled in Cohort A and 33 in Cohort B. Median age 59 years, male/female 51/12, PS 0/1 9/54, squamous NSCLC/Non-squamous NSCLC 23/40. ≥Grade 3 TRAEs were seen in 21 (33.3%) pts, treatment related SAE 16 (25.4%) pts, irAEs 34 (54.0%) pts, ≥Grade 3 irAEs 11 (17.5%) pts. Common (≥10%) TRAEs were infusion related reaction (16, 25.4%), anemia (14, 22.2%), rash (13, 20.6%), hyperglycemia (12, 19.0%), abnormal hepatic function (10, 15.9%), hypothyroidism (10, 15.9%), alanine aminotransferase increased (8, 12.7%), asthenia (8, 12.7%), aspartate aminotransferase increased (7, 11.1%) and pruritus (7, 11.1%). Safety profile was comparable between two cohorts.

As of cutoff date, 24 (37.5%) pts remained on the study treatment, and 39 (60.9%) pts discontinued treatment due to disease progression (n=27), AE (n=7), poor patient compliance (n=4) and one death. Median duration of drug exposure was 14 weeks (two to 56 weeks). ORR and DCR were 10.7% and 71.4% in 56 evaluable pts. Median PFS were 3.7 (2.9, 7.3), 6 and 12-month PFS rate (95% CI) were 36.6% (23.0, 50.4) and 18.3% (6.2, 35.5), 6 and 12-month OS rate (95% CI) were 86.9% (74.2, 93.6) and 60.7% (36.0, 78.4). In squamous NSCLC, median PFS was 7.3 (3.7, NE), 9-month PFS rate (95% CI) was 46.6% (19.0, 70.3), 6 and 12-month OS rate (95% CI) were 88.2% (60.2, 96.9) and 52.9% (13.2, 81.9).

Conclusions: The bispecific antibody, KN046 was well tolerated and effective as 2nd line treatment of advanced NSCLC. KN046 showed promising PFS and OS benefit in squamous NSCLC.

Clinical trial information: NCT03838848

Example 4 Preliminary Breakthrough Therapy Designation Request (BTDR) Advice This document will be used as a basis for the Division to comment on whether a request for a Breakthrough Therapy Designation (BTD) is appropriate, at this time, may be too preliminary, or does not currently meet the BTD criteria.

1. Provide information related to whether the indication is serious and life-threatening. Briefly describe the indication and the disease for which the product is intended:

KN046 in combination with platinum doublets is indicated to treat NSCLC with EGFR Exon 20 insertion mutation.

2. Briefly describe the drug, the drug's mechanism of action (if known), the drug's relation to existing therapy(ies):

KN046 is a PD-L1/CTLA-4 bispecific antibody blocking PD1/PD-L1 and CTLA-4 pathways.

3. Briefly describe available therapies, if any:

Approximately 0.5%-4% of EGFRmut NSCLC has exon 20 insertions. Approved EGFR tyrosine kinase inhibitors (TKIs) are ineffective with an objective response rate (ORR) of 16.1%. Chemotherapy with or without TKIs yields an ORR of 27.5%. PFS from available therapies is about 5 months and OS about 16 months. A new therapy is needed for this subtype of NSCLC.

| EGFR Exon 20-Ins | Median OS, months (n) | Median PFS, months (n) | ORR, % (n) |
|---|---|---|---|
| All treatments | 16.2 (666) | 4.8 (707) | 19.8% (684) |
| TKI | 12.6 (210) | 4.0 (317) | 16.1% (409) |
| Chemotherapy +/− TKI | 18.6 (330) | 5.5 (355) | 27.5% (242) |
| I—O agent | 7.5 (29) | 3.2 (26) | 10.0% (30) |

Reference: Annals of Oncology (2020) 31 (suppl_4): S754-S840

4. Provide information related to the preliminary clinical evidence*, including trial design, trial endpoints, treatment groups, and number of subjects enrolled:

KN046-202 (NCT04054531) is an open label, parallel group, phase 2 trial to evaluate efficacy and safety of KN046 in combination with platinum doublets as first line treatment for squamous and non-squamous NSCLC. Enrollment of NSCLC with non-EGFR sensitizing mutation was allowed.

Figure 3:
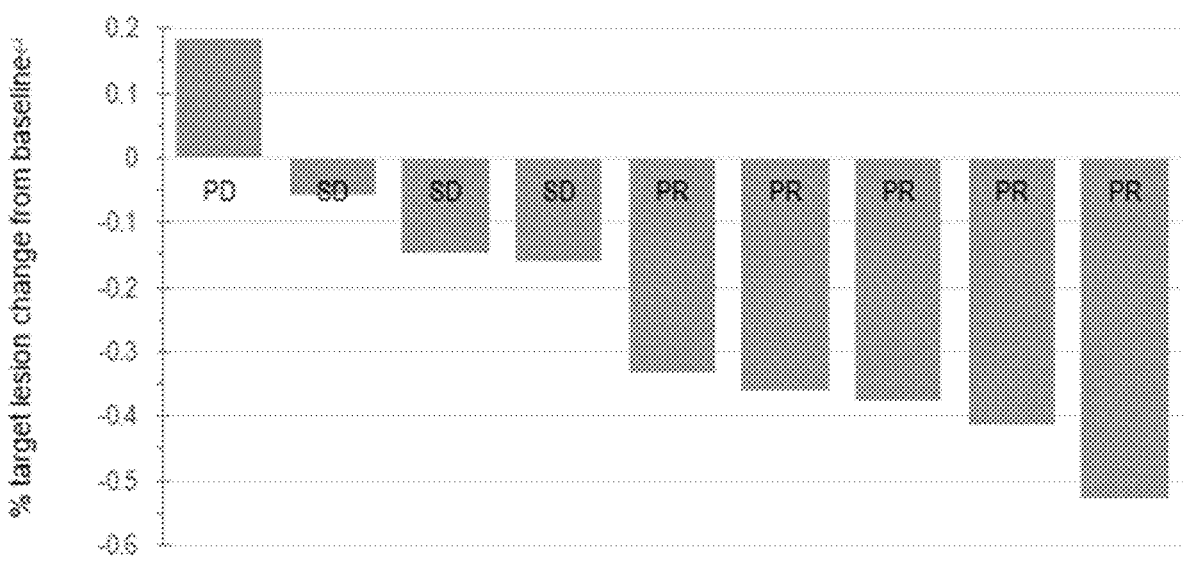
FIG. 3 illustrates the target lesion change from baseline using the dimers of the present disclosure.

As of 3 Sep. 2020, 9 subjects with EGFR exon 20-insertion mutation were enrolled and treated by KN046 in combination with carboplatin and pemetrexed. 55.5% (5/9, 95% CI 21.2%-86.3%) response rate and 88.9% (8/9) disease control rate were observed (FIG. 3).

For example, for Oncology/Hematology products, preliminary clinical evidence could include response rates, duration of response, and extent of prior therapies.

Example 5 Preliminary Breakthrough Therapy Designation Request (BTDR) Advice This document will be used as a basis for the Division to comment on whether a request for a Breakthrough Therapy Designation (BTD) is appropriate, at this time, may be too preliminary, or does not currently meet the BTD criteria.

1. Provide information related to whether the indication is serious and life-threatening. Briefly describe the indication and the disease for which the product is intended:

Indication which the product is intended is nasopharyngeal carcinoma (NPC) with positive PD-L1 expression.

2. Briefly describe the drug, the drug's mechanism of action (if known), the drug's relation to existing therapy(ies):

KN046 is a PD-L1/CTLA-4 bispecific antibody blocking PD1/PD-L1 and CTLA-4 pathways.

3. Briefly describe available therapies, if any:

Platinum doublets (e.g., cisplatin/gemcitabine) is the standard first line therapy with a median progression-free survival (PFS) of 7 months and median overall survival (OS) of 29.1 months. Second line therapies include paclitaxel, docetaxel, capecitabine or 5-FU, and methotrexate with a median OS less than 12 months. Preliminary efficacy data from pembrolizumab and nivolumab in second and late line settings showed 12-month OS rates of 63% and 62%, respectively.

4. Provide information related to the preliminary clinical evidence, including trial design, trial endpoints, treatment groups, and number of subjects enrolled:

KN046-CHN-001 is a phase Ia/Ib dose escalation and expansion trial in subjects with advanced solid tumors. This trial enrolled a total of 59 patients with NPC. All patients failed at least first line systemic therapy, 24 (40.7%) patients failed 2 prior lines of systemic therapies, and 25 (42.4%) patients failed anti-PD-1 agent.

In anti-PD-1 naive population, 29 patients were efficacy evaluable and 24.1% (7/29) response rate was observed. Among 29 patients, 20 patients had positive PD-L1 expression (defined as ≥10% PD-L1 expression in the immune cell using SP263 assay) and response rate was 30%.

Overall survival was not reached with a median follow up of 13 months and minimum follow up of 5.2 months. 12-month OS rates in anti-PD-1 naive and anti-PD-1 pre-treated populations were 71.5% (95% CI 50.1%-85%) and 74.3% (95% CI 47%-89%), respectively.

For example, for Oncology/Hematology products, preliminary clinical evidence could include response rates, duration of response, and extent of prior therapies.

Example 6 Preliminary Safety, Tolerability and Efficacy Results of KN046 (an Anti-PD-L1/CTLA-4 Bispecific Antibody) in Combination with Nab-Paclitaxel in Metastatic Triple-Negative Breast Cancer (mTNBC)

Background:

Triple-negative breast cancer (TNBC) has the poorest outcome when compared to other subtypes of invasive breast cancer. IMpassion130 and Keynote-355 studies demonstrated improved clinical outcome when anti-PD-(L)-1 agents were combined with first line chemotherapies in PD-L1 positive TNBC.

KN046 is a novel bispecific antibody that blocks PD-L1 and CTLA-4 pathways. Here we reported the interim results from an ongoing phase II study for KN046 in combination with nab-paclitaxel in patients (pts) with mTNBC.

Methods:

This study enrolled pts with treatment-naïve locally advanced inoperable or metastatic TNBC. Eligible pts received nab-paclitaxel plus KN046 at two dose levels (DL1: KN046 3 mg/kg Q2W or DL2: KN046 5 mg/kg Q2W). Tumor response was evaluated Q8W per RECIST 1.1. PD-L1 expression was measured using SP142 assay.

Results:

As of Oct. 29, 2020, 27 pts were enrolled into DL1 (n=16) and DL2 (n=11). 12 pts remained on the study and 15 pts discontinued treatment due to disease progression (n=8), death (n=1), adverse events (n=3) and other reasons (n=3). Patients tolerated well to KN046 plus nab-paclitaxel. No KN046 treatment related adverse event (TRAE) leading to death. TRAEs occurred in 27 (100%) pts, 13 (48.1%) were grade 3 or above. 11 (40.7%) pts experienced immune related adverse events (irAEs), including 2 patients experienced one grade 3 immune-mediated hepatic disorder and one grade 3 rash. The most common (≥20%) TRAE were AST increased (48%), ALT increased (48%), pyrexia (33%), neutrophil count decreased (30%), anaemia (26%), rash (26%) and white blood cell count decreased (26%). The most common (≥15%) grade 3 or above TRAEs were neutrophil count decreased (26%), white blood cell count decreased (22%) and AST increased (15%).

Median PFS was 7.33 (4.04, NE) months and 12-month PFS rate was 38.3% (95% CI 19.7-74.6%). Median OS was not reached and 12-months OS rate was 80% (95% CI 61.4~100%).

Among pts with PD-L1 positive (IC PD-L1≥1%) or PD-L1 status unknown tumors (exclude PD-L1<1%), Median PFS was 7.36 (95% CI 7.36, NE) months and 12-month PFS rate was 49.4% (95% CI 20.6~100%). 12-month OS rate was 90.9% (95% CI 75.1~100%).

Conclusions: KN046 combined with nab-paclitaxel is well tolerated and has shown favorable clinical efficacy in PD-L1 positive TNBC. Preliminary overall survival data is encouraging.

Clinical trial information: NCT03872791

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for treating a tumor in a subject in need thereof, comprising administering to said subject an effective amount of a dimer, wherein:

said dimer is formed by two polypeptide chains, with each of said two polypeptide chains comprising an antibody Fc subunit, said dimer comprises two or more immunoglobulin single variable domains (ISVDs), at least one of said ISVDs is specific for PD-L1 (programmed death-ligand 1), and at least one of said ISVDs is specific for CTLA4 (cytotoxic T-lymphocyte associated protein 4), wherein the ISVD specific for PD-L1 comprise the CDR3 as set forth in SEQ ID NO. 5, the CDR2 as set forth in SEQ ID NO. 4, and the CDR1 as set forth in SEQ ID NO. 3, and the ISVD specific for CTLA4 comprises the CDR3 as set forth in SEQ ID NO. 19, the CDR2 as set forth in SEQ ID NO. 18, and the CDR1 as set forth in SEQ ID NO. 17, wherein said tumor is selected from a group consisting of NSCLC (non-small-cell lung carcinoma), melanoma, esophageal squamous cell carcinoma (ESCC), NPC (nasopharyngeal cancer) and breast cancer.

2. The method according to claim 1, wherein for one or both of said two polypeptide chains, said ISVD specific for PD-L1 is fused to said ISVD specific for CTLA4, optionally via a linker.

3. The method according to claim 1, wherein said antibody Fc subunit is derived from an IgG (immunoglobulin G) Fc subunit.

4. The method according to claim 1, wherein said ISVD specific for PD-L1 comprises a heavy chain variable domain comprising an amino acid sequence as set forth in SEQ ID NO: 6.

5. The method according to claim 1, wherein said ISVD specific for CTLA4 comprises a heavy chain variable domain comprising an amino acid sequence as set forth in SEQ ID NO: 20.

6. The method according to claim 1, wherein one or both of said two polypeptide chains comprises an amino acid sequence as set forth in SEQ ID NO: 40.

7. The method according to claim 1, wherein said subject has been administered chemotherapy, chemoradiation, CTL (cytotoxic T lymphocyte) cell therapy, EGFR (epidermal growth factor receptor) tyrosine kinase inhibitors (TKIs), and/or angiogenesis inhibitors.

8. The method according to claim 1, wherein said tumor is selected from a group consisting of locally advanced-stage or metastatic melanoma, non-keratinized locally advanced recurrent or metastatic NPC, metastatic NSCLC, squamous and non-squamous NSCLC, recurrent or metastatic ESCC and Triple-negative breast cancer TNBC).

9. The method according to claim 1, wherein said dimer is administrated in combination with a chemotherapy agent.

10. The method according to claim 1, wherein said effective amount of the dimer is at a dose of 1 mg/kg to 5 mg/kg.

11. The method according to claim 1, wherein said dimer is administrated once every two weeks or once every three weeks.

12. A kit comprising an effective amount of said dimer according to claim 1, and chemotherapy agent.

* * * * *

SEQUENCE LISTING

```
<160> NUMBER OF SEQ ID NOS: 64

<210> SEQ ID NO 1
<211> LENGTH: 19
<212> TYPE: PRT
<213> ORGANISM: Artificial Sequence
<220> FEATURE:
<223> OTHER INFORMATION: CDR3 of antiPD-L1
<220> FEATURE:
<221> NAME/KEY: X
<222> LOCATION: (4)..(4)
<223> OTHER INFORMATION: X1=E/G
<220> FEATURE:
<221> NAME/KEY: X
<222> LOCATION: (5)..(5)
```

-continued

```
<223> OTHER INFORMATION: X=D/Y
<220> FEATURE:
<221> NAME/KEY: X
<222> LOCATION: (9)..(9)
<223> OTHER INFORMATION: ,X=T/P
<220> FEATURE:
<221> NAME/KEY: X
<222> LOCATION: (10)..(10)
<223> OTHER INFORMATION: ,X=L/G
<220> FEATURE:
<221> NAME/KEY: X
<222> LOCATION: (11)..(11)
<223> OTHER INFORMATION: ,X=V/P
<220> FEATURE:
<221> NAME/KEY: X
<222> LOCATION: (12)..(12)
<223> OTHER INFORMATION: X=T/A

<400> SEQUENCE: 1

Asp Ser Phe Xaa Xaa Pro Thr Cys Xaa Xaa Xaa Xaa Ser Ser Gly Ala
1               5                   10                  15

Phe Gln Tyr

<210> SEQ ID NO 2
<211> LENGTH: 10
<212> TYPE: PRT
<213> ORGANISM: Artificial Sequence
<220> FEATURE:
<223> OTHER INFORMATION: CDR1 of antiPD-L1
<220> FEATURE:
<221> NAME/KEY: X
<222> LOCATION: (2)..(2)
<223> OTHER INFORMATION: X=K/N
<220> FEATURE:
<221> NAME/KEY: X
<222> LOCATION: (3)..(3)
<223> OTHER INFORMATION: X=M/I
<220> FEATURE:
<221> NAME/KEY: X
<222> LOCATION: (4)..(4)
<223> OTHER INFORMATION: X=S/I
<220> FEATURE:
<221> NAME/KEY: X
<222> LOCATION: (5)..(5)
<223> OTHER INFORMATION: X=S/R
<220> FEATURE:
<221> NAME/KEY: X
<222> LOCATION: (6)..(6)
<223> OTHER INFORMATION: X=R/V

<400> SEQUENCE: 2

Gly Xaa Xaa Xaa Xaa Xaa Arg Cys Met Ala
1               5                   10

<210> SEQ ID NO 3
<211> LENGTH: 10
<212> TYPE: PRT
<213> ORGANISM: Artificial Sequence
<220> FEATURE:
<223> OTHER INFORMATION: PD-L1 ISVD-9 CDR1

<400> SEQUENCE: 3

Gly Lys Met Ser Ser Arg Arg Cys Met Ala
1               5                   10

<210> SEQ ID NO 4
<211> LENGTH: 17
<212> TYPE: PRT
<213> ORGANISM: Artificial Sequence
<220> FEATURE:
<223> OTHER INFORMATION: PD-L1 ISVD-9 CDR2
```

<400> SEQUENCE: 4

Lys Leu Leu Thr Thr Ser Gly Ser Thr Tyr Leu Ala Asp Ser Val Lys
1               5                   10                  15

Gly

<210> SEQ ID NO 5
<211> LENGTH: 19
<212> TYPE: PRT
<213> ORGANISM: Artificial Sequence
<220> FEATURE:
<223> OTHER INFORMATION: PD-L1 ISVD-9 CDR3

<400> SEQUENCE: 5

Asp Ser Phe Glu Asp Pro Thr Cys Thr Leu Val Thr Ser Ser Gly Ala
1               5                   10                  15

Phe Gln Tyr

<210> SEQ ID NO 6
<211> LENGTH: 128
<212> TYPE: PRT
<213> ORGANISM: Artificial Sequence
<220> FEATURE:
<223> OTHER INFORMATION: PD-L1 ISVD-9

<400> SEQUENCE: 6

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
            35                  40                  45

Ala Lys Leu Leu Thr Thr Ser Gly Ser Thr Tyr Leu Ala Asp Ser Val
        50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
            115                 120                 125

<210> SEQ ID NO 7
<211> LENGTH: 10
<212> TYPE: PRT
<213> ORGANISM: Artificial Sequence
<220> FEATURE:
<223> OTHER INFORMATION: PD-L1 ISVD-6 CDR1

<400> SEQUENCE: 7

Gly Asn Ile Ile Arg Val Arg Cys Met Ala
1               5                   10

<210> SEQ ID NO 8
<211> LENGTH: 17
<212> TYPE: PRT
<213> ORGANISM: Artificial Sequence
<220> FEATURE:
<223> OTHER INFORMATION: PD-L1 ISVD-6 CDR2

-continued

```
<400> SEQUENCE: 8

Asn Ile Leu Thr Thr Thr Ile Ser Thr Tyr Leu Ala Asp Ser Val Lys
1               5                   10                  15

Gly

<210> SEQ ID NO 9
<211> LENGTH: 19
<212> TYPE: PRT
<213> ORGANISM: Artificial Sequence
<220> FEATURE:
<223> OTHER INFORMATION: PD-L1 ISVD-6 CDR3

<400> SEQUENCE: 9

Asp Ser Phe Gly Tyr Pro Thr Cys Pro Gly Pro Ala Ser Ser Gly Ala
1               5                   10                  15

Phe Gln Tyr

<210> SEQ ID NO 10
<211> LENGTH: 128
<212> TYPE: PRT
<213> ORGANISM: Artificial Sequence
<220> FEATURE:
<223> OTHER INFORMATION: PD-L1 ISVD-6

<400> SEQUENCE: 10

Gln Val Gln Leu Gln Glu Ser Gly Gly Gly Ser Val Gln Ala Gly Gly
1               5                   10                  15

Ser Leu Arg Leu Ser Cys Ala Ala Ser Gly Asn Ile Ile Arg Val Arg
            20                  25                  30

Cys Met Ala Trp Phe Arg Gln Ala Pro Gly Lys Glu Arg Glu Arg Gly
        35                  40                  45

Pro Asn Ile Leu Thr Thr Thr Ile Ser Thr Tyr Leu Ala Asp Ser Val
    50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Gly Tyr Pro Thr Cys Pro Gly Pro Ala Ser Ser
            100                 105                 110

Gly Ala Phe Gln Tyr Trp Gly Gln Gly Thr Gln Val Thr Val Ser Ser
        115                 120                 125

<210> SEQ ID NO 11
<211> LENGTH: 17
<212> TYPE: PRT
<213> ORGANISM: Artificial Sequence
<220> FEATURE:
<223> OTHER INFORMATION: PD-L1 ISVD-m3 CDR2

<400> SEQUENCE: 11

Asp Val Asn Pro Asn Ser Gly Gly Ser Ile Tyr Asn Gln Arg Phe Lys
1               5                   10                  15

Gly

<210> SEQ ID NO 12
<211> LENGTH: 128
<212> TYPE: PRT
<213> ORGANISM: Artificial Sequence
<220> FEATURE:
<223> OTHER INFORMATION: PD-L1 ISVD-m3
```

-continued

<400> SEQUENCE: 12

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Asp Val Asn Pro Asn Ser Gly Gly Ser Ile Tyr Asn Gln Arg Phe
        50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Gln Val Thr Val Ser Ser
            115                 120                 125
```

```
<210> SEQ ID NO 13
<211> LENGTH: 128
<212> TYPE: PRT
<213> ORGANISM: Artificial Sequence
<220> FEATURE:
<223> OTHER INFORMATION: PD-L1 ISVD-4
```

<400> SEQUENCE: 13

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
        50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Gln Val Thr Val Ser Ser
            115                 120                 125
```

```
<210> SEQ ID NO 14
<211> LENGTH: 128
<212> TYPE: PRT
<213> ORGANISM: Artificial Sequence
<220> FEATURE:
<223> OTHER INFORMATION: PD-L1 ISVD-11
```

<400> SEQUENCE: 14

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Gly Leu Glu Arg Val
        35                  40                  45
```

```
Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
                100                 105                 110

Gly Ala Phe Gln Tyr Trp Gly Gln Gly Thr Leu Val Thr Val Ser Ser
            115                 120                 125
```

<210> SEQ ID NO 15
<211> LENGTH: 128
<212> TYPE: PRT
<213> ORGANISM: Artificial Sequence
<220> FEATURE:
<223> OTHER INFORMATION: PD-L1 ISVD-13

<400> SEQUENCE: 15

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
            35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Lys Ala Glu Asp Thr Ala Val Tyr Tyr Cys
                85                  90                  95

Ala Ala Asp Ser Phe Glu Asp Pro Thr Cys Thr Leu Val Thr Ser Ser
                100                 105                 110

Gly Ala Phe Gln Tyr Trp Gly Gln Gly Thr Leu Val Thr Val Ser Ser
            115                 120                 125
```

<210> SEQ ID NO 16
<211> LENGTH: 17
<212> TYPE: PRT
<213> ORGANISM: Artificial Sequence
<220> FEATURE:
<223> OTHER INFORMATION: CDR2 of CTLA4
<220> FEATURE:
<221> NAME/KEY: X
<222> LOCATION: (3)..(3)
<223> OTHER INFORMATION: X=Y/S
<220> FEATURE:
<221> NAME/KEY: X
<222> LOCATION: (4)..(4)
<223> OTHER INFORMATION: X=I/L

<400> SEQUENCE: 16

```
Ala Ile Xaa Xaa Gly Gly Gly Ser Thr Tyr Tyr Ala Asp Ser Val Lys
1               5                   10                  15

Gly
```

<210> SEQ ID NO 17
<211> LENGTH: 5
<212> TYPE: PRT
<213> ORGANISM: Artificial Sequence
<220> FEATURE:

```
<223> OTHER INFORMATION: CTLA4 ISVD-34 CDR1

<400> SEQUENCE: 17

Ala Tyr Cys Met Gly
1               5

<210> SEQ ID NO 18
<211> LENGTH: 17
<212> TYPE: PRT
<213> ORGANISM: Artificial Sequence
<220> FEATURE:
<223> OTHER INFORMATION: CTLA4 ISVD-34 CDR2

<400> SEQUENCE: 18

Ala Ile Tyr Ile Gly Gly Gly Ser Thr Tyr Tyr Ala Asp Ser Val Lys
1               5                   10                  15

Gly

<210> SEQ ID NO 19
<211> LENGTH: 19
<212> TYPE: PRT
<213> ORGANISM: Artificial Sequence
<220> FEATURE:
<223> OTHER INFORMATION: CTLA4 ISVD-34 CDR3

<400> SEQUENCE: 19

Asp Val Ile Pro Thr Glu Thr Cys Leu Gly Gly Ser Trp Ser Gly Pro
1               5                   10                  15

Phe Gly Tyr

<210> SEQ ID NO 20
<211> LENGTH: 128
<212> TYPE: PRT
<213> ORGANISM: Artificial Sequence
<220> FEATURE:
<223> OTHER INFORMATION: CTLA4 ISVD-34

<400> SEQUENCE: 20

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Glu Gly Val
            35                  40                  45

Ala Ala Ile Tyr Ile Gly Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

<210> SEQ ID NO 21
<211> LENGTH: 17
<212> TYPE: PRT
<213> ORGANISM: Artificial Sequence
<220> FEATURE:
<223> OTHER INFORMATION: CTLA4 ISVD-C1 CDR2
```

-continued

```
<400> SEQUENCE: 21

Ala Ile Tyr Leu Gly Gly Gly Ser Thr Tyr Tyr Ala Asp Ser Val Lys
1               5                   10                  15

Gly

<210> SEQ ID NO 22
<211> LENGTH: 128
<212> TYPE: PRT
<213> ORGANISM: Artificial Sequence
<220> FEATURE:
<223> OTHER INFORMATION: CTLA4 ISVD-C1

<400> SEQUENCE: 22

Gln Val Gln Leu Gln Glu Ser Gly Gly Gly Ser Val Gln Ala Gly Gly
1               5                   10                  15

Ser Leu Gly Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Glu Gly Val
        35                  40                  45

Ala Ala Ile Tyr Leu Gly Gly Gly Ser Thr Tyr Tyr Ala Asp Ser Val
    50                  55                  60

Lys Gly Arg Phe Thr Ile Ser Gln Asp Ile Ala Lys Asn Thr Leu Tyr
65                  70                  75                  80

Leu Gln Met Asn Ser Leu Lys Pro Glu Asp Thr Ala Met Tyr Ser Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Gln Val Thr Val Ser Ser
        115                 120                 125

<210> SEQ ID NO 23
<211> LENGTH: 17
<212> TYPE: PRT
<213> ORGANISM: Artificial Sequence
<220> FEATURE:
<223> OTHER INFORMATION: CTLA4 ISVD-13 CDR2

<400> SEQUENCE: 23

Ala Ile Ser Ile Gly Gly Gly Ser Thr Tyr Tyr Ala Asp Ser Val Lys
1               5                   10                  15

Gly

<210> SEQ ID NO 24
<211> LENGTH: 128
<212> TYPE: PRT
<213> ORGANISM: Artificial Sequence
<220> FEATURE:
<223> OTHER INFORMATION: CTLA4 ISVD-13

<400> SEQUENCE: 24

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Val Gly Val
        35                  40                  45

Ala Ala Ile Ser Ile Gly Gly Gly Ser Thr Tyr Tyr Ala Asp Ser Val
    50                  55                  60
```

```
Lys Gly Arg Phe Thr Ile Ser Gln Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Asp Val Ile Pro Thr Glu Thr Cys Leu Gly Gly Ser Trp Ser
                100                 105                 110

Gly Pro Phe Gly Tyr Trp Gly Gln Gly Thr Gln Val Thr Val Ser Ser
            115                 120                 125

<210> SEQ ID NO 25
<211> LENGTH: 128
<212> TYPE: PRT
<213> ORGANISM: Artificial Sequence
<220> FEATURE:
<223> OTHER INFORMATION: CTLA4 ISVD-26

<400> SEQUENCE: 25

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
                20                  25                  30

Cys Met Gly Trp Phe Arg Gln Ala Pro Gly Lys Glu Arg Val Gly Val
            35                  40                  45

Ala Ala Ile Ser Ile Gly Gly Gly Ser Thr Tyr Tyr Ala Asp Ser Val
        50                  55                  60

Lys Gly Arg Phe Thr Ile Ser Gln Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
                100                 105                 110

Gly Pro Phe Gly Tyr Trp Gly Gln Gly Thr Leu Val Thr Val Ser Ser
            115                 120                 125

<210> SEQ ID NO 26
<211> LENGTH: 128
<212> TYPE: PRT
<213> ORGANISM: Artificial Sequence
<220> FEATURE:
<223> OTHER INFORMATION: CTLA4 ISVD-27

<400> SEQUENCE: 26

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
                20                  25                  30

Cys Met Gly Trp Phe Arg Gln Ala Pro Gly Lys Glu Arg Val Gly Val
            35                  40                  45

Ala Ala Ile Ser Ile Gly Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
                100                 105                 110
```

-continued

```
Gly Pro Phe Gly Tyr Trp Gly Gln Gly Thr Leu Val Thr Val Ser Ser
        115                 120                 125

<210> SEQ ID NO 27
<211> LENGTH: 128
<212> TYPE: PRT
<213> ORGANISM: Artificial Sequence
<220> FEATURE:
<223> OTHER INFORMATION: CTLA4 ISVD-28

<400> SEQUENCE: 27

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Val Gly Val
        35                  40                  45

Ala Ala Ile Ser Ile Gly Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

<210> SEQ ID NO 28
<211> LENGTH: 128
<212> TYPE: PRT
<213> ORGANISM: Artificial Sequence
<220> FEATURE:
<223> OTHER INFORMATION: CTLA4 ISVD-29

<400> SEQUENCE: 28

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Glu Gly Val
        35                  40                  45

Ala Ala Ile Ser Ile Gly Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

<210> SEQ ID NO 29
<211> LENGTH: 128
<212> TYPE: PRT
<213> ORGANISM: Artificial Sequence
<220> FEATURE:
<223> OTHER INFORMATION: CTLA4 ISVD-30
```

<400> SEQUENCE: 29

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Glu Gly Val
        35                  40                  45

Ala Ala Ile Ser Ile Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125
```

<210> SEQ ID NO 30
<211> LENGTH: 128
<212> TYPE: PRT
<213> ORGANISM: Artificial Sequence
<220> FEATURE:
<223> OTHER INFORMATION: CTLA4 ISVD-31

<400> SEQUENCE: 30

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Glu Gly Val
        35                  40                  45

Ala Ala Ile Tyr Ile Gly Gly Ser Thr Tyr Tyr Ala Asp Ser Val
        50                  55                  60

Lys Gly Arg Phe Thr Ile Ser Gln Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125
```

<210> SEQ ID NO 31
<211> LENGTH: 128
<212> TYPE: PRT
<213> ORGANISM: Artificial Sequence
<220> FEATURE:
<223> OTHER INFORMATION: CTLA4 ISVD-32

<400> SEQUENCE: 31

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Glu Gly Val
        35                  40                  45
```

-continued

```
Ala Ala Ile Tyr Ile Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
               100                 105                 110

Gly Pro Phe Gly Tyr Trp Gly Gln Gly Thr Leu Val Thr Val Ser Ser
           115                 120                 125
```

<210> SEQ ID NO 32
<211> LENGTH: 128
<212> TYPE: PRT
<213> ORGANISM: Artificial Sequence
<220> FEATURE:
<223> OTHER INFORMATION: CTLA4 ISVD-33

<400> SEQUENCE: 32

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
                20                  25                  30

Cys Met Gly Trp Phe Arg Gln Ala Pro Gly Lys Gly Leu Val Gly Val
            35                  40                  45

Ala Ala Ile Tyr Ile Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
               100                 105                 110

Gly Pro Phe Gly Tyr Trp Gly Gln Gly Thr Leu Val Thr Val Ser Ser
           115                 120                 125
```

<210> SEQ ID NO 33
<211> LENGTH: 3
<212> TYPE: PRT
<213> ORGANISM: Artificial Sequence
<220> FEATURE:
<223> OTHER INFORMATION: short linker

<400> SEQUENCE: 33

```
Gly Ala Pro
1
```

<210> SEQ ID NO 34
<211> LENGTH: 15
<212> TYPE: PRT
<213> ORGANISM: Artificial Sequence
<220> FEATURE:
<223> OTHER INFORMATION: long linker

<400> SEQUENCE: 34

```
Gly Gly Gly Gly Ser Gly Gly Gly Gly Ser Gly Gly Gly Gly Ser
1               5                   10                  15
```

<210> SEQ ID NO 35
<211> LENGTH: 232

```
<212> TYPE: PRT
<213> ORGANISM: Artificial Sequence
<220> FEATURE:
<223> OTHER INFORMATION: IgG1-Fc region with hinge

<400> SEQUENCE: 35

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 36
<211> LENGTH: 330
<212> TYPE: PRT
<213> ORGANISM: Artificial Sequence
<220> FEATURE:
<223> OTHER INFORMATION: human IgG1 constant region

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 37
<211> LENGTH: 124
<212> TYPE: PRT
<213> ORGANISM: Artificial Sequence
<220> FEATURE:
<223> OTHER INFORMATION: control dAb

<400> SEQUENCE: 37

Gln Val Gln Leu Gln Glu Ser Gly Gly Gly Ser Val Gln Ala Gly Gly
1               5                   10                  15

Ser Leu Arg Leu Ser Cys Glu Ala Ser Gly Tyr Thr Tyr Cys Met Gly
            20                  25                  30

Trp Phe Arg Gln Ala Pro Gly Lys Glu Arg Glu Gly Val Ala Leu Ala
            35                  40                  45

Val Thr Gly Ile Ser Ile Pro Tyr Tyr Ala Asp Ser Val Lys Gly Arg
        50                  55                  60

Phe Thr Ile Ser Gln Asp Asn Val Lys Asn Thr Leu Tyr Leu Gln Met
65                  70                  75                  80

Asn Ser Leu Lys Pro Glu Asp Ala Ala Met Tyr Tyr Cys Ala Ala Ser
                85                  90                  95

Thr Ile Arg Tyr Val Cys Pro Gly Leu Asn Arg Gly Asp Gln Phe Lys
            100                 105                 110

Asn Trp Gly Gln Gly Thr Gln Val Thr Val Ser Ser
            115                 120
```

-continued

```
<210> SEQ ID NO 38
<211> LENGTH: 232
<212> TYPE: PRT
<213> ORGANISM: Artificial Sequence
<220> FEATURE:
<223> OTHER INFORMATION: IgG1-Fc region with hinge (C-S)

<400> SEQUENCE: 38

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 39
<211> LENGTH: 227
<212> TYPE: PRT
<213> ORGANISM: Artificial Sequence
<220> FEATURE:
<223> OTHER INFORMATION: human IgG1-Fc region without hinge

<400> SEQUENCE: 39

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

-continued

His Asn Ala Lys Thr Lys Pro Arg Glu Glu Gln Tyr Asn Ser Thr Tyr
65              70              75              80

Arg Val Val Ser Val Leu Thr Val Leu His Gln Asp Trp Leu Asn Gly
                85              90              95

Lys Glu Tyr Lys Cys Lys Val Ser Asn Lys Ala Leu Pro Ala Pro Ile
            100             105             110

Glu Lys Thr Ile Ser Lys Ala Lys Gly Gln Pro Arg Glu Pro Gln Val
            115             120             125

Tyr Thr Leu Pro Pro Ser Arg Asp Glu Leu Thr Lys Asn Gln Val Ser
        130             135             140

Leu Thr Cys Leu Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
                165             170             175

Val Leu Asp Ser Asp Gly Ser Phe Phe Leu Tyr Ser Lys Leu Thr Val
            180             185             190

Asp Lys Ser Arg Trp Gln Gln Gly Asn Val Phe Ser Cys Ser Val Met
        195             200             205

His Glu Ala Leu His Asn His Tyr Thr Gln Lys Ser Leu Ser Leu Ser
    210             215             220

Pro Gly Lys
225

<210> SEQ ID NO 40
<211> LENGTH: 493
<212> TYPE: PRT
<213> ORGANISM: Artificial Sequence
<220> FEATURE:
<223> OTHER INFORMATION: aPDL1.9-aCTLA4.34-Fc

<400> SEQUENCE: 40

Gln Val Gln Leu Val Glu Ser Gly Gly Gly Leu Val Gln Pro Gly Gly
1               5               10              15

Ser Leu Arg Leu Ser Cys Ala Ala Ser Gly Lys Met Ser Ser Arg Arg
            20              25              30

Cys Met Ala Trp Phe Arg Gln Ala Pro Gly Lys Glu Arg Glu Arg Val
            35              40              45

Ala Lys Leu Leu Thr Thr Ser Gly Ser Thr Tyr Leu Ala Asp Ser Val
        50              55              60

Lys Gly Arg Phe Thr Ile Ser Arg Asp Asn Ser Lys Asn Thr Val Tyr
65              70              75              80

Leu Gln Met Asn Ser Leu Arg Ala Glu Asp Thr Ala Val Tyr Tyr Cys
                85              90              95

Ala Ala Asp Ser Phe Glu Asp Pro Thr Cys Thr Leu Val Thr Ser Ser
            100             105             110

Gly Ala Phe Gln Tyr Trp Gly Gln Gly Thr Leu Val Thr Val Ser Ser
        115             120             125

Gly Ala Pro Gln Val Gln Leu Val Glu Ser Gly Gly Gly Leu Val Gln
        130             135             140

Pro Gly Gly Ser Leu Arg Leu Ser Cys Ala Ala Ser Gly Tyr Ile Tyr
145             150             155             160

Ser Ala Tyr Cys Met Gly Trp Phe Arg Gln Ala Pro Gly Lys Gly Leu
            165             170             175

Glu Gly Val Ala Ala Ile Tyr Ile Gly Gly Gly Ser Thr Tyr Tyr Ala
            180             185             190

-continued

```
Asp Ser Val Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
        210                 215                 220

Tyr Tyr Cys Ala Ala Asp Val Ile Pro Thr Glu Thr Cys Leu Gly Gly
225                 230                 235                 240

Ser Trp Ser Gly Pro Phe Gly Tyr Trp Gly Gln Gly Thr Leu Val Thr
                245                 250                 255

Val Ser Ser Gly Ser Glu Pro Lys Ser Ser Asp Lys Thr His Thr Cys
                260                 265                 270

Pro Pro Cys Pro Ala Pro Glu Leu Leu Gly Gly Pro Ser Val Phe Leu
                275                 280                 285

Phe Pro Pro Lys Pro Lys Asp Thr Leu Met Ile Ser Arg Thr Pro Glu
        290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
                340                 345                 350

Thr Val Leu His Gln Asp Trp Leu Asn Gly Lys Glu Tyr Lys Cys Lys
                355                 360                 365

Val Ser Asn Lys Ala Leu Pro Ala Pro Ile Glu Lys Thr Ile Ser Lys
        370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
                420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
        450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 41
<211> LENGTH: 505
<212> TYPE: PRT
<213> ORGANISM: Artificial Sequence
<220> FEATURE:
<223> OTHER INFORMATION: aPDL1.9-L-aCTLA4.34-Fc

<400> SEQUENCE: 41

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
        20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
        50                  55                  60
```

-continued

```
Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
            115                 120                 125

Gly Gly Gly Gly Ser Gly Gly Gly Ser Gly Gly Gly Gly Ser Gln
        130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Tyr Ile Tyr Ser Ala Tyr Cys
                165                 170                 175

Met Gly Trp Phe Arg Gln Ala Pro Gly Lys Gly Leu Glu Gly Val Ala
            180                 185                 190

Ala Ile Tyr Ile Gly Gly Gly Ser Thr Tyr Tyr Ala Asp Ser Val Lys
            195                 200                 205

Gly Arg Phe Thr Ile Ser Arg Asp Asn Ser Lys Asn Thr Leu Tyr Leu
        210                 215                 220

Gln Met Asn Ser Leu Arg Ala Glu Asp Thr Ala Val Tyr Tyr Cys Ala
225                 230                 235                 240

Ala Asp Val Ile Pro Thr Glu Thr Cys Leu Gly Gly Ser Trp Ser Gly
                245                 250                 255

Pro Phe Gly Tyr Trp Gly Gln Gly Thr Leu Val Thr Val Ser Ser Gly
            260                 265                 270

Ser Glu Pro Lys Ser Ser Asp Lys Thr His Thr Cys Pro Pro Cys Pro
            275                 280                 285

Ala Pro Glu Leu Leu Gly Gly Pro Ser Val Phe Leu Phe Pro Pro Lys
        290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
            355                 360                 365

Gln Asp Trp Leu Asn Gly Lys Glu Tyr Lys Cys Lys Val Ser Asn Lys
        370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Asp Glu Leu
            405                 410                 415

Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
            435                 440                 445

Tyr Lys Thr Thr Pro Pro Val Leu Asp Ser Asp Gly Ser Phe Phe Leu
        450                 455                 460

Tyr Ser Lys Leu Thr Val Asp Lys Ser Arg Trp Gln Gln Gly Asn Val
465                 470                 475                 480
```

```
Phe Ser Cys Ser Val Met His Glu Ala Leu His Asn His Tyr Thr Gln
                485             490             495

Lys Ser Leu Ser Leu Ser Pro Gly Lys
            500             505

<210> SEQ ID NO 42
<211> LENGTH: 493
<212> TYPE: PRT
<213> ORGANISM: Artificial Sequence
<220> FEATURE:
<223> OTHER INFORMATION: aCTLA4.34-aPDL1.9-Fc

<400> SEQUENCE: 42

Gln Val Gln Leu Val Glu Ser Gly Gly Gly Leu Val Gln Pro Gly Gly
1               5               10              15

Ser Leu Arg Leu Ser Cys Ala Ala Ser Gly Tyr Ile Tyr Ser Ala Tyr
            20              25              30

Cys Met Gly Trp Phe Arg Gln Ala Pro Gly Lys Gly Leu Glu Gly Val
        35              40              45

Ala Ala Ile Tyr Ile Gly Gly Gly Ser Thr Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Ala Asp Val Ile Pro Thr Glu Thr Cys Leu Gly Gly Ser Trp Ser
                100             105             110

Gly Pro Phe Gly Tyr Trp Gly Gln Gly Thr Leu Val Thr Val Ser Ser
            115             120             125

Gly Ala Pro Gln Val Gln Leu Val Glu Ser Gly Gly Gly Leu Val Gln
        130             135             140

Pro Gly Gly Ser Leu Arg Leu Ser Cys Ala Ala Ser Gly Lys Met Ser
145             150             155             160

Ser Arg Arg Cys Met Ala Trp Phe Arg Gln Ala Pro Gly Lys Glu Arg
                165             170             175

Glu Arg Val Ala Lys Leu Leu Thr Thr Ser Gly Ser Thr Tyr Leu Ala
            180             185             190

Asp Ser Val Lys Gly Arg Phe Thr Ile Ser Arg Asp Asn Ser Lys Asn
            195             200             205

Thr Val Tyr Leu Gln Met Asn Ser Leu Arg Ala Glu Asp Thr Ala Val
        210             215             220

Tyr Tyr Cys Ala Ala Asp Ser Phe Glu Asp Pro Thr Cys Thr Leu Val
225             230             235             240

Thr Ser Ser Gly Ala Phe Gln Tyr Trp Gly Gln Gly Thr Leu Val Thr
            245             250             255

Val Ser Ser Gly Ser Glu Pro Lys Ser Ser Asp Lys Thr His Thr Cys
            260             265             270

Pro Pro Cys Pro Ala Pro Glu Leu Leu Gly Gly Pro Ser Val Phe Leu
            275             280             285

Phe Pro Pro Lys Pro Lys Asp Thr Leu Met Ile Ser Arg Thr Pro Glu
    290             295             300

Val Thr Cys Val Val Val Asp Val Ser His Glu Asp Pro Glu Val Lys
305             310             315             320

Phe Asn Trp Tyr Val Asp Gly Val Glu Val His Asn Ala Lys Thr Lys
            325             330             335
```

-continued

```
Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
            355                 360                 365

Val Ser Asn Lys Ala Leu Pro Ala Pro Ile Glu Lys Thr Ile Ser Lys
            370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
            435                 440                 445

Ser Phe Phe Leu Tyr Ser Lys Leu Thr Val Asp Lys Ser Arg Trp Gln
            450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 43
<211> LENGTH: 505
<212> TYPE: PRT
<213> ORGANISM: Artificial Sequence
<220> FEATURE:
<223> OTHER INFORMATION: aCTLA4.34-L-aPDL1.9-FC

<400> SEQUENCE: 43

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Glu Gly Val
            35                  40                  45

Ala Ala Ile Tyr Ile Gly Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
                100                 105                 110

Gly Pro Phe Gly Tyr Trp Gly Gln Gly Thr Leu Val Thr Val Ser Ser
            115                 120                 125

Gly Gly Gly Gly Ser Gly Gly Gly Gly Ser Gly Gly Gly Gly Ser Gln
            130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Lys Met Ser Ser Arg Arg Cys
                165                 170                 175

Met Ala Trp Phe Arg Gln Ala Pro Gly Lys Glu Arg Glu Arg Val Ala
            180                 185                 190

Lys Leu Leu Thr Thr Ser Gly Ser Thr Tyr Leu Ala Asp Ser Val Lys
            195                 200                 205
```

-continued

```
Gly Arg Phe Thr Ile Ser Arg Asp Asn Ser Lys Asn Thr Val Tyr Leu
    210             215             220

Gln Met Asn Ser Leu Arg Ala Glu Asp Thr Ala Val Tyr Tyr Cys Ala
225             230             235             240

Ala Asp Ser Phe Glu Asp Pro Thr Cys Thr Leu Val Thr Ser Ser Gly
            245             250             255

Ala Phe Gln Tyr Trp Gly Gln Gly Thr Leu Val Thr Val Ser Ser Gly
            260             265             270

Ser Glu Pro Lys Ser Ser Asp Lys Thr His Thr Cys Pro Pro Cys Pro
            275             280             285

Ala Pro Glu Leu Leu Gly Gly Pro Ser Val Phe Leu Phe Pro Pro Lys
    290             295             300

Pro Lys Asp Thr Leu Met Ile Ser Arg Thr Pro Glu Val Thr Cys Val
305             310             315             320

Val Val Asp Val Ser His Glu Asp Pro Glu Val Lys Phe Asn Trp Tyr
            325             330             335

Val Asp Gly Val Glu Val His Asn Ala Lys Thr Lys Pro Arg Glu Glu
            340             345             350

Gln Tyr Asn Ser Thr Tyr Arg Val Val Ser Val Leu Thr Val Leu His
            355             360             365

Gln Asp Trp Leu Asn Gly Lys Glu Tyr Lys Cys Lys Val Ser Asn Lys
    370             375             380

Ala Leu Pro Ala Pro Ile Glu Lys Thr Ile Ser Lys Ala Lys Gly Gln
385             390             395             400

Pro Arg Glu Pro Gln Val Tyr Thr Leu Pro Pro Ser Arg Asp Glu Leu
            405             410             415

Thr Lys Asn Gln Val Ser Leu Thr Cys Leu Val Lys Gly Phe Tyr Pro
            420             425             430

Ser Asp Ile Ala Val Glu Trp Glu Ser Asn Gly Gln Pro Glu Asn Asn
            435             440             445

Tyr Lys Thr Thr Pro Pro Val Leu Asp Ser Asp Gly Ser Phe Phe Leu
    450             455             460

Tyr Ser Lys Leu Thr Val Asp Lys Ser Arg Trp Gln Gln Gly Asn Val
465             470             475             480

Phe Ser Cys Ser Val Met His Glu Ala Leu His Asn His Tyr Thr Gln
            485             490             495

Lys Ser Leu Ser Leu Ser Pro Gly Lys
            500             505
```

```
<210> SEQ ID NO 44
<211> LENGTH: 487
<212> TYPE: PRT
<213> ORGANISM: Artificial Sequence
<220> FEATURE:
<223> OTHER INFORMATION: aPDL1.9-dAb-Fc

<400> SEQUENCE: 44

Gln Val Gln Leu Val Glu Ser Gly Gly Gly Leu Val Gln Pro Gly Gly
1               5               10              15

Ser Leu Arg Leu Ser Cys Ala Ala Ser Gly Lys Met Ser Ser Arg Arg
            20              25              30

Cys Met Ala Trp Phe Arg Gln Ala Pro Gly Lys Glu Arg Glu Arg Val
            35              40              45

Ala Lys Leu Leu Thr Thr Ser Gly Ser Thr Tyr Leu Ala Asp Ser Val
    50              55              60
```

```
Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
            115                 120                 125

Gly Ala Pro Gln Val Gln Leu Gln Glu Ser Gly Gly Gly Ser Val Gln
            130                 135                 140

Ala Gly Gly Ser Leu Arg Leu Ser Cys Glu Ala Ser Gly Tyr Thr Tyr
145                 150                 155                 160

Cys Met Gly Trp Phe Arg Gln Ala Pro Gly Lys Glu Arg Glu Gly Val
                165                 170                 175

Ala Leu Ala Val Thr Gly Ile Ser Ile Pro Tyr Tyr Ala Asp Ser Val
            180                 185                 190

Lys Gly Arg Phe Thr Ile Ser Gln Asp Asn Val Lys Asn Thr Leu Tyr
            195                 200                 205

Leu Gln Met Asn Ser Leu Lys Pro Glu Asp Ala Ala Met Tyr Tyr Cys
    210                 215                 220

Ala Ala Ser Thr Ile Arg Tyr Val Cys Pro Gly Leu Asn Arg Gly Asp
225                 230                 235                 240

Gln Phe Lys Asn Trp Gly Gln Gly Thr Gln Val Thr Val Ser Ser Glu
                245                 250                 255

Pro Lys Ser Ser Asp Lys Thr His Thr Cys Pro Pro Cys Pro Ala Pro
            260                 265                 270

Glu Leu Leu Gly Gly Pro Ser Val Phe Leu Phe Pro Pro Lys Pro Lys
            275                 280                 285

Asp Thr Leu Met Ile Ser Arg Thr Pro Glu Val Thr Cys Val Val Val
            290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Ala Leu
            355                 360                 365

Pro Ala Pro Ile Glu Lys Thr Ile Ser Lys Ala Lys Gly Gln Pro Arg
    370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Tyr Ser
            435                 440                 445

Lys Leu Thr Val Asp Lys Ser Arg Trp Gln Gln Gly Asn Val Phe Ser
    450                 455                 460

Cys Ser Val Met His Glu Ala Leu His Asn His Tyr Thr Gln Lys Ser
465                 470                 475                 480
```

-continued

Leu Ser Leu Ser Pro Gly Lys
            485

<210> SEQ ID NO 45
<211> LENGTH: 487
<212> TYPE: PRT
<213> ORGANISM: Artificial Sequence
<220> FEATURE:
<223> OTHER INFORMATION: dAb-aCTLA4.34-Fc

<400> SEQUENCE: 45

Gln Val Gln Leu Gln Glu Ser Gly Gly Gly Ser Val Gln Ala Gly Gly
1               5                   10                  15

Ser Leu Arg Leu Ser Cys Glu Ala Ser Gly Tyr Thr Tyr Cys Met Gly
            20                  25                  30

Trp Phe Arg Gln Ala Pro Gly Lys Glu Arg Glu Gly Val Ala Leu Ala
            35                  40                  45

Val Thr Gly Ile Ser Ile Pro Tyr Tyr Ala Asp Ser Val Lys Gly Arg
            50                  55                  60

Phe Thr Ile Ser Gln Asp Asn Val Lys Asn Thr Leu Tyr Leu Gln Met
65                  70                  75                  80

Asn Ser Leu Lys Pro Glu Asp Ala Ala Met Tyr Tyr Cys Ala Ala Ser
                85                  90                  95

Thr Ile Arg Tyr Val Cys Pro Gly Leu Asn Arg Gly Asp Gln Phe Lys
            100                 105                 110

Asn Trp Gly Gln Gly Thr Gln Val Thr Val Ser Ser Gly Ala Pro Gln
            115                 120                 125

Val Gln Leu Val Glu Ser Gly Gly Gly Leu Val Gln Pro Gly Gly Ser
            130                 135                 140

Leu Arg Leu Ser Cys Ala Ala Ser Gly Tyr Ile Tyr Ser Ala Tyr Cys
145                 150                 155                 160

Met Gly Trp Phe Arg Gln Ala Pro Gly Lys Gly Leu Glu Gly Val Ala
                165                 170                 175

Ala Ile Tyr Ile Gly Gly Gly Ser Thr Tyr Tyr Ala Asp Ser Val Lys
            180                 185                 190

Gly Arg Phe Thr Ile Ser Arg Asp Asn Ser Lys Asn Thr Leu Tyr Leu
            195                 200                 205

Gln Met Asn Ser Leu Arg Ala Glu Asp Thr Ala Val Tyr Tyr Cys Ala
            210                 215                 220

Ala Asp Val Ile Pro Thr Glu Thr Cys Leu Gly Gly Ser Trp Ser Gly
225                 230                 235                 240

Pro Phe Gly Tyr Trp Gly Gln Gly Thr Leu Val Thr Val Ser Ser Glu
                245                 250                 255

Pro Lys Ser Ser Asp Lys Thr His Thr Cys Pro Pro Cys Pro Ala Pro
                260                 265                 270

Glu Leu Leu Gly Gly Pro Ser Val Phe Leu Phe Pro Pro Lys Pro Lys
            275                 280                 285

Asp Thr Leu Met Ile Ser Arg Thr Pro Glu Val Thr Cys Val Val Val
            290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
                340                 345                 350

-continued

```
Trp Leu Asn Gly Lys Glu Tyr Lys Cys Lys Val Ser Asn Lys Ala Leu
        355                 360                 365

Pro Ala Pro Ile Glu Lys Thr Ile Ser Lys Ala Lys Gly Gln Pro Arg
        370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
                420                 425                 430

Thr Thr Pro Pro Val Leu Asp Ser Asp Gly Ser Phe Phe Leu Tyr Ser
        435                 440                 445

Lys Leu Thr Val Asp Lys Ser Arg Trp Gln Gln Gly Asn Val Phe Ser
        450                 455                 460

Cys Ser Val Met His Glu Ala Leu His Asn His Tyr Thr Gln Lys Ser
465                 470                 475                 480

Leu Ser Leu Ser Pro Gly Lys
                485
```

```
<210> SEQ ID NO 46
<211> LENGTH: 491
<212> TYPE: PRT
<213> ORGANISM: Artificial Sequence
<220> FEATURE:
<223> OTHER INFORMATION: aPDL1.6-aCTLA4.34-Fc

<400> SEQUENCE: 46

Gln Val Gln Leu Gln Glu Ser Gly Gly Gly Ser Val Gln Ala Gly Gly
1               5                   10                  15

Ser Leu Arg Leu Ser Cys Ala Ala Ser Gly Asn Ile Ile Arg Val Arg
        20                  25                  30

Cys Met Ala Trp Phe Arg Gln Ala Pro Gly Lys Glu Arg Glu Arg Gly
        35                  40                  45

Pro Asn Ile Leu Thr Thr Thr Ile Ser Thr Tyr Leu Ala Asp Ser Val
        50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Gly Tyr Pro Thr Cys Pro Gly Pro Ala Ser Ser
                100                 105                 110

Gly Ala Phe Gln Tyr Trp Gly Gln Gly Thr Gln Val Thr Val Ser Ser
        115                 120                 125

Gly Ala Pro Gln Val Gln Leu Val Glu Ser Gly Gly Gly Leu Val Gln
        130                 135                 140

Pro Gly Gly Ser Leu Arg Leu Ser Cys Ala Ala Ser Gly Tyr Ile Tyr
145                 150                 155                 160

Ser Ala Tyr Cys Met Gly Trp Phe Arg Gln Ala Pro Gly Lys Gly Leu
                165                 170                 175

Glu Gly Val Ala Ala Ile Tyr Ile Gly Gly Gly Ser Thr Tyr Tyr Ala
                180                 185                 190

Asp Ser Val Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
        210                 215                 220
```

-continued

```
Tyr Tyr Cys Ala Ala Asp Val Ile Pro Thr Glu Thr Cys Leu Gly Gly
225             230             235             240

Ser Trp Ser Gly Pro Phe Gly Tyr Trp Gly Gln Gly Thr Leu Val Thr
            245             250             255

Val Ser Ser Glu Pro Lys Ser Ser Asp Lys Thr His Thr Cys Pro Pro
            260             265             270

Cys Pro Ala Pro Glu Leu Leu Gly Gly Pro Ser Val Phe Leu Phe Pro
            275             280             285

Pro Lys Pro Lys Asp Thr Leu Met Ile Ser Arg Thr Pro Glu Val Thr
            290             295             300

Cys Val Val Val Asp Val Ser His Glu Asp Pro Glu Val Lys Phe Asn
305             310             315             320

Trp Tyr Val Asp Gly Val Glu Val His Asn Ala Lys Thr Lys Pro Arg
            325             330             335

Glu Glu Gln Tyr Asn Ser Thr Tyr Arg Val Val Ser Val Leu Thr Val
            340             345             350

Leu His Gln Asp Trp Leu Asn Gly Lys Glu Tyr Lys Cys Lys Val Ser
            355             360             365

Asn Lys Ala Leu Pro Ala Pro Ile Glu Lys Thr Ile Ser Lys Ala Lys
            370             375             380

Gly Gln Pro Arg Glu Pro Gln Val Tyr Thr Leu Pro Pro Ser Arg Asp
385             390             395             400

Glu Leu Thr Lys Asn Gln Val Ser Leu Thr Cys Leu Val Lys Gly Phe
            405             410             415

Tyr Pro Ser Asp Ile Ala Val Glu Trp Glu Ser Asn Gly Gln Pro Glu
            420             425             430

Asn Asn Tyr Lys Thr Thr Pro Pro Val Leu Asp Ser Asp Gly Ser Phe
            435             440             445

Phe Leu Tyr Ser Lys Leu Thr Val Asp Lys Ser Arg Trp Gln Gln Gly
    450             455             460

Asn Val Phe Ser Cys Ser Val Met His Glu Ala Leu His Asn His Tyr
465             470             475             480

Thr Gln Lys Ser Leu Ser Leu Ser Pro Gly Lys
            485             490
```

```
<210> SEQ ID NO 47
<211> LENGTH: 487
<212> TYPE: PRT
<213> ORGANISM: Artificial Sequence
<220> FEATURE:
<223> OTHER INFORMATION: aPDL1.6-dAb-Fc

<400> SEQUENCE: 47
```

```
Gln Val Gln Leu Gln Glu Ser Gly Gly Gly Ser Val Gln Ala Gly Gly
1               5               10              15

Ser Leu Arg Leu Ser Cys Ala Ala Ser Gly Asn Ile Ile Arg Val Arg
            20              25              30

Cys Met Ala Trp Phe Arg Gln Ala Pro Gly Lys Glu Arg Glu Arg Gly
            35              40              45

Pro Asn Ile Leu Thr Thr Thr Ile Ser Thr Tyr Leu Ala Asp Ser Val
    50              55              60

Lys Gly Arg Phe Thr Ile Ser Gln Asn Asn Ala Lys Ser Thr Val Tyr
65              70              75              80

Leu Gln Met Asn Ser Leu Lys Pro Glu Asp Thr Ala Met Tyr Tyr Cys
            85              90              95
```

-continued

```
Ala Ala Asp Ser Phe Gly Tyr Pro Thr Cys Pro Gly Pro Ala Ser Ser
            100                 105             110

Gly Ala Phe Gln Tyr Trp Gly Gln Gly Thr Gln Val Thr Val Ser Ser
            115                 120             125

Gly Ala Pro Gln Val Gln Leu Gln Glu Ser Gly Gly Gly Ser Val Gln
        130                 135             140

Ala Gly Gly Ser Leu Arg Leu Ser Cys Glu Ala Ser Gly Tyr Thr Tyr
145             150                 155             160

Cys Met Gly Trp Phe Arg Gln Ala Pro Gly Lys Glu Arg Glu Gly Val
                165                 170             175

Ala Leu Ala Val Thr Gly Ile Ser Ile Pro Tyr Tyr Ala Asp Ser Val
            180                 185             190

Lys Gly Arg Phe Thr Ile Ser Gln Asp Asn Val Lys Asn Thr Leu Tyr
        195                 200             205

Leu Gln Met Asn Ser Leu Lys Pro Glu Asp Ala Ala Met Tyr Tyr Cys
    210                 215             220

Ala Ala Ser Thr Ile Arg Tyr Val Cys Pro Gly Leu Asn Arg Gly Asp
225                 230                 235             240

Gln Phe Lys Asn Trp Gly Gln Gly Thr Gln Val Thr Val Ser Ser Glu
                245                 250             255

Pro Lys Ser Ser Asp Lys Thr His Thr Cys Pro Pro Cys Pro Ala Pro
                260                 265             270

Glu Leu Leu Gly Gly Pro Ser Val Phe Leu Phe Pro Pro Lys Pro Lys
            275                 280             285

Asp Thr Leu Met Ile Ser Arg Thr Pro Glu Val Thr Cys Val Val Val
    290                 295             300

Asp Val Ser His Glu Asp Pro Glu Val Lys Phe Asn Trp Tyr Val Asp
305                 310                 315             320

Gly Val Glu Val His Asn Ala Lys Thr Lys Pro Arg Glu Glu Gln Tyr
                325                 330             335

Asn Ser Thr Tyr Arg Val Val Ser Val Leu Thr Val Leu His Gln Asp
            340                 345             350

Trp Leu Asn Gly Lys Glu Tyr Lys Cys Lys Val Ser Asn Lys Ala Leu
        355                 360             365

Pro Ala Pro Ile Glu Lys Thr Ile Ser Lys Ala Lys Gly Gln Pro Arg
    370                 375             380

Glu Pro Gln Val Tyr Thr Leu Pro Pro Ser Arg Asp Glu Leu Thr Lys
385                 390                 395             400

Asn Gln Val Ser Leu Thr Cys Leu Val Lys Gly Phe Tyr Pro Ser Asp
                405                 410             415

Ile Ala Val Glu Trp Glu Ser Asn Gly Gln Pro Glu Asn Asn Tyr Lys
            420                 425             430

Thr Thr Pro Pro Val Leu Asp Ser Asp Gly Ser Phe Phe Leu Tyr Ser
        435                 440             445

Lys Leu Thr Val Asp Lys Ser Arg Trp Gln Gln Gly Asn Val Phe Ser
    450                 455             460

Cys Ser Val Met His Glu Ala Leu His Asn His Tyr Thr Gln Lys Ser
465                 470                 475             480

Leu Ser Leu Ser Pro Gly Lys
                485
```

<210> SEQ ID NO 48
<211> LENGTH: 491

-continued

<212> TYPE: PRT
<213> ORGANISM: Artificial Sequence
<220> FEATURE:
<223> OTHER INFORMATION: aPDL1.m3-aCTLA4.34-Fc

<400> SEQUENCE: 48

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Asp Val Asn Pro Asn Ser Gly Gly Ser Ile Tyr Asn Gln Arg Phe
    50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Gln Val Thr Val Ser Ser
            115                 120                 125

Gly Ala Pro Gln Val Gln Leu Val Glu Ser Gly Gly Gly Leu Val Gln
        130                 135                 140

Pro Gly Gly Ser Leu Arg Leu Ser Cys Ala Ala Ser Gly Tyr Ile Tyr
145                 150                 155                 160

Ser Ala Tyr Cys Met Gly Trp Phe Arg Gln Ala Pro Gly Lys Gly Leu
                165                 170                 175

Glu Gly Val Ala Ala Ile Tyr Ile Gly Gly Gly Ser Thr Tyr Tyr Ala
            180                 185                 190

Asp Ser Val Lys Gly Arg Phe Thr Ile Ser Arg Asp Asn Ser Lys Asn
            195                 200                 205

Thr Leu Tyr Leu Gln Met Asn Ser Leu Arg Ala Glu Asp Thr Ala Val
        210                 215                 220

Tyr Tyr Cys Ala Ala Asp Val Ile Pro Thr Glu Thr Cys Leu Gly Gly
225                 230                 235                 240

Ser Trp Ser Gly Pro Phe Gly Tyr Trp Gly Gln Gly Thr Leu Val Thr
                245                 250                 255

Val Ser Ser Glu Pro Lys Ser Ser Asp Lys Thr His Thr Cys Pro Pro
            260                 265                 270

Cys Pro Ala Pro Glu Leu Leu Gly Gly Pro Ser Val Phe Leu Phe Pro
        275                 280                 285

Pro Lys Pro Lys Asp Thr Leu Met Ile Ser Arg Thr Pro Glu Val Thr
        290                 295                 300

Cys Val Val Val Asp Val Ser His Glu Asp Pro Glu Val Lys Phe Asn
305                 310                 315                 320

Trp Tyr Val Asp Gly Val Glu Val His Asn Ala Lys Thr Lys Pro Arg
                325                 330                 335

Glu Glu Gln Tyr Asn Ser Thr Tyr Arg Val Val Ser Val Leu Thr Val
            340                 345                 350

Leu His Gln Asp Trp Leu Asn Gly Lys Glu Tyr Lys Cys Lys Val Ser
        355                 360                 365

Asn Lys Ala Leu Pro Ala Pro Ile Glu Lys Thr Ile Ser Lys Ala Lys
        370                 375                 380
```

-continued

```
Gly Gln Pro Arg Glu Pro Gln Val Tyr Thr Leu Pro Pro Ser Arg Asp
385             390             395             400

Glu Leu Thr Lys Asn Gln Val Ser Leu Thr Cys Leu Val Lys Gly Phe
                405             410             415

Tyr Pro Ser Asp Ile Ala Val Glu Trp Glu Ser Asn Gly Gln Pro Glu
                420             425             430

Asn Asn Tyr Lys Thr Thr Pro Pro Val Leu Asp Ser Asp Gly Ser Phe
            435             440             445

Phe Leu Tyr Ser Lys Leu Thr Val Asp Lys Ser Arg Trp Gln Gln Gly
        450             455             460

Asn Val Phe Ser Cys Ser Val Met His Glu Ala Leu His Asn His Tyr
465             470             475             480

Thr Gln Lys Ser Leu Ser Leu Ser Pro Gly Lys
                485             490
```

```
<210> SEQ ID NO 49
<211> LENGTH: 487
<212> TYPE: PRT
<213> ORGANISM: Artificial Sequence
<220> FEATURE:
<223> OTHER INFORMATION: aPDL1.m3-dAb-Fc

<400> SEQUENCE: 49
```

```
Gln Val Gln Leu Gln Glu Ser Gly Gly Gly Leu Val Gln Pro Gly Gly
1               5               10              15

Ser Leu Arg Leu Ser Cys Ala Ala Ser Gly Lys Met Ser Ser Arg Arg
                20              25              30

Cys Met Ala Trp Phe Arg Gln Ala Pro Gly Lys Glu Arg Glu Arg Val
                35              40              45

Ala Asp Val Asn Pro Asn Ser Gly Gly Ser Ile Tyr Asn Gln Arg Phe
        50              55              60

Lys Gly Arg Phe Thr Ile Ser Gln Asn Asn Ala Lys Ser Thr Val Tyr
65              70              75              80

Leu Gln Met Asn Ser Leu Lys Pro Glu Asp Thr Ala Met Tyr Tyr Cys
                85              90              95

Ala Ala Asp Ser Phe Glu Asp Pro Thr Cys Thr Leu Val Thr Ser Ser
            100             105             110

Gly Ala Phe Gln Tyr Trp Gly Gln Gly Thr Gln Val Thr Val Ser Ser
        115             120             125

Gly Ala Pro Gln Val Gln Leu Gln Glu Ser Gly Gly Gly Ser Val Gln
        130             135             140

Ala Gly Gly Ser Leu Arg Leu Ser Cys Glu Ala Ser Gly Tyr Thr Tyr
145             150             155             160

Cys Met Gly Trp Phe Arg Gln Ala Pro Gly Lys Glu Arg Glu Gly Val
                165             170             175

Ala Leu Ala Val Thr Gly Ile Ser Ile Pro Tyr Tyr Ala Asp Ser Val
            180             185             190

Lys Gly Arg Phe Thr Ile Ser Gln Asp Asn Val Lys Asn Thr Leu Tyr
                195             200             205

Leu Gln Met Asn Ser Leu Lys Pro Glu Asp Ala Ala Met Tyr Tyr Cys
        210             215             220

Ala Ala Ser Thr Ile Arg Tyr Val Cys Pro Gly Leu Asn Arg Gly Asp
225             230             235             240

Gln Phe Lys Asn Trp Gly Gln Gly Thr Gln Val Thr Val Ser Ser Glu
                245             250             255
```

```
Pro Lys Ser Ser Asp Lys Thr His Thr Cys Pro Pro Cys Pro Ala Pro
            260                 265                 270

Glu Leu Leu Gly Gly Pro Ser Val Phe Leu Phe Pro Pro Lys Pro Lys
            275                 280                 285

Asp Thr Leu Met Ile Ser Arg Thr Pro Glu Val Thr Cys Val Val Val
            290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
                340                 345                 350

Trp Leu Asn Gly Lys Glu Tyr Lys Cys Lys Val Ser Asn Lys Ala Leu
            355                 360                 365

Pro Ala Pro Ile Glu Lys Thr Ile Ser Lys Ala Lys Gly Gln Pro Arg
            370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
                420                 425                 430

Thr Thr Pro Pro Val Leu Asp Ser Asp Gly Ser Phe Phe Leu Tyr Ser
            435                 440                 445

Lys Leu Thr Val Asp Lys Ser Arg Trp Gln Gln Gly Asn Val Phe Ser
            450                 455                 460

Cys Ser Val Met His Glu Ala Leu His Asn His Tyr Thr Gln Lys Ser
465                 470                 475                 480

Leu Ser Leu Ser Pro Gly Lys
                485
```

<210> SEQ ID NO 50
<211> LENGTH: 491
<212> TYPE: PRT
<213> ORGANISM: Artificial Sequence
<220> FEATURE:
<223> OTHER INFORMATION: aPDL1.9-aCTLA4.13-Fc

<400> SEQUENCE: 50

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
            35                  40                  45

Ala Lys Leu Leu Thr Thr Ser Gly Ser Thr Tyr Leu Ala Asp Ser Val
            50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
            115                 120                 125
```

-continued

```
Gly Ala Pro Gln Val Gln Leu Gln Glu Ser Gly Gly Gly Ser Val Gln
130             135                 140

Ala Gly Gly Ser Leu Arg Leu Ser Cys Ala Ala Ser Gly Tyr Ile Tyr
145             150                 155                 160

Ser Ala Tyr Cys Met Gly Trp Phe Arg Gln Ala Pro Gly Lys Glu Arg
                165             170                 175

Val Gly Val Ala Ala Ile Ser Ile Gly Gly Gly Ser Thr Tyr Tyr Ala
                180             185                 190

Asp Ser Val Lys Gly Arg Phe Thr Ile Ser Gln Asp Asn Ala Lys Asn
                195             200                 205

Thr Leu Tyr Leu Gln Met Asn Ser Leu Lys Pro Glu Asp Thr Ala Met
210             215                 220

Tyr Tyr Cys Ala Ala Asp Val Ile Pro Thr Glu Thr Cys Leu Gly Gly
225             230                 235                 240

Ser Trp Ser Gly Pro Phe Gly Tyr Trp Gly Gln Gly Thr Gln Val Thr
                245             250                 255

Val Ser Ser Glu Pro Lys Ser Ser Asp Lys Thr His Thr Cys Pro Pro
                260             265                 270

Cys Pro Ala Pro Glu Leu Leu Gly Gly Pro Ser Val Phe Leu Phe Pro
                275             280                 285

Pro Lys Pro Lys Asp Thr Leu Met Ile Ser Arg Thr Pro Glu Val Thr
                290             295                 300

Cys Val Val Val Asp Val Ser His Glu Asp Pro Glu Val Lys Phe Asn
305             310                 315                 320

Trp Tyr Val Asp Gly Val Glu Val His Asn Ala Lys Thr Lys Pro Arg
                325             330                 335

Glu Glu Gln Tyr Asn Ser Thr Tyr Arg Val Val Ser Val Leu Thr Val
                340             345                 350

Leu His Gln Asp Trp Leu Asn Gly Lys Glu Tyr Lys Cys Lys Val Ser
                355             360                 365

Asn Lys Ala Leu Pro Ala Pro Ile Glu Lys Thr Ile Ser Lys Ala Lys
        370             375                 380

Gly Gln Pro Arg Glu Pro Gln Val Tyr Thr Leu Pro Pro Ser Arg Asp
385             390                 395                 400

Glu Leu Thr Lys Asn Gln Val Ser Leu Thr Cys Leu Val Lys Gly Phe
                405             410                 415

Tyr Pro Ser Asp Ile Ala Val Glu Trp Glu Ser Asn Gly Gln Pro Glu
                420             425                 430

Asn Asn Tyr Lys Thr Thr Pro Pro Val Leu Asp Ser Asp Gly Ser Phe
                435             440                 445

Phe Leu Tyr Ser Lys Leu Thr Val Asp Lys Ser Arg Trp Gln Gln Gly
        450             455                 460

Asn Val Phe Ser Cys Ser Val Met His Glu Ala Leu His Asn His Tyr
465             470                 475                 480

Thr Gln Lys Ser Leu Ser Leu Ser Pro Gly Lys
                485                 490
```

<210> SEQ ID NO 51
<211> LENGTH: 487
<212> TYPE: PRT
<213> ORGANISM: Artificial Sequence
<220> FEATURE:
<223> OTHER INFORMATION: dAb-aCTLA4.13-Fc -continued

```
<400> SEQUENCE: 51

Gln Val Gln Leu Gln Glu Ser Gly Gly Gly Ser Val Gln Ala Gly Gly
1               5                   10                  15

Ser Leu Arg Leu Ser Cys Glu Ala Ser Gly Tyr Thr Tyr Cys Met Gly
            20                  25                  30

Trp Phe Arg Gln Ala Pro Gly Lys Glu Arg Glu Gly Val Ala Leu Ala
        35                  40                  45

Val Thr Gly Ile Ser Ile Pro Tyr Tyr Ala Asp Ser Val Lys Gly Arg
        50                  55                  60

Phe Thr Ile Ser Gln Asp Asn Val Lys Asn Thr Leu Tyr Leu Gln Met
65                  70                  75                  80

Asn Ser Leu Lys Pro Glu Asp Ala Ala Met Tyr Tyr Cys Ala Ala Ser
                85                  90                  95

Thr Ile Arg Tyr Val Cys Pro Gly Leu Asn Arg Gly Asp Gln Phe Lys
            100                 105                 110

Asn Trp Gly Gln Gly Thr Gln Val Thr Val Ser Ser Gly Ala Pro Gln
            115                 120                 125

Val Gln Leu Gln Glu Ser Gly Gly Gly Ser Val Gln Ala Gly Gly Ser
        130                 135                 140

Leu Arg Leu Ser Cys Ala Ala Ser Gly Tyr Ile Tyr Ser Ala Tyr Cys
145                 150                 155                 160

Met Gly Trp Phe Arg Gln Ala Pro Gly Lys Glu Arg Val Gly Val Ala
            165                 170                 175

Ala Ile Ser Ile Gly Gly Gly Ser Thr Tyr Tyr Ala Asp Ser Val Lys
            180                 185                 190

Gly Arg Phe Thr Ile Ser Gln Asp Asn Ala Lys Asn Thr Leu Tyr Leu
            195                 200                 205

Gln Met Asn Ser Leu Lys Pro Glu Asp Thr Ala Met Tyr Tyr Cys Ala
        210                 215                 220

Ala Asp Val Ile Pro Thr Glu Thr Cys Leu Gly Gly Ser Trp Ser Gly
225                 230                 235                 240

Pro Phe Gly Tyr Trp Gly Gln Gly Thr Gln Val Thr Val Ser Ser Glu
            245                 250                 255

Pro Lys Ser Ser Asp Lys Thr His Thr Cys Pro Pro Cys Pro Ala Pro
            260                 265                 270

Glu Leu Leu Gly Gly Pro Ser Val Phe Leu Phe Pro Pro Lys Pro Lys
        275                 280                 285

Asp Thr Leu Met Ile Ser Arg Thr Pro Glu Val Thr Cys Val Val Val
        290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
            325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Ala Leu
            355                 360                 365

Pro Ala Pro Ile Glu Lys Thr Ile Ser Lys Ala Lys Gly Gln Pro Arg
        370                 375                 380

Glu Pro Gln Val Tyr Thr Leu Pro Pro Ser Arg Asp Glu Leu Thr Lys
385                 390                 395                 400
```

```
Asn Gln Val Ser Leu Thr Cys Leu Val Lys Gly Phe Tyr Pro Ser Asp
              405                 410                 415

Ile Ala Val Glu Trp Glu Ser Asn Gly Gln Pro Glu Asn Asn Tyr Lys
              420                 425                 430

Thr Thr Pro Pro Val Leu Asp Ser Asp Gly Ser Phe Phe Leu Tyr Ser
              435                 440                 445

Lys Leu Thr Val Asp Lys Ser Arg Trp Gln Gln Gly Asn Val Phe Ser
      450                 455                 460

Cys Ser Val Met His Glu Ala Leu His Asn His Tyr Thr Gln Lys Ser
465                 470                 475                 480

Leu Ser Leu Ser Pro Gly Lys
              485

<210> SEQ ID NO 52
<211> LENGTH: 357
<212> TYPE: PRT
<213> ORGANISM: Artificial Sequence
<220> FEATURE:
<223> OTHER INFORMATION: CTLA4-muFc

<400> SEQUENCE: 52

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
              20                  25                  30

Arg Val Thr Val Leu Arg Gln Ala Asp Ser Gln Val Thr Glu Val Cys
              35                  40                  45

Ala Ala Thr Tyr Met Met Gly Asn Glu Leu Thr Phe Leu Asp Asp Ser
      50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
              85                  90                  95

Met Tyr Pro Pro Pro Tyr Tyr Leu Gly Ile Gly Asn Gly Thr Gln Ile
              100                 105                 110

Tyr Val Ile Asp Pro Glu Pro Cys Pro Asp Ser Asp Gln Gly Ser Met
              115                 120                 125

Asp Pro Lys Ser Ser Asp Lys Thr His Thr Cys Pro Pro Cys Pro Ala
      130                 135                 140

Pro Glu Val Ser Ser Val Phe Ile Phe Pro Pro Lys Pro Lys Asp Val
145                 150                 155                 160

Leu Thr Ile Thr Leu Thr Pro Lys Val Thr Cys Val Val Val Asp Ile
              165                 170                 175

Ser Lys Asp Asp Pro Glu Val Gln Phe Ser Trp Phe Val Asp Asp Val
              180                 185                 190

Glu Val His Thr Ala Gln Thr Gln Pro Arg Glu Glu Gln Phe Asn Ser
              195                 200                 205

Thr Phe Arg Ser Val Ser Glu Leu Pro Ile Met His Gln Asp Trp Leu
      210                 215                 220

Asn Gly Lys Glu Phe Lys Cys Arg Val Asn Ser Ala Ala Phe Pro Ala
225                 230                 235                 240

Pro Ile Glu Lys Thr Ile Ser Lys Thr Lys Gly Arg Pro Lys Ala Pro
              245                 250                 255

Gln Val Tyr Thr Ile Pro Pro Pro Lys Glu Gln Met Ala Lys Asp Lys
              260                 265                 270
```

```
Val Ser Leu Thr Cys Met Ile Thr Asp Phe Phe Pro Glu Asp Ile Thr
        275                 280                 285

Val Glu Trp Gln Trp Asn Gly Gln Pro Ala Glu Asn Tyr Lys Asn Thr
        290                 295                 300

Gln Pro Ile Met Asn Thr Asn Gly Ser Tyr Phe Val Tyr Ser Lys Leu
305                 310                 315                 320

Asn Val Gln Lys Ser Asn Trp Glu Ala Gly Asn Thr Phe Thr Cys Ser
                325                 330                 335

Val Leu His Glu Gly Leu His Asn His His Thr Glu Lys Ser Leu Ser
                340                 345                 350

His Ser Pro Gly Lys
        355

<210> SEQ ID NO 53
<211> LENGTH: 452
<212> TYPE: PRT
<213> ORGANISM: Artificial Sequence
<220> FEATURE:
<223> OTHER INFORMATION: PD-L1-muFc

<400> SEQUENCE: 53

Thr Val Thr Val Pro Lys Asp Leu Tyr Val Val Glu Tyr Gly Ser Asn
1               5                   10                  15

Met Thr Ile Glu Cys Lys Phe Pro Val Glu Lys Gln Leu Asp Leu Ala
            20                  25                  30

Ala Leu Ile Val Tyr Trp Glu Met Glu Asp Lys Asn Ile Ile Gln Phe
            35                  40                  45

Val His Gly Glu Glu Asp Leu Lys Val Gln His Ser Ser Tyr Arg Gln
        50                  55                  60

Arg Ala Arg Leu Leu Lys Asp Gln Leu Ser Leu Gly Asn Ala Ala Leu
65                  70                  75                  80

Gln Ile Thr Asp Val Lys Leu Gln Asp Ala Gly Val Tyr Arg Cys Met
                85                  90                  95

Ile Ser Tyr Gly Gly Ala Asp Tyr Lys Arg Ile Thr Val Lys Val Asn
            100                 105                 110

Ala Pro Tyr Asn Lys Ile Asn Gln Arg Ile Leu Val Val Asp Pro Val
        115                 120                 125

Thr Ser Glu His Glu Leu Thr Cys Gln Ala Glu Gly Tyr Pro Lys Ala
        130                 135                 140

Glu Val Ile Trp Thr Ser Ser Asp His Gln Val Leu Ser Gly Lys Thr
145                 150                 155                 160

Thr Thr Thr Asn Ser Lys Arg Glu Glu Asn Leu Phe Asn Val Thr Ser
                165                 170                 175

Thr Leu Arg Ile Asn Thr Thr Thr Asn Glu Ile Phe Tyr Cys Thr Phe
            180                 185                 190

Arg Arg Leu Asp Pro Glu Glu Asn His Thr Ala Glu Leu Val Ile Pro
        195                 200                 205

Glu Leu Pro Leu Ala His Pro Pro Asn Glu Arg Thr Gly Ser Met Asp
        210                 215                 220

Pro Lys Ser Ser Asp Lys Thr His Thr Cys Pro Pro Cys Pro Ala Pro
225                 230                 235                 240

Glu Val Ser Ser Val Phe Ile Phe Pro Pro Lys Pro Lys Asp Val Leu
                245                 250                 255

Thr Ile Thr Leu Thr Pro Lys Val Thr Cys Val Val Val Asp Ile Ser
            260                 265                 270
```

-continued

```
Lys Asp Asp Pro Glu Val Gln Phe Ser Trp Phe Val Asp Asp Val Glu
        275                 280                 285

Val His Thr Ala Gln Thr Gln Pro Arg Glu Glu Gln Phe Asn Ser Thr
    290                 295                 300

Phe Arg Ser Val Ser Glu Leu Pro Ile Met His Gln Asp Trp Leu Asn
305                 310                 315                 320

Gly Lys Glu Phe Lys Cys Arg Val Asn Ser Ala Ala Phe Pro Ala Pro
                325                 330                 335

Ile Glu Lys Thr Ile Ser Lys Thr Lys Gly Arg Pro Lys Ala Pro Gln
                340                 345                 350

Val Tyr Thr Ile Pro Pro Pro Lys Glu Gln Met Ala Lys Asp Lys Val
            355                 360                 365

Ser Leu Thr Cys Met Ile Thr Asp Phe Phe Pro Glu Asp Ile Thr Val
    370                 375                 380

Glu Trp Gln Trp Asn Gly Gln Pro Ala Glu Asn Tyr Lys Asn Thr Gln
385                 390                 395                 400

Pro Ile Met Asn Thr Asn Gly Ser Tyr Phe Val Tyr Ser Lys Leu Asn
                405                 410                 415

Val Gln Lys Ser Asn Trp Glu Ala Gly Asn Thr Phe Thr Cys Ser Val
                420                 425                 430

Leu His Glu Gly Leu His Asn His His Thr Glu Lys Ser Leu Ser His
            435                 440                 445

Ser Pro Gly Lys
        450

<210> SEQ ID NO 54
<211> LENGTH: 448
<212> TYPE: PRT
<213> ORGANISM: Artificial Sequence
<220> FEATURE:
<223> OTHER INFORMATION: PD-L1-huFc

<400> SEQUENCE: 54

Thr Val Thr Val Pro Lys Asp Leu Tyr Val Val Glu Tyr Gly Ser Asn
1               5                   10                  15

Met Thr Ile Glu Cys Lys Phe Pro Val Glu Lys Gln Leu Asp Leu Ala
                20                  25                  30

Ala Leu Ile Val Tyr Trp Glu Met Glu Asp Lys Asn Ile Ile Gln Phe
            35                  40                  45

Val His Gly Glu Glu Asp Leu Lys Val Gln His Ser Ser Tyr Arg Gln
    50                  55                  60

Arg Ala Arg Leu Leu Lys Asp Gln Leu Ser Leu Gly Asn Ala Ala Leu
65                  70                  75                  80

Gln Ile Thr Asp Val Lys Leu Gln Asp Ala Gly Val Tyr Arg Cys Met
                85                  90                  95

Ile Ser Tyr Gly Gly Ala Asp Tyr Lys Arg Ile Thr Val Lys Val Asn
            100                 105                 110

Ala Pro Tyr Asn Lys Ile Asn Gln Arg Ile Leu Val Val Asp Pro Val
        115                 120                 125

Thr Ser Glu His Glu Leu Thr Cys Gln Ala Glu Gly Tyr Pro Lys Ala
    130                 135                 140

Glu Val Ile Trp Thr Ser Ser Asp His Gln Val Leu Ser Gly Lys Thr
145                 150                 155                 160

Thr Thr Thr Asn Ser Lys Arg Glu Glu Asn Leu Phe Asn Val Thr Ser
                165                 170                 175
```

-continued

```
Thr Leu Arg Ile Asn Thr Thr Thr Asn Glu Ile Phe Tyr Cys Thr Phe
            180                 185                 190

Arg Arg Leu Asp Pro Glu Glu Asn His Thr Ala Glu Leu Val Ile Pro
            195                 200                 205

Glu Leu Pro Leu Ala His Pro Pro Asn Glu Arg Thr Asp Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445
```

```
<210> SEQ ID NO 55
<211> LENGTH: 442
<212> TYPE: PRT
<213> ORGANISM: Artificial Sequence
<220> FEATURE:
<223> OTHER INFORMATION: CD80-muFc

<400> SEQUENCE: 55
```

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
            35                  40                  45

Ile Trp Pro Glu Tyr Lys Asn Arg Thr Ile Phe Asp Ile Thr Asn Asn
            50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95
```

-continued

```
Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
            115                 120                 125

Ser Thr Ser Gly Gly Phe Pro Glu Pro His Leu Ser Trp Leu Glu Asn
            130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
            195                 200                 205

Ile Glu Gly Arg Met Asp Pro Lys Ser Ser Asp Lys Thr His Thr Cys
            210                 215                 220

Pro Pro Cys Pro Ala Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
                260                 265                 270

Phe Val Asp Asp Val Glu Val His Thr Ala Gln Thr Gln Pro Arg Glu
            275                 280                 285

Glu Gln Phe Asn Ser Thr Phe Arg Ser Val Ser Glu Leu Pro Ile Met
            290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
            355                 360                 365

Pro Glu Asp Ile Thr Val Glu Trp Gln Trp Asn Gly Gln Pro Ala Glu
            370                 375                 380

Asn Tyr Lys Asn Thr Gln Pro Ile Met Asn Thr Asn Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
                420                 425                 430

Glu Lys Ser Leu Ser His Ser Pro Gly Lys
            435                 440
```

<210> SEQ ID NO 56
<211> LENGTH: 357
<212> TYPE: PRT
<213> ORGANISM: Artificial Sequence
<220> FEATURE:
<223> OTHER INFORMATION: CTLA4-huFc

<400> SEQUENCE: 56

```
Met His Val Ala Gln Pro Ala Val Val Leu Ala Ser Ser Arg Gly Ile
1               5                   10                  15
```

-continued

```
Ala Ser Phe Val Cys Glu Tyr Ala Ser Pro Gly Lys Ala Thr Glu Val
              20                  25                  30

Arg Val Thr Val Leu Arg Gln Ala Asp Ser Gln Val Thr Glu Val Cys
              35                  40                  45

Ala Ala Thr Tyr Met Met Gly Asn Glu Leu Thr Phe Leu Asp Asp Ser
         50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                   85                  90                  95

Met Tyr Pro Pro Pro Tyr Tyr Leu Gly Ile Gly Asn Gly Thr Gln Ile
              100                 105                 110

Tyr Val Ile Asp Pro Glu Pro Cys Pro Asp Ser Asp Gln Glu Pro Lys
              115                 120                 125

Ser Ser Asp Lys Thr His Thr Cys Pro Pro Cys Pro Ala Pro Glu Leu
         130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                   165                 170                 175

Ser His Glu Asp Pro Glu Val Lys Phe Asn Trp Tyr Val Asp Gly Val
              180                 185                 190

Glu Val His Asn Ala Lys Thr Lys Pro Arg Glu Glu Gln Tyr Asn Ser
              195                 200                 205

Thr Tyr Arg Val Val Ser Val Leu Thr Val Leu His Gln Asp Trp Leu
         210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                   245                 250                 255

Gln Val Tyr Thr Leu Pro Pro Ser Arg Asp Glu Leu Thr Lys Asn Gln
              260                 265                 270

Val Ser Leu Thr Cys Leu Val Lys Gly Phe Tyr Pro Ser Asp Ile Ala
              275                 280                 285

Val Glu Trp Glu Ser Asn Gly Gln Pro Glu Asn Asn Tyr Lys Thr Thr
         290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                   325                 330                 335

Val Met His Glu Ala Leu His Asn His Tyr Thr Gln Lys Ser Leu Ser
              340                 345                 350

Leu Ser Pro Gly Lys
         355

<210> SEQ ID NO 57
<211> LENGTH: 449
<212> TYPE: PRT
<213> ORGANISM: Artificial Sequence
<220> FEATURE:
<223> OTHER INFORMATION: CD86-muFc

<400> SEQUENCE: 57

Tyr Phe Asn Glu Thr Ala Asp Leu Pro Cys Gln Phe Ala Asn Ser Gln
1               5                   10                  15
```

-continued

```
Asn Gln Ser Leu Ser Glu Leu Val Val Phe Trp Gln Asp Gln Glu Asn
        20              25              30

Leu Val Leu Asn Glu Val Tyr Leu Gly Lys Glu Lys Phe Asp Ser Val
        35              40              45

His Ser Lys Tyr Met Gly Arg Thr Ser Phe Asp Ser Asp Ser Trp Thr
        50              55              60

Leu Arg Leu His Asn Leu Gln Ile Lys Asp Lys Gly Leu Tyr Gln Cys
65              70              75              80

Ile Ile His His Lys Lys Pro Thr Gly Met Ile Arg Ile His Gln Met
                85              90              95

Asn Ser Glu Leu Ser Val Leu Ala Asn Phe Ser Gln Pro Glu Ile Val
        100             105             110

Pro Ile Ser Asn Ile Thr Glu Asn Val Tyr Ile Asn Leu Thr Cys Ser
        115             120             125

Ser Ile His Gly Tyr Pro Glu Pro Lys Lys Met Ser Val Leu Leu Arg
        130             135             140

Thr Lys Asn Ser Thr Ile Glu Tyr Asp Gly Ile Met Gln Lys Ser Gln
145             150             155             160

Asp Asn Val Thr Glu Leu Tyr Asp Val Ser Ile Ser Leu Ser Val Ser
        165             170             175

Phe Pro Asp Val Thr Ser Asn Met Thr Ile Phe Cys Ile Leu Glu Thr
        180             185             190

Asp Lys Thr Arg Leu Leu Ser Ser Pro Phe Ser Ile Glu Leu Glu Asp
        195             200             205

Pro Gln Pro Pro Pro Asp His Ile Pro Gly Ser Met Asp Pro Lys Ser
        210             215             220

Ser Asp Lys Thr His Thr Cys Pro Pro Cys Pro Ala Pro Glu Val Ser
225             230             235             240

Ser Val Phe Ile Phe Pro Pro Lys Pro Lys Asp Val Leu Thr Ile Thr
        245             250             255

Leu Thr Pro Lys Val Thr Cys Val Val Val Asp Ile Ser Lys Asp Asp
        260             265             270

Pro Glu Val Gln Phe Ser Trp Phe Val Asp Asp Val Glu Val His Thr
        275             280             285

Ala Gln Thr Gln Pro Arg Glu Glu Gln Phe Asn Ser Thr Phe Arg Ser
        290             295             300

Val Ser Glu Leu Pro Ile Met His Gln Asp Trp Leu Asn Gly Lys Glu
305             310             315             320

Phe Lys Cys Arg Val Asn Ser Ala Ala Phe Pro Ala Pro Ile Glu Lys
        325             330             335

Thr Ile Ser Lys Thr Lys Gly Arg Pro Lys Ala Pro Gln Val Tyr Thr
        340             345             350

Ile Pro Pro Pro Lys Glu Gln Met Ala Lys Asp Lys Val Ser Leu Thr
        355             360             365

Cys Met Ile Thr Asp Phe Phe Pro Glu Asp Ile Thr Val Glu Trp Gln
        370             375             380

Trp Asn Gly Gln Pro Ala Glu Asn Tyr Lys Asn Thr Gln Pro Ile Met
385             390             395             400

Asn Thr Asn Gly Ser Tyr Phe Val Tyr Ser Lys Leu Asn Val Gln Lys
        405             410             415

Ser Asn Trp Glu Ala Gly Asn Thr Phe Thr Cys Ser Val Leu His Glu
        420             425             430
```

-continued

```
Gly Leu His Asn His His Thr Glu Lys Ser Leu Ser His Ser Pro Gly
        435                 440                 445

Lys

<210> SEQ ID NO 58
<211> LENGTH: 381
<212> TYPE: PRT
<213> ORGANISM: Artificial Sequence
<220> FEATURE:
<223> OTHER INFORMATION: PD1-muFc

<400> SEQUENCE: 58

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Ile Glu Gly Arg Met Asp Pro Lys Ser Ser Asp Lys Thr
145                 150                 155                 160

His Thr Cys Pro Pro Cys Pro Ala Pro Glu Val Ser Ser Val Phe Ile
                165                 170                 175

Phe Pro Pro Lys Pro Lys Asp Val Leu Thr Ile Thr Leu Thr Pro Lys
            180                 185                 190

Val Thr Cys Val Val Val Asp Ile Ser Lys Asp Asp Pro Glu Val Gln
        195                 200                 205

Phe Ser Trp Phe Val Asp Asp Val Glu Val His Thr Ala Gln Thr Gln
    210                 215                 220

Pro Arg Glu Glu Gln Phe Asn Ser Thr Phe Arg Ser Val Ser Glu Leu
225                 230                 235                 240

Pro Ile Met His Gln Asp Trp Leu Asn Gly Lys Glu Phe Lys Cys Arg
                245                 250                 255

Val Asn Ser Ala Ala Phe Pro Ala Pro Ile Glu Lys Thr Ile Ser Lys
            260                 265                 270

Thr Lys Gly Arg Pro Lys Ala Pro Gln Val Tyr Thr Ile Pro Pro Pro
        275                 280                 285

Lys Glu Gln Met Ala Lys Asp Lys Val Ser Leu Thr Cys Met Ile Thr
    290                 295                 300

Asp Phe Phe Pro Glu Asp Ile Thr Val Glu Trp Gln Trp Asn Gly Gln
305                 310                 315                 320

Pro Ala Glu Asn Tyr Lys Asn Thr Gln Pro Ile Met Asn Thr Asn Gly
                325                 330                 335
```

Ser Tyr Phe Val Tyr Ser Lys Leu Asn Val Gln Lys Ser Asn Trp Glu
                340                 345                 350

Ala Gly Asn Thr Phe Thr Cys Ser Val Leu His Glu Gly Leu His Asn
        355                 360                 365

His His Thr Glu Lys Ser Leu Ser His Ser Pro Gly Lys
    370                 375                 380

<210> SEQ ID NO 59
<211> LENGTH: 448
<212> TYPE: PRT
<213> ORGANISM: Artificial Sequence
<220> FEATURE:
<223> OTHER INFORMATION: Ipilimumab HC

<400> SEQUENCE: 59

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

-continued

```
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445
```

<210> SEQ ID NO 60
<211> LENGTH: 215
<212> TYPE: PRT
<213> ORGANISM: Artificial Sequence
<220> FEATURE:
<223> OTHER INFORMATION: Ipilimumab LC

<400> SEQUENCE: 60

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Phe Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
        210                 215
```

<210> SEQ ID NO 61

```
<211> LENGTH: 451
<212> TYPE: PRT
<213> ORGANISM: Artificial Sequence
<220> FEATURE:
<223> OTHER INFORMATION: Durvalumab HC

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380
```

-continued

```
Trp Glu Ser Asn Gly Gln Pro Glu Asn Asn Tyr Lys Thr Thr Pro Pro
385             390             395             400

Val Leu Asp Ser Asp Gly Ser Phe Phe Leu Tyr Ser Lys Leu Thr Val
            405             410             415

Asp Lys Ser Arg Trp Gln Gln Gly Asn Val Phe Ser Cys Ser Val Met
            420             425             430

His Glu Ala Leu His Asn His Tyr Thr Gln Lys Ser Leu Ser Leu Ser
            435             440             445

Pro Gly Lys
    450

<210> SEQ ID NO 62
<211> LENGTH: 215
<212> TYPE: PRT
<213> ORGANISM: Artificial Sequence
<220> FEATURE:
<223> OTHER INFORMATION: Durvalumab LC

<400> SEQUENCE: 62

Glu Ile Val Leu Thr Gln Ser Pro Gly Thr Leu Ser Leu Ser Pro Gly
1               5               10              15

Glu Arg Ala Thr Leu Ser Cys Arg Ala Ser Gln Arg Val Ser Ser Ser
            20              25              30

Tyr Leu Ala Trp Tyr Gln Gln Lys Pro Gly Gln Ala Pro Arg Leu Leu
            35              40              45

Ile Tyr Asp Ala Ser Ser Arg Ala Thr Gly Ile Pro Asp Arg Phe Ser
            50              55              60

Gly Ser Gly Ser Gly Thr Asp Phe Thr Leu Thr Ile Ser Arg Leu Glu
65              70              75              80

Pro Glu Asp Phe Ala Val Tyr Tyr Cys Gln Gln Tyr Gly Ser Leu Pro
                85              90              95

Trp Thr Phe Gly Gln Gly Thr Lys Val Glu Ile Lys Arg Thr Val Ala
            100             105             110

Ala Pro Ser Val Phe Ile Phe Pro Pro Ser Asp Glu Gln Leu Lys Ser
            115             120             125

Gly Thr Ala Ser Val Val Cys Leu Leu Asn Asn Phe Tyr Pro Arg Glu
            130             135             140

Ala Lys Val Gln Trp Lys Val Asp Asn Ala Leu Gln Ser Gly Asn Ser
145             150             155             160

Gln Glu Ser Val Thr Glu Gln Asp Ser Lys Asp Ser Thr Tyr Ser Leu
            165             170             175

Ser Ser Thr Leu Thr Leu Ser Lys Ala Asp Tyr Glu Lys His Lys Val
            180             185             190

Tyr Ala Cys Glu Val Thr His Gln Gly Leu Ser Ser Pro Val Thr Lys
            195             200             205

Ser Phe Asn Arg Gly Glu Cys
    210             215

<210> SEQ ID NO 63
<211> LENGTH: 220
<212> TYPE: PRT
<213> ORGANISM: Artificial Sequence
<220> FEATURE:
<223> OTHER INFORMATION: human PD-L1
```

-continued

<400> SEQUENCE: 63

```
Thr Val Thr Val Pro Lys Asp Leu Tyr Val Val Glu Tyr Gly Ser Asn
1               5                   10                  15

Met Thr Ile Glu Cys Lys Phe Pro Val Glu Lys Gln Leu Asp Leu Ala
            20                  25                  30

Ala Leu Ile Val Tyr Trp Glu Met Glu Asp Lys Asn Ile Ile Gln Phe
        35                  40                  45

Val His Gly Glu Glu Asp Leu Lys Val Gln His Ser Ser Tyr Arg Gln
    50                  55                  60

Arg Ala Arg Leu Leu Lys Asp Gln Leu Ser Leu Gly Asn Ala Ala Leu
65                  70                  75                  80

Gln Ile Thr Asp Val Lys Leu Gln Asp Ala Gly Val Tyr Arg Cys Met
            85                  90                  95

Ile Ser Tyr Gly Gly Ala Asp Tyr Lys Arg Ile Thr Val Lys Val Asn
            100                 105                 110

Ala Pro Tyr Asn Lys Ile Asn Gln Arg Ile Leu Val Val Asp Pro Val
            115                 120                 125

Thr Ser Glu His Glu Leu Thr Cys Gln Ala Glu Gly Tyr Pro Lys Ala
            130                 135                 140

Glu Val Ile Trp Thr Ser Ser Asp His Gln Val Leu Ser Gly Lys Thr
145                 150                 155                 160

Thr Thr Thr Asn Ser Lys Arg Glu Glu Asn Leu Phe Asn Val Thr Ser
                165                 170                 175

Thr Leu Arg Ile Asn Thr Thr Thr Asn Glu Ile Phe Tyr Cys Thr Phe
            180                 185                 190

Arg Arg Leu Asp Pro Glu Glu Asn His Thr Ala Glu Leu Val Ile Pro
            195                 200                 205

Glu Leu Pro Leu Ala His Pro Pro Asn Glu Arg Thr
    210                 215                 220
```

<210> SEQ ID NO 64
<211> LENGTH: 127
<212> TYPE: PRT
<213> ORGANISM: Artificial Sequence
<220> FEATURE:
<223> OTHER INFORMATION: N-terminal IgV domain of human PD-L1

<400> SEQUENCE: 64

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
            85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr
            115                 120                 125
```